United States Patent [19]

Barker et al.

[11] Patent Number: 5,395,838

[45] Date of Patent: Mar. 7, 1995

[54] 6-SUBSTITUTED QUINAZOLINES PROCESSING ANTI-TUMOR ACTIVITY

[75] Inventors: Andrew J. Barker; Leslie R. Hughes, both of Macclesfield; Peter R. Marsham, Poynton; John Oldfield, Wilmslow; Stephen J. Pegg, Macclesfield, all of England

[73] Assignees: Imperial Chemical Industries PLC; National Research Development Corporation, both of London, England

[21] Appl. No.: 91,828

[22] Filed: Jul. 13, 1993

Related U.S. Application Data

[62] Division of Ser. No. 793,183, Nov. 18, 1991, Pat. No. 5,252,573, which is a division of Ser. No. 450,670, Dec. 14, 1989, Pat. No. 5,089,499.

[30] Foreign Application Priority Data

Dec. 15, 1988 [GB] United Kingdom ............... 8829296

[51] Int. Cl.$^6$ ............... A61K 31/505; A01N 43/54; C07D 239/96; C07D 239/72
[52] U.S. Cl. .................. 514/211; 514/259; 514/260; 544/284; 544/285; 544/287; 544/289; 540/544
[58] Field of Search ............... 514/211, 259, 260; 544/284, 285, 287; 540/544

[56] References Cited

U.S. PATENT DOCUMENTS

| | | | |
|---|---|---|---|
| 4,447,608 | 5/1984 | Jones et al. | 544/287 |
| 4,564,616 | 1/1986 | Jones et al. | 514/260 |
| 4,857,530 | 8/1989 | Berman et al. | 514/259 |
| 4,981,856 | 1/1991 | Hughes | 514/259 |
| 4,992,550 | 2/1991 | Hughes | 544/284 |

FOREIGN PATENT DOCUMENTS 0316657 5/1989 European Pat. Off. .
0365763 5/1990 European Pat. Off. .

OTHER PUBLICATIONS

Poster presentation made in Zurich in the week Sep. 3-9, 1989, G. M. F. Bisset et al.; "Synthesis of Lipophilic Analogues . . .".

Primary Examiner—Mukund J. Shah
Assistant Examiner—Matthew V. Grumbling
Attorney, Agent, or Firm—Cushman Darby & Cushman

[57] ABSTRACT

The invention relates to quinazoline derivatives, or pharmaceutically-acceptable salts thereof, which possess anti-tumour activity; to processes for their manufacture; and to pharmaceutical compositions containing them.

The invention provides a quinazoline of the formula:

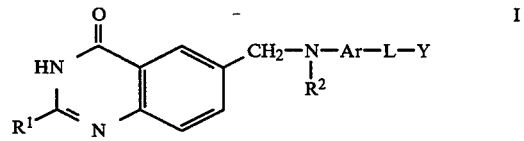

I wherein
$R^1$ is hydrogen or amino, or alkyl or alkoxy each of up to 6 carbon atoms; or $R^1$ is substituted alkyl or alkoxy each of up to 3 carbon atoms;
$R^2$ is hydrogen, alkyl, alkenyl, alkynyl, hydroxyalkyl, halogenoalkyl or cyanoalkyl each of up to 6 carbon atoms;
Ar is phenylene or heterocyclene;
L is a group of the formula —CO.NH—, —NH.CO—, —CO.NR$^3$—, —NR$^3$.CO—, —CH=CH—, —CH$_2$O—, —OCH$_2$—, —CH$_2$S—, —SCH$_2$—, —CO.CH$_2$—, —CH$_2$.CO— or —CO.O—, wherein R$^3$ is alkyl of up to 6 carbon atoms; and
Y is aryl or heteroaryl or a hydrogenated derivative thereof; or
Y is a group of the formula —A—Y$^1$ in which A is alkylene, cycloalkylene, alkenylene or alkynylene each of up to 6 carbon atoms and Y$^1$ is aryl or heteroaryl or a hydrogenated derivative thereof;
or a pharmaceutically-acceptable salt thereof.

13 Claims, No Drawings

6-SUBSTITUTED QUINAZOLINES PROCESSING ANTI-TUMOR ACTIVITY

This is a division of application Ser. No. 07/793,183, filed Nov. 18, 1991, now U.S. Pat. No. 5,252,573, which was a division of application Ser. No. 07/450,670, filed Dec. 14, 1989, now U.S. Pat. No. 5,089,499.

This invention relates to novel anti-tumour agents and more particularly it relates to quinazoline derivatives, or pharmaceutically-acceptable salts thereof, which possess anti-tumour activity. The invention includes novel quinazoline derivatives and processes for their manufacture; novel pharmaceutical compositions containing said quinazoline derivatives and the use of said quinazoline derivatives in the manufacture of novel medicaments for use in the production of an anti-tumour effect in a warm-blooded animal such as man.

One group of anti-tumour agents comprises the antimetabolites, such as aminopterin and methotrexate, which are inhibitors of enzymes which utilise folic acid derivatives. A newer compound of this type which showed considerable promise in clinical trials is known as CB3717 and is described and claimed in United Kingdom Patent Specification No. 2065653B. Despite its promising activity against human breast, ovarian and liver cancer, however, CB3717 shows symptoms of toxicity in humans, particularly in relation to the liver and kidney [Calvert, Alison, Harland, Robinson, Jackman, Jones, Newell, Siddik, Whiltshaw, McElwain, Smith and Harrap, *J. Clin. Oncol.*, 1986, 4, 1245; Cantwell, Earnshaw and Harris, *Cancer Treatment Reports*, 1986, 70, 1335; Bassendine, Curtin, Loose, Harris and James, *J. Hepatol.*, 1987, 4, 39; Vest, Bork and Hasen, *Eur. J. Cancer Clin. Oncol.*, 1988, 24, 201; Cantwell, Macaulay, Harris, Kaye, Smith, Milsted and Calvert, *Eur. J. Cancer Clin. Oncol.*, 1988, 24, 733; Sessa, Zucchetti, Ginier, Willems, D'Incalci and Cavalli, *Eur. J. Cancer Clin. Oncol.*, 1988, 24, 769].

Compounds of the CB3717-type are believed to act as anti-tumour agents by inhibiting the enzyme thymidylate synthase, which enzyme catalyses the methylation of deoxyuridine monophosphate to produce thymidine monophosphate which is required for DNA synthesis. The anti-tumour activity of CB3717 may be assessed in vitro by determining its inhibitory effect on that enzyme, and in cell cultures by its inhibitory effect on cancer cell lines such as the mouse leukaemia cell lines L1210 and L5178Y TK-/- and the human breast cancer cell line MCF-7.

Other compounds of the CB3717-type may therefore have their anti-tumour activity assessed and compared with that of CB3717, by their activity against, for example, the same enzyme and the same cancer cell lines.

European Patent Application No. 0316657 (published May 24, 1989) discloses a series of quinazoline derivatives which lack the amino acid residue of compounds of the CB3717-type. The disclosed compounds are reported to posses inhibitory activity against thymidylate synthase. Among the disclosed compounds are quinazoline derivatives wherein the amino acid residue of compounds of the CB3717-type is replaced by a residue derived from 5-aminotetrazole.

We have now found that the quinazoline derivatives of the present invention possess CB3717-type activity.

Antimetabolites, such as aminopterin and methotrexate, which are inhibitors of enzymes which utilise folic acid derivatives, have also shown promise in the treatment of various allergic diseases such as allergic rhinitis, atopic dermatitis and psoriasis. The quinazoline derivatives of the present invention, being antimetabolites of the CB3717-type, are thus of value as therapeutic agents in the treatment of, for example, allergic conditions such as psoriasis.

According to the invention there is provided a quinazoline of the formula I (set out hereinafter) wherein $R^1$ is hydrogen or amino, or alkyl or alkoxy each of up to 6 carbon atoms;

or $R^1$ is alkyl of up to 3 carbon atoms which bears a hydroxy substituent, or which bears one, two or three fluoro substituents;

or $R^1$ is hydroxyalkoxy of up to 3 carbon atoms or alkoxyalkoxy of up to 6 carbon atoms;

wherein the quinazoline ring may bear no further substituents or may bear one further substituent selected from halogeno and from alkyl and alkoxy each of up to 3 carbon atoms;

wherein $R^2$ is hydrogen, alkyl, alkenyl, alkynyl, hydroxyalkyl, halogenoalkyl or cyanoalkyl each of up to 6 carbon atoms;

wherein Ar is phenylene or heterocyclene which may be unsubstituted or may bear one or two substituents selected from halogeno, hydroxy, amino and nitro, and from alkyl, alkoxy and halogenoalkyl each of up to 3 carbon atoms;

wherein L is a group of the formula —CO.NH—, —NH.CO—, —CO.NR$^3$—, —NR$^3$.CO—, —CH=CH—, —CH$_2$O—, —OCH$_2$—, —CH$_2$S—, —SCH$_2$—, —CO.CH$_2$—, —CH$_2$.CO— or —CO.O—, wherein $R^3$ is alkyl of up to 6 carbon atoms; and wherein Y is aryl or a hydrogenated derivative thereof each of up to 10 carbon atoms, or heteroaryl or a hydrogenated derivative thereof; or Y is a group of the formula —A—Y$^1$ in which A is alkylene, cycloalkylene, alkenylene or alkynylene each of up to 6 carbon atoms, and Y$^1$ is aryl or a hydrogenated derivative thereof each of up to 10 carbon atoms, or heteroaryl or a hydrogenated derivative thereof;

wherein one constituent methylene group in A may be replaced by an oxy, thio, sulphinyl, sulphonyl or imino group or an alkylimino group of up to 6 carbon atoms;

and wherein each of said aryl or heteroaryl groups, or hydrogenated derivatives thereof, may be unsubstituted or may bear up to three substituents selected from hydroxy, oxo, amino, nitro, cyano, carbamoyl, sulphamoyl, carboxy and halogeno, from alkyl, alkylamino, dialkylamino, N-alkylcarbamoyl, N,N-dialkylcarbamoyl, alkoxycarbonyl, alkanoyloxyalkyl, alkylthio, alkylsulphinyl, alkylsulphonyl, alkoxy, halogenoalkyl, hydroxyalkyl, aminoalkyl, alkylaminoalkyl, dialkylaminoalkyl, carboxyalkyl, alkoxycarbonylalkyl, carbamoylalkyl, N-alkylcarbamoylalkyl and N,N-dialkylcarbamoylalkyl each of up to 6 carbon atoms and from phenyl, pyridyl and phenylalkyl of up to 10 carbon atoms, and wherein each of said phenyl or phenylalkyl groups may bear a substituent selected from halogeno and nitro, and from alkyl and alkoxy each of up to 3 carbon atoms;

or a pharmaceutically-acceptable salt thereof;

provided that when $R^1$ is hydrogen or amino, or alkyl of up to 6 carbon atoms, and L is a group of the formula —CONH—, then Y is not tetrazolyl.

The chemical formulae referred to herein by Roman numerals are set out for convenience on a separate sheet hereinafter. In this specification the term "alkyl" includes both straight and branched alkyl groups but references to individual alkyl groups such as "propyl" are specific for the straight chain version only. An analogous convention applies to other generic terms.

It will be observed that a quinazoline of the invention may possess one or more asymmetric carbon atoms e.g. when Y is a group of the formula —A—$Y^1$ in which A is branched-chain alkylene, and it can therefore exist in racemic and optically active forms. It is to be understood that this invention encompasses a racemic form of the quinazoline and any optically-active form thereof which possesses anti-tumour activity, it being a matter of common general knowledge how a racemic compound may be separated into its optically-active forms.

It will also be observed that a quinazoline of the invention of the formula I wherein L is a group of the formula —CH═CH— may exist as two geometric isomers. It is to be understood that this invention encompasses any geometric isomer which possesses anti-tumour activity, it being a matter of common general knowledge how geometric isomers may be separated.

Within the present invention it is to be understood that a quinazoline of the formula I may exhibit the phenomenon of tautomerism and that the formulae drawings presented within this specification can represent only one of the possible tautomeric forms. It is to be understood that the invention encompasses any tautomeric form which possesses anti-tumour activity and is not to be limited merely to any one tautomeric form utilised within the formulae drawings.

It is also to be understood that certain quinazolines of the formula I can exist in solvated as well as unsolvated forms such as, for example, hydrated forms. It is to be understood that the invention encompasses all such solvated forms which possess anti-tumour activity.

Suitable values for the generic radicals referred to herein include those set out below.

A suitable value for $R^1$, $R^2$ or $R^3$ when it is alkyl of up to 6 carbon atoms, or for an alkyl substituent of up to 6 carbon atoms which may be present as a substituent on an aryl or heteroaryl group, or a hydrogenated derivative thereof, is, for example, methyl, ethyl, propyl, isopropyl, butyl, isobutyl, sec-butyl, tert-butyl, pentyl, isopentyl, tert-pentyl, hexyl or isohexyl.

A suitable value for an alkyl substituent of up to 3 carbon atoms which may be present as a further substituent on the quinazoline ring, as a substituent on Ar, or as a substituent on a phenyl group is, for example, methyl, ethyl, propyl or isopropyl.

A suitable value for $R^2$ when it is alkenyl is, for example, prop-2-enyl, but-2-enyl, but-3-enyl or 2-methylprop-2-enyl; and when it is alkynyl is, for example prop-2-ynyl, but-2-ynyl or but-3-ynyl.

A suitable value for $R^1$ when it is alkoxy of up to 6 carbon atoms, or for an alkoxy substituent of up to 6 carbon atoms which may be present as a substitutent on an aryl or heteroaryl group, or a hydrogenated derivative thereof, is, for example, methoxy, ethoxy, propoxy, isopropoxy, butoxy, isobutoxy, pentyloxy or hexyloxy.

A suitable value for an alkoxy substituent of up to 3 carbon atoms which may be present as a further substituent on the quinazoline ring, as a substituent on Ar, or as a substituent on a phenyl group is, for example, methoxy, ethoxy, propoxy or isopropoxy.

A suitable value for an alkylthio substituent of up to 6 carbon atoms which may be present as a substituent on an aryl or heteroaryl group, or a hydrogenated derivative thereof, is, for example, methylthio, ethylthio, propylthio, isopropylthio, butylthio, isobutylthio, pentylthio or hexylthio.

A suitable value for a halogeno substituent which may be present as a further substituent on the quinazoline ring, as a substituent on Ar, as a substituent on an aryl or heteroaryl group, or a hydrogenated derivative thereof, or as a substituent on a phenyl group is, for example, fluoro, chloro, bromo or iodo.

A suitable value for $R^1$ when it is substituted alkyl is, for example, fluoromethyl, difluoromethyl, trifluoromethyl, 2-fluoroethyl, 3-fluoropropyl, hydroxymethyl, 2-hydroxyethyl or 3-hydroxypropyl.

A suitable value for $R^1$ when it is substituted alkoxy is, for example, 2-hydroxyethoxy, 2-methoxyethoxy, 3-methoxypropoxy or 2-ethoxyethoxy.

A suitable value for $R^2$ when it is hydroxyalkyl, halogenoalkyl and cyanoalkyl is, for example, 2-hydroxyethyl, 3-hydroxypropyl, 2-fluoroethyl, 2-chloroethyl, 2-bromoethyl, 3-fluoropropyl, 3-chloropropyl, cyanomethyl, 2-cyanoethyl or 3-cyanopropyl.

A suitable value for Ar when it is phenylene is, for example, 1,3-phenylene or 1,4-phenylene.

A suitable value for Ar when it is heterocyclene is, for example, a 5-membered or 6-membered aromatic (that is, fully unsaturated) heterocyclene diradical which contains up to 3 heteroatoms selected from the group consisting of oxygen, nitrogen and sulphur, for example, thienylene, pyridylene, pyrimidinylene, thiazolylene, oxazolylene or thiadiazolylene.

A suitable halogenoalkyl substituent in Ar is, for example, fluoromethyl, difluoromethyl or trifluoromethyl.

A suitable value for Y or $Y^1$ when it is aryl or a hydrogenated derivative thereof, is, for example, phenyl, cyclohexenyl, naphthyl, tetrahydronaphthyl, indenyl or indanyl, which may be attached through any available position and which may bear one or two substituents.

A suitable value for Y or $Y^1$ when it is heteroaryl or a hydrogenated derivative thereof, is, for example, a 5-membered or 6-membered heterocyclic radical which contains up to 4 heteroatoms selected from the group consisting of oxygen, nitrogen and sulphur, which heterocyclic radical is a single ring or is fused to a benzo ring, for example, furyl, benzofuranyl, tetrahydrofuryl, chromanyl, thienyl, pyridyl, N-oxidopyridyl, piperidinyl, quinolyl, isoquinolyl, pyrazinyl, pyrimidinyl, pyridazinyl, quinoxalinyl, quinazolinyl, cinnolinyl, pyrrolyl, pyrrolidinyl, indolyl, imidazolyl, benzimidazolyl, pyrazolyl, indazolyl, oxazolyl, isoxazolyl, thiazolyl, isothiazolyl, 1,2,3-triazolyl, 1,2,4-triazolyl, oxadiazolyl, furazanyl, thiadiazolyl, tetrazolyl or azepanyl, which may be attached through any available position including through any available nitrogen atom and which may bear up to three substituents including a substituent on any available nitrogen atom.

Particular values for Y and $Y^1$ when it is heteroaryl, or a hydrogenated derivative thereof, which bears up to three oxo substituents include for example, 1,2-dihydro-2-oxoquinolinyl (especially 1,2-dihydro-2-oxoquinolin-3-yl and 1,2-dihydro-2-oxoquinolin-6-yl), 3,4-dihydro-4-oxoquinazolinyl (especially 3,4-dihydro-4-oxoquinazolin-5-yl, 3,4-dihydro-4-oxoquinazolin-6-yl, 3,4-dihydro-4-oxoquinazolin-7-yl and 3,4-dihydro-4-oxoquinazolin-8-yl), 1,2-dihydro-2-oxopyridyl (especially 1,2-dihydro-2-oxopyrid-3-yl and 1,2-dihydro-2-oxopyrid-6-yl), 3,4-dihydro-4-oxopyrimidinyl (especially 3,4-dihydro-4-oxopyrimidin-2-yl and 3,4-dihydro-4-oxopyrimidin- 5-yl), 1,2,3,4-tetrahydro-2,4-dioxopyrimidinyl (especially 1,2,3,6-tetrahydro-2,6-dioxopyrimidin-4-yl and 1,2,3,4-tetrahydro-2,4-dioxopyrimidin-5-yl), 2,5-dioxopyrrolidinyl (especially 2,5-dioxopyrrolidin-3-yl), 2-oxopiperidinyl (especially 2-oxopiperidin-1-yl), 2,6-dioxopiperidinyl (especially 2,6-dioxopiperidin-3-yl) and 2-oxoazepanyl (especially hexahydro-2-oxoazepin-1-yl).

A suitable value for A when it is alkylene is, for example, methylene, ethylene, ethylidene, trimethylene, propylidene, propylene, isopropylidene, butylidene, isobutylidene, 1-ethylethylene, 1-propylethylene, 1-isopropylethylene, tetramethylene or pentamethylene; when it is alkenylene is, for example, 1-propenylene, 2-propenylene, 1-butenylene, 2-butenylene or 3-butenylene; and when it is alkynylene is, for example, 2-propynylene, 2-butynylene or 3-butynylene.

A suitable value for A when it is cycloalkylene is, for example, cyclopropylidene, 1,2-cyclopropylene, cyclopentylidene, 1,2-cyclopentylene, 1,3-cyclopentylene, cyclohexylidene, 1,2-cyclohexylene or 1,4-cyclohexylene.

A suitable value for a substituent which may be present on an aryl or heteroaryl group, or a hydrogenated derivative thereof, when it is alkylamino, dialkylamino, halogenoalkyl, alkylsulphinyl or alkylsulphonyl is, for example, methylamino, ethylamino, propylamino, isopropylamino, butylamino, pentylamino, hexylamino, dimethylamino, N-ethyl-N-methylamino, diethylamino, N-methyl-N-propylamino, N-methyl-N-isopropylamino, N-ethyl-N-isopropylamino, di-isopropylamino, fluoromethyl, difluoromethyl, trifluoromethyl, 2-fluoroethyl, 3-fluoropropyl, pentafluoroethyl, heptafluoropropyl, chloromethyl, dichloromethyl, methylsulphinyl, ethylsulphinyl, propylsulphinyl, isopropylsulphinyl, butylsulphinyl, methylsulphonyl, ethylsulphonyl, propylsulphonyl, isopropylsulphonyl or butylsulphonyl.

A suitable value for an alkylimino group which may replace one constituent methylene group in A is, for example, methylimino, ethylimino, propylimino or isopropylimino.

Suitable values for substituents which may be present on an aryl or heteroaryl group, or a hydrogenated derivative thereof, are, for example:

| | |
|---|---|
| for N-alkylcarbamoyl: | N-methylcarbamoyl, N-ethylcarbamoyl and N-propylcarbamoyl; |
| for N,N-dialkylcarbamoyl: | N,N-dimethylcarbamoyl; |
| for alkoxycarbonyl: | methoxycarbonyl, ethoxycarbonyl and tert-butoxycarbonyl; |
| for alkanoyloxyalkyl: | acetoxymethyl, propionyloxymethyl, isobutyryloxymethyl and pivaloyloxymethyl; |
| for hydroxyalkyl: | hydroxymethyl, 2-hydroxyethyl, 1-hydroxyethyl and 3-hydroxypropyl; |
| for aminoalkyl: | aminomethyl and 2-aminoethyl; |
| for alkylaminoalkyl: | methylaminomethyl, erhylaminomethyl and 2-methylaminoethyl; |
| for dialkylaminoalkyl: | dimethylaminomethyl, diethylaminomethyl, 2-dimethylaminoethyl and 2-diethyl-aminoethyl; |
| for carboxyalkyl: | carboxymethyl, 1-carboxyethyl, 2-carboxyethyl and 3-carboxypropyl; |
| for alkoxycarbonylalkyl: | methoxycarbonylmethyl, ethoxycarbonylmethyl, 2-methoxycarbonylethyl and 2-ethoxycarbonylethyl; |
| for carbamoylalkyl: | carbamoylmethyl, 2-carbamoylethyl and 3-carbamoylpropyl; |
| for N-alkylcarbamoylalkyl: | N-methylcarbamoylmethyl, N-ethylcarbamoylmethyl, 2-(N-methylcarbamoyl)-ethyl, 2-(N-ethylcarbamoyl)ethyl, 3-(N-methylcarbamoyl)propyl and 3-(N-ethylcarbamoyl)propyl; |
| for N,N-dialkylcarbamoylalkyl: | N,N-dimethylcarbanoylmethyl, N,N-diethylcarbanoylmethyl and 2-(N,N-dimethylcarbamoyl)ethyl; |
| for phenylalkyl: | benzyl, phenethyl, phenylpropyl and phenylbutyl. |

A suitable pharmaceutically-acceptable salt of a quinazoline of the invention which is sufficiently basic is an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a quinazoline of the invention which is sufficiently acidic (for example a quinazoline of the invention which contains a carboxy group) is an alkali metal salt, for example a sodium or potassium salt, an alkaline earth metal salt, for example a calcium or magnesium salt, an ammonium or tetra(2-hydroxyethyl)ammonium salt or a salt with an organic base which affords a physiologically-acceptable cation, for example a salt with methylamine, trimethylamine or tris(2-hydroxyethyl)amine.

A particular quinazoline of the invention has the formula I wherein $R^1$ is hydrogen or amino, or is alkyl (especially methyl, ethyl and isopropyl) or alkoxy (especially methoxy and ethoxy) each of up to 6 carbon atoms; or $R^1$ is alkyl of up to 3 carbon atoms which bears one, two or three fluoro substituents (especially fluoromethyl, difluoromethyl, trifluoromethyl, and 2-fluoroethyl);

wherein the quinazoline ring may bear no further substituent or may bear one further substituent selected from halogeno (especially fluoro, chloro and bromo) and from alkyl and alkoxy each of up to 3 carbon atoms (especially methyl and methoxy);

wherein $R^2$ is alkyl (especially methyl, ethyl and propyl), alkenyl (especially prop-2-enyl), alkynyl (especially prop-2-ynyl), hydroxyalkyl (especially 2-hydroxyethyl and 3-hydroxypropyl), halogenoalkyl (especially 2-fluoroethyl, 2-chloroethyl, 2-bromoethyl and 3-fluoropropyl) and cyanoalkyl (especially cyanomethyl and 2-cyanoethyl) each of up to 6 carbon atoms;

wherein Ar is phenylene (especially 1,4-phenylene) or heterocyclene (especially thienylene, pyridylene, pyrimidinylene, thiazolylene and thiadiazolylene) which is unsubstituted or which bears one or two substituents selected from halogeno (especially fluoro, chloro and bromo), hydroxy, amino and nitro, and alkyl (especially ,ethyl and ethyl), alkoxy (especially methoxy and ethoxy) and halogenoalkyl (especially fluoromethyl, difluoromethyl and trifluoromethyl) each of up to 3 carbon atoms;

wherein L is a group of the formula —CO.NH—, —CO.NR$^3$—, —CH$_2$O— or —CO.O—, wherein $R^3$ is alkyl (especially methyl and ethyl) of up to 6 carbon atoms; and wherein Y is aryl (especially phenyl and naphthyl) each of up to 10 carbon atoms, or heteroaryl or a hydrogenated derivative thereof (especially pyridyl, quinolyl, isoquinolyl, pyrimidinyl, imidazolyl, thiazolyl, 2,5-dioxopyrrolidinyl or 2,6-dioxopiperidinyl; or Y is a group of the formula —A—$Y^1$ in which A is alkylene (especially methylene, ethylene, ethylidene, trimethylene, propylidene, propylene, butylidene, isobutylidene, 1-isopropylethylene and tetramethylene) of up to 6 carbon atoms, and $Y^1$ is aryl or a hydrogenated derivative thereof (especially phenyl, naphthyl, tetrahydronaphthyl, indenyl and indanyl) each of up to 10 carbon atoms, or heteroaryl or a hydrogenated derivative thereof (especially furyl, thienyl, pyridyl, quinolyl, isoquinolyl, pyrazinyl, pyrimidinyl, pyridazinyl, quinoxalinyl, quinazolinyl, cinnolinyl, indolyl, imidazolyl, benzimidazolyl, pyrazolyl, indazolyl, oxazolyl, isoxazolyl, thiazolyl, isothiazolyl, 1,2,3-triazolyl, 1,2,4-triazolyl, thiadiazolyl, tetrazolyl and hexahydro-2-oxoazepinyl; wherein one constituent methylene group in A may be replaced by an oxy, thio, sulphinyl, sulphonyl or imino group; and wherein each of said aryl or heteroaryl groups, or hydrogenated derivatives thereof, may be unsubstituted or may bear up to three substituents selected from hydroxy, oxo, amino, nitro, cyano, carbamoyl, sulphamoyl, carboxy and halogeno (especially fluoro, chloro and bromo), and from alkyl (especially methyl and ethyl), alkylamino (especially methylamino and ethylamino), dialkylamino (especially dimethylamino and diethylamino), N-alkylcarbamoyl (especially N-methylcarbamoyl and N-ethylcarbamoyl), N,N-dialkylcarbamoyl (especially N,N-dimethylcarbamoyl and N,N-diethylcarbamoyl), alkoxycarbonyl (especially methoxycarbonyl, ethoxycarbonyl and tertbutoxycarbonyl), alkanoyloxyalkyl (especially isobutyryloxymethyl and pivaloyloxymethyl), alkylthio (especially methylthio and ethylthio), alkylsulphinyl (especially methylsulphinyl, ethylsulphinyl and isopropylsulphinyl), alkylsulphonyl (especially methylsulphonyl, ethylsulphonyl and isopropylsulphonyl), alkoxy (especially methoxy and ethoxy), halogenoalkyl (especially trifluoromethyl), carboxyalkyl (especially carboxymethyl, 1-carboxyethyl, 2-carboxyethyl and 3-carboxypropyl), alkoxycarbonylalkyl (especially methoxycarbonylmethyl and 2-methoxycarbonylethyl), carbamoylalkyl (especially carbamoylmethyl and 2-carbamoylethyl), N-alkylcarbamoylalkyl (especially N-methylcarbamoylmethyl and 2-(N-methylcarbamoyl)ethyl) and N,N-dialkylcarbamoylalkyl (especially N,N-dimethylcarbamoylmethyl and 2-(N,N-dimethylcarbamoyl)ethyl) each of up to 6 carbon atoms; and from phenyl, pyridyl and phenylalkyl (especially benzyl, phenethyl and phenylpropyl) of up to 10 carbon atoms, and wherein each of said phenyl or phenylalkyl groups may bear a substituent selected from halogeno (especially fluoro, chloro and bromo) and nitro, and from alkyl (especially methyl and ethyl) and alkoxy (especially methoxy and ethoxy) each up to 3 carbon atoms;

or a pharmaceutically-acceptable salt thereof.

A further particular quinazoline of the invention has the formula I wherein $R^1$ is hydrogen or amino, or methyl, ethyl, methoxy or fluoromethyl;

wherein the quinazoline ring may bear no further substituents or may bear one further substituent selected from fluoro, chloro, methyl and methoxy;

wherein $R^2$ is methyl, ethyl, propyl, prop-2-enyl, prop-2-ynyl, 2-hydroxyethyl, 3-hydroxypropyl, 2-fluoroethyl, 2-bromoethyl or cyanomethyl;

wherein Ar is 1,4-phenylene, thienylene, pyridylene, pyrimidinylene or thiazolylene which is unsubstituted or which bears a substituent selected from fluoro, chloro, bromo, hydroxy, amino, nitro, methyl, methoxy and trifluoromethyl;

wherein L is a group of the formula —CO.NH—, —CO.$NR^3$— or —CO.O—, wherein $R^3$ is methyl or ethyl; and Y is phenyl, 2,5-dioxopyrrolidinyl or 2,6-dioxopiperidinyl, or Y is a group of the formula —A—$Y^1$ in which A is methylene, ethylene, ethylidine, trimethylene, propylidene, propylene, butylidene, isobutylidene or tetramethylene and $Y^1$ is phenyl, furyl, thienyl, pyridyl, quinolyl, isoquinolyl, pyrazinyl, pyrimidinyl, quinazolinyl, pyridazinyl, indolyl, imidazolyl, benzimidazolyl, pyrazolyl, indazolyl, oxazolyl, isoxazolyl, thiazolyl, 1,2,3-triazolyl, 1,2,4-triazolyl, tetrazolyl or hexahydro-2-oxoazepin-1-yl;

wherein one constituent methylene group in A may be replaced by a thio, sulphinyl, sulphonyl or imino group; and wherein each of said phenyl or heteroaryl groups, or hydrogenated derivatives thereof, may be unsubstituted or may bear up to three substituents selected from hydroxy, oxo, amino, nitro, cyano, carbamoyl, sulphamoyl, carboxy, fluoro, chloro, bromo, methyl, ethyl, methylamino, ethylamino, dimethylamino, diethylamino, N-methylcarbamoyl, N-ethylcarbamoyl, N,N-dimethylcarbamoyl, N,N-diethylcarbamoyl, methoxycarbonyl, ethoxycarbonyl, tertbutoxycarbonyl, isobutyryloxymethyl, pivaloyloxymethyl, methylthio, ethylthio, methylsulphinyl, ethylsulphinyl, methylsulphonyl, ethylsulphonyl, methoxy, ethoxy, trifluoromethyl, carboxymethyl, 1-carboxyethyl, 2-carboxyethyl, 3-carboxypropyl, carbamoylmethyl, N-methylcarbamoylmethyl, N,N-dimethylcarbamoylmethyl, phenyl, pyridyl, benzyl, phenethyl or phenylpropyl, and wherein any phenyl group within said substituents may bear a substituent selected from fluoro, chloro, bromo, nitro, methyl, ethyl, methoxy and ethoxy;

or a pharmaceutically-acceptable salt thereof.

A preferred quinazoline of the invention has the formula I wherein $R^1$ is amino, methyl, methoxy or fluoromethyl;

wherein the quinazoline ring may bear no further substituents or may bear one further substituent selected from fluoro, chloro, methyl and methoxy;

wherein $R^2$ is methyl, ethyl, prop-2-enyl or prop-2-ynyl;

wherein Ar is 1,4-phenylene, thienylene, pyridylene or thiazolylene which is unsubstituted or which bears a fluoro or nitro substituent;

wherein L is a group of the formula —CO.NH— or —CO.O—; and

Y is phenyl, or Y is a group of the formula —A—$Y^1$ in which A is methylene, ethylene, ethylidene, trimethylene, propylidene, propylene or isobutylidene and $Y^1$ is phenyl, 2-thienyl, 2-pyridyl, 3-pyridyl, 4-pyridyl, 3-quinolyl, 4-quinolyl, 8-quinolyl, 2-pyrimidinyl, 4-pyrimidinyl, 6-quinazolinyl, 3-indolyl, 1-imidazolyl, 2-imidazolyl, 4-imidazolyl, 2-benzimidazolyl, 2-thiazolyl, 5-thiazolyl, 1,2,4-triazol-1-yl, 1,2,4-triazol-3-yl or tetrazol-5-yl, or Y is phenylsulphonyl; and wherein each of said phenyl or heteroaryl groups may be unsubstituted or may bear up to three substituents selected from hydroxy, oxo, amino, nitro, cyano, carbamoyl, carboxy, fluoro, chloro, methyl, ethyl, N-methylcarbamoyl, N,N-dimethylcarbamoyl, methoxycarbonyl, ethoxycarbonyl, pivaloyloxymethyl, methoxy, trifluoromethyl, carboxymethyl, 1-carboxyethyl, 2-carboxyethyl, 3-carboxypropyl, 4-pyridyl and benzyl;

or a pharmaceutically-acceptable salt thereof.

An especially preferred quinazoline of the invention has the formula I wherein $R^1$ is amino, methyl or methoxy;

wherein the quinazoline ring may bear a methyl substituent in the 7-position;

wherein $R^2$ is methyl, ethyl or prop-2-ynyl;

wherein Ar is 1,4-phenylene or thien-2,5-diyl, or is pyrid-2,5-diyl with the group —L—Y in the 2-position, or is 2-fluoro-1,4-phenylene with the group —L—Y in the 1-position;

wherein L is a group of the formula —CONH—;

and wherein Y is benzyl or phenylsulphonyl which may bear a nitro, cyano, carboxy or trifluoromethyl substituent, or Y is thiazol-5-ylmethyl or 1,2,3,6-tetrahydro-2,6-dioxopyrimidin-4-ylmethyl, or Y is 2,3-dihydro-4-oxoquinazolin-6-ylmethyl which may bear one or two methyl substituents;

or a pharmaceutically-acceptable salt thereof;

A further especially preferred quinazoline of the invention has the formula I wherein $R^1$ is methyl;

wherein the quinazoline ring may bear a methyl substituent in the 7-position;

wherein $R^2$ is methyl or prop-2-ynyl; wherein Ar is 1,4-phenylene, or 2-fluoro-1,4-phenylene with the group —L—Y in the 1-position;

wherein L is a group of the formula —CO.NH—; and Y is a group of the formula —A—$Y^1$ in which A is methylene and $Y^1$ is 2-nitrophenyl, 3-nitrophenyl, 3-cyanophenyl, 4-carboxyphenyl or 3-trifluoromethylphenyl, or $Y^1$ is 5-thiazolyl, 2,3-dihydro-4-oxoquinazolin-6-yl, 2,3-dihydro-2-methyl-4-oxoquinazolin-6-yl or 2,3-dihydro-2,3-dimethyl-4-oxoquinazolin-6-yl;

or a pharmaceutically-acceptable salt thereof.

Specific preferred quinazolines of the invention form the group of compounds:

p-[N-(3,4-dihydro-2-methyl-4-oxoquinazolin-6-ylmethyl)-N-(prop-2-ynyl)amino]-N-(3,4-dihydro-2-methyl-4-oxoquinazolin-6-ylmethyl)benzamide;

p-[N-(3,4-dihydro-2-methyl-4-oxoquinazolin-6-ylmethyl)-N-(prop-2-ynyl)amino]-N-(3-trifluoromethylbenzyl)benzamide;

p-[N-(3,4-dihydro-2-methyl-4-oxoquinazolin-6-ylmethyl)-N-(prop-2-ynyl)amino]-N-(2-nitrobenzyl)benzamide;

p-[N-(3,4-dihydro-2-methyl-4-oxoquinazolin-6-ylmethyl)-N-methylamino]-o-fluoro-N-(3-nitrobenzyl)benzamide;

5-[N-(3,4-dihydro-2-methyl-4-oxoquinazolin-6-ylmethyl)-N-(prop-2-ynyl)amino]-N-(3-nitrobenzyl)pyridine-2-carboxamide;

p-[N-(3,4-dihydro-2-methoxy-4-oxoquinazolin-6-ylmethyl)-N-(prop-2-ynyl)amino]-N-(3-nitrobenzyl)benzamide;

p-[N-(2-amino-3,4-dihydro-4-oxoquinazolin-6-ylmethyl)-N-(prop-2-ynyl)amino]-N-(3-nitrobenzyl)benzamide;

p-[N-(3,4-dihydro-2-methyl-4-oxoquinazolin-6-ylmethyl)-N-(prop-2-ynyl)amino]-N-(3-cyanobenzyl)benzamide and p-[N-(3,4-dihydro-2,7-dimethyl-4-oxoquinazolin-6-ylmethyl)-N-(prop-2-ynyl)amino]-N-(3-nitrobenzyl)benzamide;

or a pharmaceutically-acceptable salt thereof.

According to a further feature of the present invention there is provided a quinazoline of the formula I (set out hereinafter)

wherein $R^1$ is alkyl or alkoxy each of up to 6 carbon atoms;

or $R^1$ is alkyl of up to 3 carbon atoms which bears a hydroxy substituent, or which bears one, two or three fluoro substituents;

or $R^1$ is hydroxyalkoxy of up to 3 carbon atoms or alkoxyalkoxy of up to 6 carbon atoms;

wherein the quinazoline ring may bear no further substituents or may bear one further substituent selected from halogeno and from alkyl and alkoxy each of up to 3 carbon atoms;

wherein $R^2$ is hydrogen, alkyl, alkenyl, alkynyl, hydroxyalkyl, halogenoalkyl or cyanoalkyl each of up to 6 carbon atoms;

wherein Ar is phenylene or heterocyclene which may be unsubstituted or may bear one or two substituents selected from halogeno, hydroxy and amino, and from alkyl, alkoxy and halogenoalkyl each of up to 3 carbon atoms;

wherein L is a group of the formula —CO.NH—, —NH.CO—, —CO.$NR^3$—, —$NR^3$.CO—, —CH=CH—, —CH$_2$O—, —OCH$_2$—, —CH$_2$S—, —SCH$_2$—, —CO.CH$_2$—, —CH$_2$.CO— or —CO.O—, wherein $R^3$ is alkyl of up to 6 carbon atoms; and wherein Y is aryl or a hydrogenated derivative thereof each of up to 10 carbon atoms, or heteroaryl or a hydrogenated derivative thereof; or Y is a group of the formula —A—$Y^1$ in which A is alkylene, cycloalkylene, alkenylene or alkynylene each of up to 6 carbon atoms, and $Y^1$ is aryl or a hydrogenated derivative thereof each of up to 10 carbon atoms, or heteroaryl or a hydrogenated derivative thereof;

wherein one constituent methylene group in A may be replaced by an oxy, thio, sulphinyl, sulphonyl or imino group or an alkylimino group of up to 6 carbon atoms;

and wherein each of said aryl or heteroaryl groups, or hydrogenated derivatives thereof, may be unsubstituted or may bear one or two substituents selected from hydroxy, amino, nitro, cyano, carbamoyl, carboxy and halogeno, from alkyl, alkylamino, dialkylamino, N-alkylcarbamoyl, N,N-dialkylcarbamoyl, alkoxycarbonyl, alkylthio, alkylsulphinyl, alkylsulphonyl, alkoxy, halogenoalkyl, hydroxyalkyl, aminoalkyl, alkylaminoalkyl, dialkylaminoalkyl, carboxyalkyl, alkoxycarbonylalkyl, carbamoylalkyl, N-alkylcarbamoylalkyl and N,N-dialkylcarbamoylalkyl each of up to 6 carbon atoms and from phenyl and phenylalkyl of up to 10 carbon atoms, and wherein each of said phenyl groups may bear a substituent selected from halogeno and from alkyl and alkoxy each of up to 3 carbon atoms;

or a pharmaceutically-acceptable salt thereof;

provided that when $R^1$ is alkyl of up to 6 carbon atoms, the quinazoline ring bears no further substituents or bears one further substituent selected from halogeno and alkyl of up to 3 carbon atoms, $R^2$ is alkyl, alkenyl or alkynyl each of up to 6 carbon atoms, Ar is phenylene which is unsubstituted or bears one or two substituents selected from halogeno, hydroxy and amino, and L is a group of the formula —CONH—, then Y is not tetrazol-5-yl.

A suitable value for Y or $Y^1$ when it is heteroaryl, or a hydrogenated derivative thereof, within the quinazoline of the formula I as defined immediately above, is, for example, a 5-membered or 6-membered heterocyclic radical which contains up to 4 heteroatoms selected from the group consisting of oxygen, nitrogen and sulphur, for example, furyl, benzofuranyl, tetrahydrofuryl, chromanyl, thienyl, pyridyl, quinolyl, isoquinolyl, pyrazinyl, pyrimidinyl, pyridazinyl, pyrrolyl, indolyl, imidazolyl, benzimidazolyl, pyrazolyl, indazolyl, oxazolyl, isoxazolyl, thiazolyl, isothiazolyl, 1,2,3-triazolyl, 1,2,4-triazolyl, oxadiazolyl, furazanyl, thiadiazolyl or tetrazolyl, which may be attached through any available position including through any available nitrogen atom and which may bear one or two substituents including a substituent on any available nitrogen atom.

A further particular quinazoline of the invention has the formula I wherein $R^1$ is alkyl (especially methyl, ethyl and isopropyl) or alkoxy (especially methoxy and ethoxy) each of up to 6 carbon atoms; or $R^1$ is alkyl of up to 3 carbon atoms which bears a hydroxy substituent or which bears one, two or three fluoro substituents (especially fluoromethyl, difluoromethyl, trifluoromethyl, 2-fluoroethyl, hydroxymethyl and 2-hydroxyethyl); or $R^1$ is hydroxyalkoxy of up to 3 carbon atoms or alkoxyalkoxy of up to 6 carbon atoms (especially 2-hydroxyethoxy, 2-methoxyethoxy and 2-ethoxyethoxy);

wherein the quinazoline ring may bear no further substituent or may bear one further substituent selected from halogeno (especially fluoro, chloro and bromo) and from alkyl and alkoxy each of up to 3 carbon atoms (especially methyl and methoxy);

wherein $R^2$ is hydrogen, alkyl (especially methyl, ethyl and propyl), alkenyl (especially prop-2-enyl), alkynyl (especially prop-2-ynyl), hydroxyalkyl (especially 2-hydroxyethyl and 3-hydroxypropyl), halogenoalkyl (especially 2-fluoroethyl, 2-chloroethyl, 2-bromoethyl and 3-fluoropropyl) and cyanoalkyl (especially cyanomethyl and 2-cyanoethyl) each of up to 6 carbon atoms;

wherein Ar is phenylene (especially 1,4-phenylene) or heterocyclene (especially thienylene, pyridylene, pyrimidinylene, thiazolylene, oxazolylene and thiadiazolylene) which is unsubstituted or which bears one or two substituents selected from halogeno (especially fluoro, chloro and bromo), hydroxy and amino and alkyl (especially methyl and ethyl), alkoxy (especially methoxy and ethoxy) and halogenoalkyl (especially fluoromethyl, difluoromethyl and trifluoromethyl) each of up to 3 carbon atoms;

wherein L is a group of the formula —CO.NH—, —NH.CO—, —CO.NR$^3$—, —NR$^3$.CO—, —CH=CH—, —CH$_2$O—, —OCH$_2$—, —CO.CH$_2$—, —CH$_2$.CO— or —CO.O—, wherein $R^3$ is alkyl (especially methyl and ethyl) of up to 6 carbon atoms; and wherein Y is aryl or a hydrogenated derivative thereof (especially phenyl, cyclohexenyl, naphthyl, tetrahydronaphthyl, indenyl and indanyl) each of up to 10 carbon atoms, or heteroaryl or a hydrogenated derivative thereof (especially furyl, benzofuranyl, thienyl, pyridyl, quinolyl, isoquinolyl, pyrazinyl, pyrimidinyl, pyridazinyl, indolyl, imidazolyl, benzimidazolyl, pyrazolyl, indazolyl, oxazolyl, thiazolyl, 1,2,3-triazolyl, 1,2,4-triazolyl, oxadiazolyl, thiadiazolyl and tetrazolyl); or Y is a group of the formula —A—$Y^1$ in which A is alkylene (especially methylene, ethylene, ethylidene, trimethylene, propylidene, propylene, 1-isopropylethylene and tetramethylene) or cycloalkylene (especially cyclopentylidene, 1,2-cyclopentylene, 1,2-cyclohexylene and 1,4-cyclohexylene) each of up to 6 carbon atoms, and $Y^1$ is aryl or a hydrogenated derivative thereof (especially phenyl, naphthyl, tetrahydronaphthyl, indenyl and indanyl) each of up to 10 carbon atoms, or heteroaryl or a hydrogenated derivative thereof (especially pyridyl, quinolyl, isoquinolyl, pyrazinyl, pyrimidinyl, pyridazinyl, indolyl, imidazolyl, benzimidazolyl, pyrazolyl, indazolyl, oxazolyl, thiazolyl, 1,2,3-triazolyl, 1,2,4-triazolyl, thiadiazolyl and tetrazolyl);

wherein one constituent methylene group in A may be replaced by an oxy, thio, sulphinyl or sulphonyl group; and wherein each of said aryl or heteroaryl groups, or hydrogenated derivatives thereof, may be unsubstituted or may bear one or two substituents selected from hydroxy, amino, nitro, cyano, carbamoyl, carboxy and halogeno (especially fluoro, chloro and bromo), and from alkyl (especially methyl and ethyl), alkylamino (especially methylamino and ethylamino), dialkylamino (especially dimethylamino and diethylamino), N-alkylcarbamoyl (especially N-methylcarbamoyl and N-ethylcarbamoyl), N,N-dialkylcarbamoyl (especially N,N-dimethylcarbamoyl and N,N-diethylcarbamoyl), alkoxycarbonyl (especially methoxycarbonyl, ethoxycarbonyl and tert-butoxycarbonyl), alkylthio (especially methylthio and ethylthio), alkylsulphinyl (especially methylsulphinyl, ethylsulphinyl and isopropylsulphinyl), alkylsulphonyl (especially methylsulphonyl, ethylsulphonyl and isopropylsulphonyl), alkoxy (especially methoxy and ethoxy), halogenoalkyl (especially trifluoromethyl), hydroxyalkyl (especially hydroxymethyl and 2-hydroxyethyl), aminoalkyl (especially aminomethyl), carboxyalkyl (especially carboxymethyl and 2-carboxyethyl), alkoxycarbonylalkyl (especially methoxycarbonylmethyl and 2-methoxycarbonylethyl), carbamoylalkyl (especially carbamoylmethyl and 2-carbamoylethyl), N-alkylcarbamoylalkyl (especially N-methylcarbamoylmethyl and 2-(N-methylcarbamoyl)ethyl) and N,N-dialkylcarbamoylalkyl (especially N,N-dimethylcarbamoylmethyl and 2-(N,N-dimethylcarbamoyl)ethyl) each of up to 6 carbon atoms; and from phenyl and phenylalkyl (especially benzyl, phenethyl and phenylpropyl) of up to 10 carbon atoms, and wherein each of said phenyl groups may bear a substituent selected from halogeno (especially fluoro, chloro and bromo) and from alkyl (especially methyl and ethyl) and alkoxy (especially methoxy and ethoxy) each of up to 3 carbon atoms;

or a pharmaceutically-acceptable salt thereof.

provided that when $R^1$ is alkyl of up to 6 carbon atoms, the quinazoline ring bears no further substituents or bears one further substituent selected from halogeno and alkyl of up to 3 carbon atoms, $R^2$ is alkyl, alkenyl or alkynyl each of up to 6 carbon atoms, Ar is phenylene which is unsubstituted or bears one or two substituents selected from halogeno, hydroxy and amino, and L is a group of the formula —CONH—, then Y is not tetrazol-5-yl.

A further preferred quinazoline of the invention has the formula I
wherein $R^1$ is methyl, ethyl, methoxy or fluoromethyl;
wherein the quinazoline ring may bear no further substituents or may bear one further substituent selected from fluoro, chloro, methyl and methoxy;
wherein $R^2$ is hydrogen, methyl, ethyl, propyl, prop-2-enyl, prop-2-ynyl, 2-hydroxyethyl, 3-hydroxypropyl, 2-fluoroethyl, 2-bromoethyl or cyanomethyl;
wherein Ar is 1,4-phenylene, thienylene, pyridylene, pyrimidinylene, thiazolylene or thiadiazolylene which is unsubstituted or which bears one or two substituents selected from fluoro, chloro, bromo, hydroxy, amino, methyl, methoxy and trifluoromethyl;
wherein L is a group of the formula —CO.NH—, —NH.CO—, —CO.NR$^3$—, —NR$^3$.CO—, —CH=CH—, —CH$_2$O—, —CO.CH$_2$— or —CO.O—,
wherein $R^3$ is methyl or ethyl; and
Y is phenyl, naphthyl, tetrahydronaphthyl, pyridyl, quinolyl, isoquinolyl, pyrimidinyl, indolyl, imidazolyl, benzimidazolyl, pyrazolyl, indazolyl, oxazolyl, thiazolyl, 1,2,3-triazolyl, 1,2,4-triazolyl, thiadiazolyl or tetrazolyl; or
Y is a group of the formula —A—Y$^1$ in which A is methylene, ethylene, ethylidene, trimethylene, propylidene, propylene, 1-isopropylethylene or tetramethylene and Y$^1$ is phenyl, naphthyl, tetrahydronaphthyl, indenyl, indanyl, pyridyl, quinolyl, isoquinolyl, pyrazinyl, pyrimidinyl, pyridazinyl, indolyl, imidazolyl, benzimidazolyl, pyrazolyl, indazolyl, oxazolyl, thiazolyl, 1,2,3-triazolyl, 1,2,4-triazolyl, thiadiazolyl or tetrazolyl;
wherein one constituent methylene group in A may be replaced by an oxy, thio, sulphinyl or sulphonyl group; and
wherein each of said aryl or heteroaryl groups, or hydrogenated derivatives thereof, may be unsubstituted or may bear one or two substituents selected from hydroxy, amino, nitro, cyano, carbamoyl, carboxy, fluoro, chloro, bromo, methyl, ethyl, methylamino, ethylamino, dimethylamino, diethylamino, N-methylcarbamoyl, N-ethylcarbamoyl, N,N-dimethylcarbamoyl, N,N-diethylcarbamoyl, methoxycarbonyl, ethoxycarbonyl, tert-butoxycarbonyl, methylthio, ethylthio, methylsulphinyl, ethylsulphinyl, isopropylsulphinyl, methylsulphonyl, ethylsulphonyl, isopropylsulphonyl, methoxy, ethoxy, trifluoromethyl, carboxymethyl, 2-carboxyethyl, carbamoylmethyl, N-methylcarbamoylmethyl, N,N-dimethylcarbamoylmethyl, phenyl, benzyl, phenethyl or phenylpropyl, and wherein each of said phenyl groups may bear a substituent selected from fluoro, chloro, bromo, methyl, ethyl, methoxy and ethoxy;
or a pharmaceutically acceptable salt thereof;
provided that when $R^1$ is methyl or ethyl, the quinazoline ring bears no further substituents or bears one further substituent selected from fluoro, chloro and methyl, $R^2$ is methyl, ethyl, propyl, prop-2-enyl or prop-2-ynyl, Ar is 1,4-phenylene which is unsubstituted or bears one or two substituents selected from fluoro, chloro, bromo, hydroxy and amino, and L is a group of the formula —CONH—, then Y is not tetrazol-5-yl.

A further especially preferred quinazoline of the invention has the formula I
wherein $R^1$ is methyl, ethyl, methoxy or fluoromethyl;
wherein the quinazoline ring may bear no further substituents or may bear one further substituent selected from fluoro, chloro, methyl and methoxy;
wherein $R^2$ is hydrogen, methyl, ethyl, propyl, prop-2-enyl, prop-2-ynyl, 2-hydroxyethyl, 3-hydroxypropyl, 2-fluoroethyl, 2-bromoethyl or cyanomethyl;
wherein Ar is 1,4-phenylene, thien-2,5-diyl, pyrid-2,5-diyl or thiazol-2,5-diyl which is unsubstituted or which bears one or two substituents selected from fluoro, chloro, hydroxy, amino and methyl;
wherein L is a group of the formula —CO.NH—, —CO.NR$^3$— or —CO.O—,
wherein $R^3$ is methyl or ethyl; and
Y is phenyl, pyridyl, pyrimidinyl, imidazolyl, thiazolyl or 1,2,3-triazolyl; or
Y is a group of the formula —A—Y$^1$ in which A is methylene, ethylene, ethylidene or trimethylene and Y$^1$ is phenyl, naphthyl, pyridyl, quinolyl, isoquinolyl, pyrimidinyl, indolyl, imidazolyl, benzimidazolyl, pyrazolyl, indazolyl, thiazolyl, 1,2,3-triazolyl, 1,2,4-triazolyl, thiadiazolyl or tetrazolyl; and
wherein each of said aryl or heteroaryl groups may be unsubstituted or may bear one or two substituents selected from amino, nitro, fluoro, methyl, carbamoyl, N-methylcarbamoyl, N,N-dimethylcarbamoyl, methoxycarbonyl, ethoxycarbonyl, methylsulphinyl, methylsulphonyl, methoxy, trifluoromethyl or benzyl;
or a pharmaceutically-acceptable salt thereof.

A further especially preferred quinazoline of the invention has the formula I
wherein $R^1$ is methyl; wherein $R^2$ is hydrogen, methyl, ethyl, prop-2-ynyl or 2-fluoroethyl;
wherein Ar is 1,4-phenylene or thien-2,5-diyl, or is pyrid-2,5-diyl or thiazol-2,5-diyl each with the group —L—Y in the 2-position, or is 2-fluoro-1,4-phenylene with the group —L—Y in the 1-position;
wherein L is a group of the formula —CO.NH—, —CO.NR$^3$— or —CO.O—,
wherein $R^3$ is methyl or ethyl; and
wherein Y is phenyl; or
Y is a group of the formula —A—Y$^1$ in which A is methylene, ethylene, ethylidene or trimethylene and Y$^1$ is phenyl, 2-pyridyl, 3-pyridyl, 4-pyridyl, 1-isoquinolyl, 3-isoquinolyl, 4-isoquinolyl, 2-pyrimidinyl, 4-pyrimidinyl, 5-pyrimidinyl, 2-indolyl, 3-indolyl, 1-imidazolyl, 2-imidazolyl, 2-benzimidazolyl, 1-pyrazolyl, 3-pyrazolyl, 4-pyrazolyl, 3-indazolyl, 2-thiazolyl, 4-thiazolyl, 5-thiazolyl, 1,2,3-triazol-4-yl, 1,2,4-triazol-3-yl, 1,2,4-triazol-4-yl, 1,2,4-triazol-1-yl, 2-thiadiazolyl or 5-tetrazolyl; and
wherein each of said aryl or heteroaryl groups may be unsubstituted or may bear one or two substituents selected from amino, nitro, carbamoyl, fluoro, methyl, ethoxycarbonyl, methylsulphinyl, methylsulphonyl, methoxy, trifluoromethyl or benzyl;
or a pharmaceutically-acceptable salt thereof.

A further especially preferred quinazoline of the invention has the formula I
wherein $R^1$ is methyl; wherein $R^2$ is methyl, ethyl or prop-2-ynyl; wherein Ar is 1,4-phenylene or thien-2,5-diyl, or is pyrid-2,5-diyl or thiazol-2,5-diyl each with the group —L—Y in the 2-position, or is 2-fluoro-1,4-phenylene with the group —L—Y in the 1-position;
wherein L is a group of the formula —CO.NH— and
Y is a group of the formula —A—Y$^1$ in which A is methylene or ethylene and Y$^1$ is 2-pyridyl, 3-pyridyl, 4-pyridyl, 3-indolyl or 1,2,4-triazol-1-yl, or $Y^1$ is phenyl which may be unsubstituted or may bear a substituent selected from amino, nitro, ethoxycarbonyl or trifluoromethyl;

or a pharmaceutically-acceptable salt thereof.

Further specific preferred quinazolines of the invention form the group of compounds:

N-benzyl-p-[N-(3,4-dihydro-2-methyl-4-oxoquinazolin-6-ylmethyl)-N-(prop-2-ynyl)amino]benzamide;

p-[N-(3,4-dihydro-2-methyl-4-oxoquinazolin-6-ylmethyl)-N-(prop-2-ynyl)amino]-N-(m-nitrobenzyl)benzamide;

p-[N-(3,4-dihydro-2-methyl-4-oxoquinazolin-6-ylmethyl)-N-(prop-2-ynyl)amino]-N-(2-pyridylmethyl)benzamide;

p-[N-(3,4-dihydro-2-methyl-4-oxoquinazolin-6-ylmethyl)-N-(prop-2-ynyl)amino]-N-(3-pyridylmethyl)benzamide and N-benzylimidazol-2-ylmethyl p-[N-(3,4-dihydro-2-methyl-4-oxoquinazolin-6-ylmethyl)-N-ethylamino]benzoate.

A quinazoline of the invention, or a pharmaceutically-acceptable salt thereof, may be prepared by any process known to be applicable to the preparation of chemically-related compounds.

Such processes are provided as a further feature of the invention and are illustrated by the following representative examples, processes (a) to (f).

(a) A preferred process for the manufacture of a quinazoline of the invention comprises the reaction of a compound of the formula II (set out hereinafter) wherein $R^1$ has the meaning stated above, provided that when $R^1$ is amino, hydroxyalkyl or hydroxyalkoxy any amino or hydroxy group is protected by a conventional protecting group, $R^4$ is hydrogen or a protecting group and Z is a displaceable group, with a compound of the formula:

HNR$^2$—Ar—L—Y wherein $R^2$, Ar, L and Y have the meanings stated above, provided that when there is an amino, alkylamino, imino, hydroxy or carboxy group in $R^2$, Ar or Y, any amino, alkylamino, imino and carboxy group is protected by a conventional protecting group and any hydroxy group may be protected by a conventional protecting group or alternatively any hydroxy group need not be protected; whereafter any undesired protecting group in $R^1$, $R^2$, Ar and Y is removed.

The reaction is preferably carried out in the presence of a suitable base such as, for example, an alkali or alkaline earth metal carbonate or hydroxide, for example sodium carbonate, potassium carbonate, calcium carbonate, sodium hydroxide or potassium hydroxide, or, for example, an organic amine base such as, for example, pyridine, lutidine, collidine, 4-dimethylaminopyridine, triethylamine, morpholine or diazabicyclo[5.4.0]undec-7-ene. The reaction is preferably carried out in a suitable inert solution or diluent, for example dimethylformamide, dimethylacetamide, N-methylpyrrolidin-2-one or dimethylsulphoxide and at a temperature in the range, for example, 25° to 150° C., conveniently at or near 80° C.

A suitable protecting group for a hydroxy group may be, for example, an esterifying group, for example an acetyl or benzoyl group, which may be removed by hydrolysis with a base, for example sodium hydroxide, or provided that $R^2$, L and Y do not contain an alkenyl or alkynyl group, the protecting group may be, for example, an α-arylalkyl group, for example a benzyl group, which may be removed by hydrogenation over a catalyst, for example palladium-on-charcoal.

A suitable protecting group for an amino, alkylamino or imino group may be, for example, an alkoxycarbonyl group, for example a tert-butyloxycarbonyl group which may be removed by treatment with an organic acid, for example trifluoroacetic acid; or it may be, for example, a benzyloxycarbonyl group which may be removed by treatment with a Lewis acid, for example boron tris(trifluoroacetate).

A suitable alternative protecting group for a primary amino group is, for example, a phthaloyl group which may be removed by treatment with an alkylamine, for example dimethylaminopropylamine, or with hydrazine.

A suitable protecting group for a carboxy group may be an esterifying group, for example a methyl or an ethyl group which may be removed by hydrolysis with a base, for example sodium hydroxide; or, for example a tert-butyl group which may be removed by treatment with an organic acid, for example trifluoroacetic acid.

A suitable value for $R^4$ when it is a protecting group is, for example, a pivaloyloxymethyl group which may be removed by hydrolysis with a base, for example sodium hydroxide.

Z may be, for example, a halogeno or sulphonyloxy group, for example a chloro, bromo, methanesulphonyloxy or toluene-p-sulphonyloxy group.

The compound of the formula:

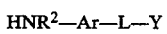

HNR$^2$—Ar—L—Y wherein L is a group of the formula —CONH— or —CONR$^3$— wherein $R^3$ has the meanings stated above, used as a starting material above, may be obtained by the reaction of an acid of the formula O$_2$N—Ar—CO$_2$H, or a reactive derivative thereof, wherein Ar has the meaning stated above with an amine of the formula H$_2$N—Y or R$^3$NH—Y wherein $R^3$ and Y have the meanings stated above and any amino, alkylamino, imino and carboxy group in Ar and Y is protected by a conventional protecting group as stated above and any hydroxy group in Ar and Y may be protected by a conventional protecting group as stated above or alternatively any hydroxy group need not be protected. Thereafter the nitro group may be reduced by conventional means to an amino group which in turn may be alkylated with a compound of the formula $R^2$—Z wherein $R^2$ and Z have the meanings stated above.

A suitable reactive derivative of an acid of the formula given above may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide, for example dicyclohexylcarbodiimide.

The compound of the formula:

$HNR^2-Ar-L-Y$ wherein L is a group of the formula —NH.CO— or —$NR^3$.CO— wherein $R^3$ has the meaning stated above, used as a starting material above, may be obtained by the reaction of an amine of the formula $HNR^2-Ar-NH_2$, wherein Ar has the meaning stated above with an acid of the formula $HO_2C-Y$, or a reactive derivative thereof, wherein Y has the meaning stated above and any amino, alkylamino, imino and carboxy group in Ar and Y is protected by a conventional protecting group as stated above and any hydroxy group in Ar and Y may be protected by a conventional protecting group as stated above or alternatively any hydroxy group need not be protected.

The compound of the formula:

$HNR^2-Ar-L-Y$ wherein L is a group of the formula —CH=CH—, used as a starting material above, may be obtained by the reaction of an aldehyde of the formula $HNG^1-Ar-CHO$ wherein Ar has the meaning stated above and $G^1$ is a conventional protecting group for an amino group as stated above, for example an alkoxycarbonyl group, with a triphenylphosphonium salt of the formula:

$(Ph)_3P^+-CH_2-Y\ Z^-$ wherein Y has the meaning stated above and wherein $Z^-$ is an anion, for example the bromide ion, and any amino, alkylamino and imino group in Ar and Y is protected by a conventional protecting group as stated above and any hydroxy and carboxy group in Ar and Y may be protected by a conventional protecting group as stated above or alternatively any hydroxy and carboxy group need not be protected.

The reaction may be carried out in solution in dimethyl sulphoxide in the presence of dimsyl sodium. Thereafter the protecting group $G^1$ may be removed by conventional means and whereafter the amine of the formula:

$H_2N-Ar-CH=CH-Y$ may be alkylated with a compound of the formula $R^2-Z$ wherein $R^2$ and Z have the meanings stated above.

The protecting group $G^1$ may be chosen such that it may be removed while the conventional protecting group on any amino, alkylamino and imino group in Ar and Y remains intact.

The triphenylphosphonium salt of the formula:

$(Ph)_3P^+-CH_2Y\ Z^-$ used as a starting material above may be obtained by the reaction of triphenylphosphine with a compound of the formula $Y-CH_2-Z$ wherein Y and Z have the meanings stated above.

Alternatively the compound of the formula:

$HNR^2-Ar-L-Y$ wherein L is a group of the formula —CH=CH—, used as a starting material above, may be obtained by the reaction of an aldehyde of the formula $O_2N-Ar-CHO$ wherein Ar has the meaning stated above with a triphenylphosphonium salt of the formula:

$(Ph)_3P^+-CH_2-Y\ Z^-$ wherein Y and $Z^-$ have the meanings stated above and any amino, alkylamino and imino group in Ar and Y is protected by a conventional protecting group as stated above and any hydroxy and carboxy group in Ar and Y may be protected by a conventional protecting group as stated above or alternatively and hydroxy and carboxy group need not be protected.

The reaction may be carried out in solution in dimethylsulphoxide in the presence of dimsyl sodium. Thereafter the nitro group may be reduced by conventional means to an amino group which in turn may be alkylated with a compound of the formula $R^2-Z$ wherein $R^2$ and Z have the meanings stated above.

The compound of the formula:

$HNR^2-Ar-L-Y$ wherein L is a group of the formula —$CH_2O$—, used as a starting material above, may be obtained by the reaction of an alcohol of the formula $O_2N-Ar-CH_2OH$ wherein Ar has the meaning stated above with a compound of the formula Y—Z wherein Y and Z have the meanings stated above and any amino, alkylamino, imino, hydroxy and carboxy group in Ar and Y is protected by a conventional protecting group as stated above, whereafter the nitro group may be reduced by conventional means to an amino group which may in turn be alkylated with a compound of the formula $R^2-Z$ wherein $R^2$ and Z have the meanings stated above.

The compound of the formula:

$HNR^2-Ar-L-Y$ wherein L is a group of the formula —$CH_2S$—, used as a starting material above, may be obtained by the reaction of a thiol of the formula $O_2N-Ar-CH_2SH$ wherein Ar has the meaning stated above with a compound of the formula Y—Z wherein Y and Z have the meanings stated above and any amino, alkylamino, imino and carboxy group in Ar and Y is protected by a conventional protecting group as stated above and any hydroxy group in Ar and Y may be protected by a conventional protecting group as stated above or alternatively any hydroxy group need not be protected. Thereafter the nitro group may be reduced by conventional means to an amino group which in turn may be alkylated with a compound of the formula $R^2-Z$ wherein $R^2$ and Z have the meanings stated above.

The compound of the formula:

$HNR^2-Ar-L-Y$ wherein L is a group of the formula —$OCH_2$— or —$SCH_2$—, used as a starting material above, may be obtained by the reaction of a compound of the formula $O_2N-Ar-OH$ or $O_2N-Ar-SH$ wherein Ar has the meaning stated above with a compound of the formula $Y-CH_2-Z$ wherein Y and Z have the meanings stated above and any amino, alkylamino, imino and carboxy group in Ar and Y is protected by a conventional protecting group as stated above, any hydroxy group in Ar is protected by a conventional protecting group as stated above, and any hydroxy group in Y may be protected by a conventional protecting group as stated above or alternatively any hydroxy group in Y need not be protected. Thereafter the nitro group may be reduced by conventional means to an amino group which in turn may be alkylated with a compound of the formula $R^2$—Z wherein $R^2$ and Z have the meanings stated above.

The compound of the formula:

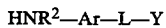

wherein L is a group of the formula —CO.CH$_2$— used as a starting material above, may be obtained by the reaction of an organometallic compound of the formula M—NG$^1$—Ar—C(OM)=CH$_2$ wherein G$^1$ and Ar have the meanings stated above and M is a metal group, for example lithium, with a compound of the formula Y—Z, wherein Y and Z have the meanings stated above and any amino, alkylamino, imino, hydroxy and carboxy group in Ar and Y is protected by conventional protecting group as stated above, and thereafter with water. Thereafter the protecting group G$^1$ may be removed by conventional means while the conventional protecting group on any amino, alkylamino and imino group in Ar and Y remains intact whereafter the amine may be alkylated with a compound of the formula $R^2$—Z wherein $R^2$ and Z have the meanings stated above.

The organomethallic compound of the formula M—NG$^1$—Ar—C(OM)=CH$_2$ used as a starting material above may be obtained by the reaction of the ketone of the formula NHG$^1$—Ar—CO.CH$_3$ with a metal amide, for example a lithium amide, for example lithium diisopropylamide, in a conventional solvent, for example tetrahydrofuran.

The compound of the formula:

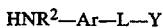

wherein L is a group of the formula —CH$_2$.CO—, used a starting material above, may be obtained by the reaction of an acid of the formula HNG$^1$—Ar—CH$_2$.CO$_2$H, or a reactive derivative thereof, wherein G$^1$ and Ar have the meanings stated above with an organometallic compound of the formula Y—M wherein Y has the meaning stated above and M is a metal group, for example magnesium or cadmium, and any amino, alkylamino, imino, hydroxy and carboxy group in Ar and Y is protected by a conventional protecting group as stated above, whereafter the protecting group G$^1$ may be removed by conventional means while the conventional protecting group on any amino, alkylamino and imino group in Ar and Y remains intact and whereafter the amine may be alkylated with a compound of the formula $R^2$—Z wherein $R^2$ and Z have the meanings stated above.

The compound of the formula:

wherein L is a group of the formula —CO.O—, used as a starting material above, may be obtained by the reaction of an acid of the formula O$_2$N—Ar—CO$_2$H, or a conventional reactive derivative thereof, wherein Ar has the meaning stated above with an alcohol of the formula HO—Y wherein Y has the meaning stated above and any amino, alkylamino, imino, hydroxy and carboxy group in Ar and Y is protected by a conventional protecting group. Thereafter the nitro group may be reduced by conventional means to an amino group which in turn may be alkylated with a compound of the formula $R^2$—Z wherein $R^2$ and Z have the meanings stated above.

(b) A further preferred process for the manufacture of a quinazoline of the invention wherein L is a group of the formula —CONH— or —CONR$^3$—, comprises the reaction of an acid of the formula III, or a reactive derivative thereof, with a compound of the formula H$_2$N—Y or R$^3$NH—Y wherein $R^1$, $R^2$, $R^3$, $R^4$, Ar and Y have the meanings stated above and any amino, alkylamino, imino and carboxy group in $R^1$, Ar and Y is protected by a conventional protecting group as stated above and any hydroxy group in $R^1$, $R^2$, Ar and Y may be protected by a conventional protecting group as stated above or alternatively any hydroxy group need not be protected; whereafter the protecting groups are removed by conventional means.

A suitable reactive derivative of an acid of the formula given above may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide, for example dicyclohexylcarbodiimide.

The reaction is preferably carried out in the presence of a suitable base as stated above, in a suitable solvent or diluent such as methylene chloride, dimethylformamide, dimethylacetamide or dimethylsulphoxide and at a temperature in the range, for example, 10° to 100° C., conveniently at or near laboratory temperature.

The carboxylic acid used as starting material may be obtained by the reaction of a compound of the formula II wherein $R^1$, $R^4$ and Z have the meanings stated above, with a compound of the formula:

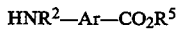

wherein $R^2$ and Ar have the meanings stated above and $R^5$ is a protecting group which can be removed to provide a carboxylic acid. $R^5$ may be, for example, a methyl or an ethyl group which may be removed by hydrolysis with a base, for example sodium hydroxide or $R^5$ may be, for example, a tert-butyl group which may be removed by cleavage with an organic acid, for example trifluoroacetic acid. The protecting group for the carboxy group in $R^5$ may be, for example, an esterifying group which can be removed while the protecting group for any amino, alkylamino, imino, carboxy and hydroxy group in $R^1$, $R^2$, Ar and Y is retained.

(c) A further preferred process for the manufacture of a quinazoline of the invention wherein L is a group of the formula —CO.O—, comprises the reaction, in the presence of a suitable base as stated above, of an acid of the formula III, or a reactive derivative thereof, with a compound of the formula HO—Y, wherein $R^1$, $R^2$, $R^3$, $R^4$, Ar and Y have the meanings stated above and any amino, alkylamino, imino, hydroxy and carboxy group in $R^1$, $R^2$, Ar and Y is protected by a conventional protecting group as stated above; whereafter the protecting groups are removed by conventional means.

The reaction is preferably carried out in a suitable solvent or diluent such as dimethylformamide, dimethylacetamide or dimethylsulphoxide at a temperature in the range 10° to 100° C., conveniently at or near laboratory temperature.

(d) A further preferred process for the manufacture of a quinazoline of the invention, wherein $R^1$ is alkoxy, hydroxyalkoxy or alkoxyalkoxy, comprises the reaction of a compound of the formula IV wherein $R^1$ has the last-mentioned meaning stated above, provided that when there is a hydroxy substituent in $R^1$ it is protected by a conventional protecting group as stated above, and Z is a displaceable group, with a compound of the formula:

$$HNR^2-Ar-L-Y$$

wherein $R^2$, Ar, L and Y have the meanings stated above, provided that when there is an amino, alkylamino, imino, hydroxy or carboxy group in $R^2$, Ar or Y any amino, alkylamino, imino and carboxy group is protected by a conventional protecting group as stated above and any hydroxy group may be protected by a conventional protecting group, as stated above or alternatively any hydroxy group need not be protected; whereafter the protecting groups are removed by conventional means, as stated above and the $R^1$ group situated at the 4-position of the quinazoline ring is cleaved by hydrolysis with a base, for example sodium hydroxide, to form a quinazoline of the invention.

(e) A further preferred process for the manufacture of a quinazoline of the invention wherein Y is a group of the formula $-A-Y^1$ in which one constituent methylene group in A is replaced by a sulphinyl or sulphonyl group, or wherein there is an alkylsulphinyl or alkylsulphonyl substituent in Y, comprises the oxidation of a compound of the formula I wherein Y is a group of the formula $-A-Y^1$ in which A is replaced by a thio group, or wherein there is an alkylthio substituent in Y, with a suitable oxidising agent.

A suitable oxidising agent is, for example, any reagent known to oxidise a thio group to a sulphinyl or sulphonyl group, for example, hydrogen peroxide, a peracid such as 3-chloroperbenzoic acid or peroxyacetic acid, or chromium trioxide. When a compound carrying a sulphinyl group is required the required stoichiometric amount of any one of the above oxidising agents may be used in order to reduce the production of a compound carrying a sulphonyl group. Alternatively a milder oxidising agent may be used, for example sodium or potassium metaperiodate. It will be appreciated that when a compound of the formula I containing a sulphonyl group is required, it may be obtained by the oxidation of the corresponding sulphinyl compound as well as by the oxidation of the corresponding thio compound.

(f) A futher preferred process for the manufacture of a quinazoline of the invention wherein there is a carboxy or carboxyalkyl substituent in Y, comprises the cleavage of a compound of the formula I wherein there is an alkoxycarbonyl or alkoxycarbonylalkyl substituent in Y.

Suitable conditions for the cleavage reaction include, for example, hydrolysis with a base, for example sodium hydroxide; or when, for example, a tert-butyl group is to be cleaved, treatment with an organic acid, for example trifluoroacetic acid.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carring out one of the aforesaid processes using an optically active starting material, or by resolution of a racemic form of said compound using a conventional procedure.

As stated above a quinazoline derivative of the present invention possesses anti-tumour activity. This activity may be assessed, for example, using one or more of the procedures set out below:

(a) An in vitro assay which determines the ability of a test compound to inhibit the enzyme thymidylate synthase. Thymidylate synthase was obtained in partially purified form from L1210 mouse leukaemia cells and utilised using the procedures described by Jackman et al. (*Cancer Res.*, 1986, 46, 2810);

(b) An assay which determines the ability of a test compound to inhibit the growth of the leukaemia cell line L1210 in cell culture. The test is similar to that described in UK Patent Specification No. 2065653B;

(c) An assay which determines the ability of a test compound to inhibit the growth of the human breast cancer cell line MCF-7 in cell culture. The test is similar to that described by Lippman et al. (*Cancer Res.*, 1976, 36, 4595); and (d) An assay which determines the ability of a test compound to inhibit the growth of the lymphoma cell line L5178Y TK-/- in vitro. The lymphoma cell line L5178Y TK-/- is deficient in the enzyme thymidine kinase which enzyme phosphorylates thymidine and thus operates to generate a pool of thymidylate when de novo synthesis of thymidylate is prevented by the presence of an effective amount of an inhibitor of thymidylate synthase. The L5178Y TK-/-cell line is thereby more sensitive to the presence of an inhibitor of thymidylate synthase. [L5178Y TK-/- was obtained by mutation of the parent L5178Y cell line which is described by, for example, Fischer et al., *Methods in Medical Research*, 1964, 10, 247]. The assay utilises a double layer soft-agar cloning technique similar to that described by Courtenay et al. (*British J. Cancer*, 1976, 34, 39). Each test compound is added at a range of concentrations to L5178Y TK-/- cells which have entered exponential growth phase in cell culture and the cells are incubated for 18 hours, harvested, washed with fresh culture medium and plated into soft-agar for clonogenic evaluation. After about 12 days colonies of cells are stained and counted.

A quinazoline of the present invention may itself be active or it may be a pro-drug which is converted in vivo to an active compound.

Although the pharmacological properties of the quinazolines of the invention vary with structural changes, in general quinazolines of the invention possess activity in one or more of the above tests (a) to (d):
Test (a) $IC_{50}$ in the range, for example, 0.02–10 $\mu M$;
Test (b) $IC_{50}$ in the range, for example, 0.5–10 $\mu M$;
Test (c) $IC_{50}$ in the range, for example, 0.1–100 $\mu M$;
Test (d) The dose required to reduce the fraction of surviving cells to 10% of those treated lies in the range, for example, 1–100 $\mu M$;

In general those quinazolines of the invention which are particularly preferred possess activity in one or more of the above tests (a) to (d):
Test (a) $IC_{50}$ in the range, for example, 0.02–1 $\mu M$;

Test (b) $IC_{50}$ in the range, for example, 0.5–10 μM;
Test (c) $IC_{50}$ in the range, for example, 0.1–5 μM;
Test (d) The dose required to reduce the fraction of surviving cells to 10% of those treated lies in the range, for example, 1–50 μM.

Thus, by way of example, the quinazoline, p-[N-(3,4-dihydro-2-methyl-4-oxoquinazolin-6-ylmethyl)-N-(prop-2-ynyl)amino]-N-(2-pyridylmethyl)benzamide has an $IC_{50}$ of 0.5 μM against thymidylate synthase [Test (a)] and an $IC_{50}$ of 3.9 μM against the L1210 cell line [Test (b)]; and the quinazoline, p-[N-(3,4-dihydro-2-methyl-4-oxoquinazolin-6-ylmethyl)-N-(prop-2-ynyl)amino]-N-(2-nitrobenzyl)benzamide has $IC_{50}$ of 0.05 μM in Test (a) and an $IC_{50}$ of 1.8 μM in Test (b).

A quinazoline of the invention, or a pharmaceutically-acceptable salt thereof, may be administered to a warm-blooded animal, including a human, in the form of a pharmaceutical composition which comprises the quinazoline, or a pharmaceutically-acceptable salt thereof, in association with a pharmaceutically-acceptable diluent or carrier.

The composition may be in a form suitable for oral administration, as a tablet or capsule, or, especially for parenteral injection (including intravenous, subcutaneous, intramuscular, intravascular or infusion), as a sterile solution, suspension or emulsion, or for topical administration, as an ointment or cream, or for rectal administration as a suppository.

The composition may contain, in addition to the quinazoline of the invention, one or more other anti-tumour substances selected from, for example, mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

In general the above compositions may be prepared in a conventional manner using conventional excipients.

The quinazoline will normally be administered to a warm-blooded animal at a unit dose within the range 50–5000 mg per square meter body area of the animal, i.e. approximately 1–100 mg/kg, and this normally provides a therapeutically-effective dose. A unit dose form such as a tablet or capsule will usually contain, for example, 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage will be determined by the practitioner who is treating any particular patient.

According to further feature of the present invention there is provided a method for producing an anti-tumour effect in a warm-blooded animal, such as man, in need of such treatment which comprises administering to said animal an effective amount of a quinazoline of the present invention, or a pharmaceutically-acceptable salt thereof. The invention also provides the use of a quinazoline of the present invention, or a pharmaceutically-acceptable salt thereof, in the manufacture of a novel medicament for use in the production of an anti-tumour effect in a warm blooded animal, such as man.

A quinazoline of the present invention is expected to possess a wide range of anti-tumour activities. CB3717 showed promising activity against human breast, ovarian and liver cancer and consequently it is expected that a quinazoline of the present invention will possess anti-tumour activity against these cancers. It is in addition expected that a quinazoline of the present invention will possess anti-tumour activity against a range of leukaemias, lymphoid malignancies and solid tumours such as carcinomas and sarcomas. Such tumours require thymidine monophosphate as one of the essential nucleotides for the synthesis of cellular DNA. In the presence of an effective amount of a thymidylate synthase inhibitor such as an effective amount of a quinazoline of the present invention it is expected that tumour growth will be inhibited.

As previously mentioned a quinazoline of the invention, or a pharmaceutically-acceptable salt thereof, is also of value in the treatment of, for example, allergic conditions such as psoriasis. In using a quinazoline of the invention for this purpose the compound will normally be administered at a dose within the range 50–5000 mg per square meter body area of the animal. In general for the treatment of an allergic condition such as psoriasis topical administration of a quinazoline of the invention is preferred. Thus, for example, for topical administration a daily dose in the range, for example, 1 to 50 mg/kg will be used.

The invention is illustrated but not limited by the following Examples in which unless otherwise stated:

(i) evaporations were carried out by rotary evaporation in vacuo and work-up procedures were carried out after removal of residual solids by filtration;

(ii) operations were carried out at laboratory temperature, that is in the range 18°–20° C. and under an atmosphere of an inert gas such as argon;

(iii) column chromatography (by the flash procedure) and medium pressure liquid chromatography (MPLC) were preformed on Merck Kieselgel silica (Art. 9385) obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques [proton magnetic resonance spectra were determined using a Jeol FX 90Q or a Bruker AM200 spectrometer operating at a field strength of 200 MHz; chemical shifts are reported in parts per million downfield from tetramethylsilane as an internal standard (δ scale) and peak multiplicities are shown thus: s, singlet; d, doublet; d of d's, doublet of doublet's; t, triplet, m, multiplet; fast-atom bombardment (FAB) mass spectral data were obtained using a VG Analytical MS9 spectrometer and xenon gas and, where appropriate, either positive ion data or negative ion data were collected];

(vi) intermediates were not generally fully characterised and purity was assessed by thin layer chromatographic, infra-red (IR) or NMR analysis; and (vii) melting points are uncorrected and were determined using a Mettler SP62 automatic melting point apparatus, a Koffler hot plate apparatus or an oil-bath apparatus.

EXAMPLE 1

Diphenylphosphoryl azide (0.7 ml) and triethylamine (1.1 ml) were added successively to a mixture of p-[N-(3,4-dihydro-2-methyl-4-oxoquinazolin-6-ylmethyl)-N-(prop-2-ynyl)amino]benzoic acid (as its trifluoroacetic acid salt; 1.0 g; UK Patent Specification No. 2188319A) and dimethylsulphoxide (40 ml) and the mixture was stirred at laboratory temperature for 5 hours. 3-Aminomethylpyridine (0.33 ml) was added and the mixture was stirred at laboratory temperature for 16 hours. The mixture was poured onto a mixture of ice and water (200 ml). The solid so obtained was filtered off, washed with water (3×30 ml) and dried; resuspended in ethyl acetate, triturated, filtered off and dried. There was thus obtained p-[N-(3,4-dihydro-2-methyl-4-oxoquinazolin-6-ylmethyl)-N-(prop-2-ynyl)amino]-N-(3-pyridylmethyl)benzamide (containing one equivalent of water, 0.82 g), m.p. 237°–239° C.

NMR Spectrum: (CD$_3$SOCD$_3$) 2.33 (s, 3H, 2-CH$_3$), 3.19 (t, 1H, C≡CH, J=2 Hz), 4.31 (d, 2H, CH$_2$C≡CH, J=2 Hz), 4.45 (d, 2H, NHCH$_2$, J=6 Hz), 4.78 (s, 2H, CH$_2$N), 6.84 (d, 2H, aromatic, J=9 Hz), 7.32 (d of d's, 1H, pyridine ring, J=6 and 3 Hz), 7.52 (d, 1H, 8-H, J=8 Hz), 7.69 (d of d's, 1H, 7-H, J=8 and 2 Hz), 7.70 (d of d's, 1H, pyridine ring, J=6 and 1.5 Hz), 7.74 (d, 2H, aromatic, J=9 Hz), 7.97 (d, 1H, 5-H, J=2 Hz), 8.42 (d of d's, 1H, pyridine ring, J=3 and 1.5 Hz), 8.51 (d, 1H, pyridine ring, J=1.5 Hz), 8.72 (t, 1H, CONH, J=6 Hz);

Mass Spectrum: (positive ion FAB) m/e (P+1) 438;

Elemental Analysis: Found C, 68.4; H, 5.5; N, 15.3; C$_{26}$H$_{23}$N$_5$O$_2$.1H$_2$O requires C, 68.6; H, 5.5; N, 15.4%.

EXAMPLE 2

The process described in Example 1 was repeated using, where necessary, the appropriate benzoic acid in place of p-[N-(3,4-dihydro-2-methyl-4-oxoquinazolin-6-ylmethyl)-N-(prop-2-ynyl)amino]-benzoic acid and the appropriate amine, or the appropriate alcohol, in place of 3-aminomethylpyridine. There were thus obtained the compounds described in the following tables, the structures of which were confirmed by proton magnetic resonance and mass spectroscopy and by elemental analysis.

TABLE I

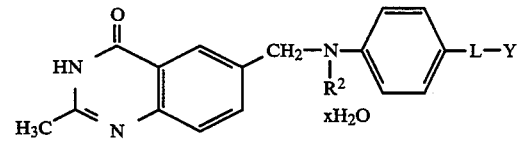

| Compound No. (Note) | R$^2$ | L | Y | x | m.p. (°C.) |
|---|---|---|---|---|---|
| 1 | prop-2-ynyl | —CONH— | 2-pyridylmethyl | 1 | 212–218 (decomp.) |
| 2 | prop-2-ynyl | —CONH— | 4-pyridylmethyl | 1 | 243–244 (decomp.) |
| 3 | prop-2-ynyl | —CONH— | 2-(pyrid-2-yl)-ethyl | 1 | 219–221 |
| 4(1) | prop-2-ynyl | —CONH— | 1-(pyrid-3-yl)-ethyl | 1 | 203–209 |
| 5(2) | prop-2-ynyl | —CONH— | (1-benzylimidazol-2-yl)methyl | 0.5 | 234–237 |
| 6(3) | ethyl* | —CONH— | (1-methylimidazol-2-yl)methyl | 0.3 | 295–300 |
| 7 | ethyl* | —CONH— | 2-(imidazol-4-yl)-ethyl | 0.5 | 197–205 |
| 8 | ethyl* | —CONH— | 3-(imidazol-1-yl)-propyl | 2 | 138–142 |
| 9(4) | ethyl* | —CO.O— | (1-benzylimidazol-2-yl)methyl | 0.5 | 166–169 |
| 10(5) | ethyl* | —CO.O— | (1-methylimidazol-2-yl)methyl | 0.5 | 110–118 |
| 11(6) | prop-2-ynyl | —CONH— | 5-tetrazolylmethyl | 1.3 | 257–260 (decomp.) |
| 12(7) | prop-2-ynyl | —CONH— | (1-methyltetrazol-5-yl)methyl | 1.8 | 251–255 |
| 13(8) | prop-2-ynyl | —CONH— | 3-(tetrazol-5-yl)-propyl | 3 | 239–243 |
| 14 | ethyl* | —CONH— | 2-benzimidazolyl-methyl | 2 | 176–181 |
| 15 | ethyl* | —CONH— | 2-(indol-3-yl)-ethyl | 0.5 | 220–223 |

NOTES

*p-[N-(3,4-Dihydro-2-methyl-4-oxoquinazolin-6-ylmethyl)-N-ethylamino]benzoic acid (as its trifluoroacetic acid salt) was obtained by the same method described in UK Patent Specification No. 2188319A for the preparation of p-[N-(3,4-dihydro-2-methyl-4-oxoquinazolin-6-ylmethyl)-N-(prop-2-ynyl)amino]benzoic acid (as its trifluoroacetic acid salt) except that ethyl iodide was used in place of propargyl bromide.

(1) The appropriate amine is described in J. Heterocyclic Chem., 1968, 5, 715.
(2) The appropriate amine was prepared as follows: A solution of 1-benzyl-2-chloromethylimidazole (5.5 g; J. Amer. Chem. Soc., 1949, 71, 383) in dimethylformamide (10 ml) was added dropwise to a solution of potassium phthalimide (5.7 g) in dimethylformamide (15 ml) and the mixture was stirred at laboratory temperature for 18 hours. The mixture was filtered and the filtrate was evaporated. The residue was dissolved in chloroform (200 ml) and washed with a 0.2N aqueous solution of sodium hydroxide and then with water. The organic solution was dried (MgSO$_4$) and evaporated and the residue was purified by chromatography on a silica gel column using ethyl acetate as eluent. There was thus obtained as an oil, which solidified on standing, 1-benzyl-2-

TABLE I-continued phthalimidomethylimidazole (3.1 g), m.p. 148–151° C.
Hydrazine hydrate (0.4 ml of an 85% solution in water) was added to a solution of the product so obtained (2.2 g) in methanol (50 ml) and the mixture was heated to reflux for 1 hour. The mixture was evaporated and the residue was purified by chromatography on a silica gel column using a 92:5:3 v/v mixture of ethyl acetate, methanol and an aqueous solution of ammonium hydroxide (30% by weight of $NH_3$) as eluent. There was thus obtained as a yellow liquid 2-aminomethyl-1-benzylimidazole (1.2 g), the structure of which was confirmed by proton magnetic resonance and mass spectroscopy.

(3)The appropriate amine was prepared as follows: A mixture of 2-chloromethyl-1-methylimidazole hydrochloride (2.9 g; obtained using a similar method to that described in J. Amer. Chem. Soc., 1949, 71, 383 for the preparation of 1-benzyl-2-chloromethylimidazole) and liquid ammonia (12 ml) was allowed to stand at laboratory temperature for 2 hours and then heated to reflux for 2 hours. The excess of ammonia was then evaporated. The residue was dissolved in chloroform, the solution was filtered and the filtrate was evaporated. There was thus obtained as a yellow solid 2-aminomethyl-1-methylimidazole (1.3 g) which was used without further purification.

(4)The appropriate alcohol, 1-benzyl-2-hydroxymethylimidazole is described in J. Amer. Chem. Soc., 1949, 71, 383.

(5)The appropriate alcohol was obtained using a similar method to that described in J. Amer. Chem. Soc., 1949, 71, 383 for the preparation of 1-benzyl-2-hydroxymethylimidazole.

(6)The appropriate amine is described in J. Org. Chem., 1959, 24, 1643.

(7)The appropriate amine was prepared as follows: A mixture of 5-phthalimidomethyltetrazole (5 g; J. Org. Chem., 1959, 24, 1643), bis(tributyltin) oxide (11 ml) and methyl iodide (9 ml) was stirred vigorously at laboratory temperature for 3 days. The mixture was evaporated to dryness and the residue was washed with hexane and then triturated under ethanol. There was thus obtained as a white solid 1-methyl-5-phthalimidomethyltetrazole (3.1 g).
A mixture of the product so obtained (1.5 g), hydrazine hydrate (0.3 ml of an 85% solution in water) and ethanol (25 ml) was heated to reflux for 3 hours. The mixture was cooled in ice, filtered and evaporated. There was thus obtained 2-aminomethyl-1-methyltetrazole as an oil (0.3 g) which was stored at 4° C. and used without further purification.

(8)The appropriate amine was obtained using the method described in J. Org. Chem., 1959, 24, 1643 and using 4-aminobutyronitrile in place of aminoacetonitrile.

TABLE II

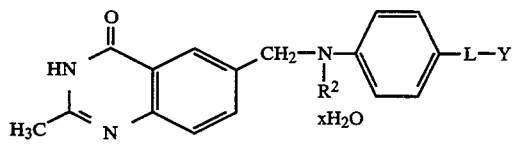

| Compound No. (Note) | $R^2$ | L | Y | x | m.p. (°C.) |
|---|---|---|---|---|---|
| 1(1) | prop-2-ynyl | —CONH— | phenyl | 0.8 | 262–266 |
| 2(2) | prop-2-ynyl | —CONH— | 4-tert-butoxy-carbonylphenyl | | 211–214 (decomp.) |
| 3(3) | prop-2-ynyl | —CONH— | 4-carboxyphenyl | 0.8 | 283–292 (decomp.) |
| 4 | prop-2-ynyl | —CONH— | benzyl | 0.8 | 231–234 |
| 5 | prop-2-ynyl | —CONH— | [S](—)-α-methylbenzyl | | 200–205 |
| 6 | prop-2-ynyl | —CONH— | [R](+)-α-methylbenzyl | 0.8 | 214–216 |
| 7 | prop-2-ynyl | —CONH— | 4-chlorobenzyl | 0.8 | 226–230 |
| 8 | prop-2-ynyl | —CONH— | 3-chlorobenzyl | 1 | 195–198 |
| 9 | prop-2-ynyl | —CONH— | 2-chlorobenzyl | 0.3 | 205–210 |
| 10 | prop-2-ynyl | —CONH— | 4-nitrobenzyl | 2 | 229–233 |
| 11 | prop-2-ynyl | —CONH— | 3-nitrobenzyl | 0.5 | 240–243 |
| 12(4) | prop-2-ynyl | —CONH— | 4-aminobenzyl | 0.5 | 211–215 |
| 13 | prop-2-ynyl | —CONH— | 4-carboxybenzyl | 2 | 175–179 |
| 14(5) | prop-2-ynyl | —CONH— | 3-carboethoxybenzyl | 1.3 | 212–216 |
| 15(6) | prop-2-ynyl | —CONH— | 3-carboxybenzyl | 2.5 | 164–168 |
| 16 | prop-2-ynyl | —CONH— | 3-fluorobenzyl | 1 | 213–218 |
| 17*(7) | prop-2-ynyl | —CONH— | 2-nitrobenzyl | 2 | 225–227 |
| 18*(8) | prop-2-ynyl | —CONH— | 3-hydroxybenzyl | 2 | 183–187 |

NOTES
*The product was purified by chromatography on a silica gel column using increasingly polar mixtures of methylene chloride and ethanol as eluent.
(1)Diethyl cyanophosphonate was used in place of diphenylphosphoryl azide.

TABLE II-continued (2) Diethyl cyanophosphonate was used in place of diphenylphosphoryl azide. Tert-butyl 4-aminobenzoate is described in Synth. Comm., 1984, 14, 921.
(3) A mixture of Compound No. 2. described immediately above Compound No. 3 in Table II, and trifluoroacetic acid was stirred at laboratory temperature for 10 minutes and evaporated to give the benzoic acid, as its trifluoroacetic acid salt.
(4) 4-Aminobenzylamine is described in J. Med. Chem., 1977, 20, 1189.
(5) 3-Carboethoxybenzyl bromide (1 ml; Heterocycles, 1977, 6, 5) was added to a saturated solution of ammonia in acetonitrile (30 ml) which had been cooled to $-30°$ C. The mixture was stirred and allowed to warm to laboratory temperature. The mixture was filtered and the filtrate was evaporated. The residue was purified by chromatography on a silica gel column using a 10:1 v/v mixture of ethyl acetate and methanol as eluent. There was thus obtained as an oil 3-carboethoxybenzylamine (0.4 g) which was used without further purification as the appropriate amine in the process described in Example 1.
(6) A portion of Compound No. 14 (obtained as described in note (5) above) was dissolved in methanol and hydrolysed at laboratory temperature by the addition of a 2N aqueous sodium hydroxide solution.
(7) A solution of 2-nitrobenzyl chloride (1.0 g) in acetonitrile (10 ml) was added to a cold ($-30°$ C.) solution of liquid ammonia (10 ml) in acetonitrile (20 ml). The mixture was stirred at $-30$ to $-40°$ C. for 3 hours and allowed to warm to 20° C. Evaporation left an orange gum which was chromatographed on silica gel using increasingly polar methanol/ethyl acetate mixtures as eluent to give a yellow gum which slowly crystallised. There was thus obtained 2-nitrobenzylamine (0.13 g).
(8) A solution of boron tribromide in methylene chloride (3.6 ml of 1M solution) was added dropwise to a solution of 3-methoxybenzylamine (0.5 g) in methylene chloride (10 ml) which had been cooled to $-5°$ C. The mixture was stirred for 1 hour and then a further 3.6 ml of the boron tribromide solution was added. Stirring was continued at $-5°$ C. for 3 hours. The solution was allowed to warm to 20° C., diluted with methylene chloride (30 ml), and the white solid was filtered off. The solid was treated with dilute aqueous sodium bicarbonate solution until the washings were almost neutral. The residual solid was dried. The white solid was slurried with dry dimethylformamide, filtered and the filtrate was evaporated to leave a cream coloured oil. There was thus obtained 3-hydroxybenzylamine (0.17 g).

EXAMPLE 3

The process described in Example 1 was repeated using the appropriate benzoic acid in place of p-[N-(3,4-dihydro-2-methyl-4-oxoquinazolin-6-ylmethyl)-N-(prop-2-ynyl)amino]benzoic acid, and the appropriate amine in place of 3-aminomethylpyridine. There were thus obtained the compounds described in the following table, the structures of which were confirmed by proton magnetic resonance and mass spectroscopy and by elemental analysis.

TABLE III

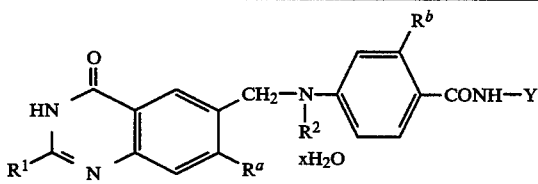

| Ex. 3 Compd. No. (Note) | $R^1$ | $R^a$ | $R^2$ | $R^b$ | Y | x | m.p. (°C.) |
|---|---|---|---|---|---|---|---|
| 1(1)* | Me | Me | prop-2-ynyl | H | 3-nitrobenzyl | — | 251–754 |
| 2(2)* | Me | H | Me | F | 3-nitrobenzyl | — | 269–272 |
| 3(3)* | MeO | H | prop-2-ynyl | H | 3-nitrobenzyl | 0.3 | 181–185 |
| 4(4) | H$_2$N | H | prop-2-ynyl | H | 3-nitrobenzyl | 1.3 | 187–192 |
| 5(5) | FCH$_2$ | H | prop-2-ynyl | H | 3-nitrobenzyl | 0.5 | 232–234 |

NOTES
*In these cases the product was purified by column chromatography using increasingly polar mixtures of methylene chloride and ethanol as eluent.
(1) p-[N-(3,4-Dihydro-2,7-dimethyl-4-oxoquinazolin-6-ylmethyl-

TABLE III-continued

N-(prop-2-ynyl)amino]benzoic acid (as its trifluoroacetic acid salt) was obtained as described in UK Patent Specification No. 2202847A.
(2) p-[N-(3,4-Dihydro-2-methyl-4-oxoquinazolin-6-ylmethyl)-N-methylamino]-o-fluorobenzoic acid (as its trifluoroacetic acid salt) was obtained by repetition of the process described in UK Patent Specification No. 21888319A, in the portion of Example 11 thereof which is concerned with the preparation of starting materials, except that tert-butyl p-amino-o-fluorobenzoate was used in place of tert-butyl p-aminobenzoate, and methyl iodide was used in place of propargyl bromide. There was thus obtained the required starting material in 42% yield, as a white salt with trifluoroacetic acid. The tert-butyl p-amino-o-fluorobenzoate, used as a starting material, was prepared from o-fluoro-p-nitrobenzoic acid (described in UK Patent Specification No 2175903) by the conventional reactions of esterification with isobutene and by reduction of the tert-butyl ester so formed with iron powder in the presence of acetic acid using the conditions described in UK Patent Specification No. 2175903.
(3) p-[N-(3,4-Dihydro-2-methoxy-4-oxoquinazolin-6-ylmethyl)-N-(prop-2-ynyl)aminobenzoic acid, used as a starting material, was obtained as follows: N-[p-[N-(3,4-Dihydro-2-methoxy-4-oxoquinazolin-6-ylmethyl)-N-(prop-2-ynyl)amino]benzoyl]-L-glutamic acid (prepared as described in UK Patent Specification No. 2188319A, 0.5 g) was dissolved in a tris(hydroxymethyl)-aminomethane buffer solution (80 ml) containing 1N aqueous sodium hydroxide solution (1 ml). The basicity of the solution was adjusted to pH 7.3 and the mixture was warmed to 37° C. Carboxypeptidase G$_2$ enzyme solution (200 units) was added and the mixture was stirred vigorously at 37° C. for 1 hour. The mixture was cooled in ice, acidified to pH 4 by the addition of 1N aqueous hydrochloric acid solution and the white solid was filtered off, washed with water and dried. There was thus obtained the required starting material (0.3 g).
(4) p-[N-(2-Amino-3,4-dihydro-4-oxoquinazolin-6-ylmethyl)-N-(prop-2-ynyl)amino]benzoic acid was obtained by the method described in Note (3) above except that N-[p-[N-(2-amino-3,4-dihydro-4-oxoquinazolin-6-ylmethyl)-N-(prop-2-ynyl)-amino]benzoyl]-L-glutamate (prepared as described in UK Patent Specification No. 2065653B) was used as the substrate.
(5) The reaction was worked up by pouring the mixture into water and extracting with ethyl acetate (3 × 30 ml). The combined

TABLE III-continued organic extracts were dried (MgSo4) and evaporated and the residue was purified by column chromatography on silica gel using increasingly polar mixtures of chloroform and methanol as eluent. The resultant solid was triturated with acetone and the solid so obtained was washed with diethyl ether to give the desired product.

p-[N-(3,4-Dihydro-2-fluoromethyl-4-oxoquinazolin-6-ylmethyl)-N-(prop-2-ynyl)amino]benzoic acid (as its trifluoroacetic acid salt), used as a starting material, was prepared as follows: Using the procedure described in UK Patent Specification No. 2188319A (Example 5 thereof), 6-bromomethyl-2-fluoromethyl-3,4-dihydroquinazolin-4-one was reacted with tert-butyl p-(prop-2-ynylamino)benzoate [prepared by the alkylation of tert-butyl p-aminobenzoate with prop-2-ynyl bromide using the conditions described for related alkylations in J. Med. Chem., 1985, 28, 1468] and the resultant product was treated with tritiuoroacetic acid. There was thus obtained the required starting material in 53% yield, NMR Spectrum (CD$_3$SOCD$_3$) 3.32(1H), 4.38(2H), 4.84(2H), 5.18(1H), 5.42(1H), 6.85(2H), 7.6–7.82(4H), 8.03(1H).

EXAMPLE 4

Using the process described in Example 1, 5-[N-(3,4-dihydro-2-methyl-4-oxoquinazolin-6-ylmethyl)-N-(prop-2-ynyl)amino]pyridine-2-carboxylic acid was reacted with 3-nitrobenzylamine. The product was purified by column chromatography on silica gel using increasingly polar mixtures of methylene chloride and ethanol as eluent. There was thus obtained 5-[N-(3,4-dihydro-2-methyl-4-oxoquinazolin-6-ylmethyl)-N-(prop-2-ynyl)amino]-N-(3-nitrobenzyl)pyridine-2-carboxamide (containing 0.7 equivalents of water) in 5% yield, m.p. 245°–250° C.

The 5-[N-(3,4-dihydro-2-methyl-4-oxoquinazolin-6-ylmethyl)-N-(prop-2-ynyl)amino]pyridine-2-carboxylic acid was obtained as follows:

Using the method described in J. Med. Chem., 1980, 23, 1405, methyl 5-(N-tert-butoxycarbonylamino)pyridine-2-carboxylate was reacted with prop-2-ynyl bromide to give methyl 5-[N-tert-butoxycarbonyl-N-(prop-2-ynyl)amino]pyridine-2-carboxylate in 90% yield. A mixture of the product so obtained and trifluoroacetic acid was stirred at 0° C. for 1 hour and evaporated. There was thus obtained methyl 5-(N-prop-2-ynylamino)pyridine-2-carboxylate in 90% yield, as a gum.

Using the process described in UK Patent Specification No. 2188319A (Example 6 thereof), the product so obtained was reacted with 2-bromomethyl-3,4-dihydro-2-methylquinazolin-4-one to give the methyl ester of the required starting material and the methyl ester was hydrolysed by conventional treatment with aqueous N sodium hydroxide solution to give the required starting material in 3% yield as a gum which was used without further purification.

EXAMPLE 5 p-[N-(3,4-Dihydro-2-methyl-4-oxoquinazolin-6-ylmethyl)-N-(prop-2-ynyl)amino]benzoyl azide (0.53 g) and 3-nitrobenzyl alcohol (0.33 g) were suspended in dry dimethylformamide (20 ml) and 1,8-diazabicyclo[5.4.0]undec-7-ene (0.63 ml) was added. The mixture was stirred at laboratory temperature for 18 hours. The volume of the mixture was reduced to about 10 ml by evaporation and the residue was poured into water (50 ml). The precipitated solid was filtered off, washed with water (3×10 ml) and dried. The material was triturated with a 4:1 v/v mixture of methylene chloride and ethanol and the resultant solid was dried in air. There was thus obtained 3-nitrobenzyl p-[N-(3,4-dihydro-2-methyl-4-oxoquinazolin-6-ylmethyl)-N-(prop-2-ynyl)amino]benzoate (containing 0.7 equivalents of water, 0.22 g), m.p. 238°–241° C.

NMR Spectrum (CD$_3$SOCD$_3$) 2.32 (s, 3H, 2-CH$_3$), 3.22 (s, 1H, C≡CH), 4.36 (s, 2H, CH$_2$), 4.81 (s, 2H, CH$_2$), 5.42 (s, 2H, OCH$_2$), 6.88 (d, 2H, J=8 Hz, aromatic), 7.54 (d, 1H, J=6 Hz, aromatic), 7.63–7.75 (m, 3H, aromatic), 7.84 (d, 2H, J=8 Hz, aromatic), 7.85–7.97 (m, 2H, aromatic), 8.18 (d, 1H, J=6 Hz, aromatic), 8.29 (broad s, 1H, aromatic);

Mass Spectrum: (positive ion FAB) m/e (P+1) 483; Elemental Analysis: Found C, 65.3; H, 4.8; N, 11.5; C$_{27}$H$_{22}$N$_4$O$_5$.0.7 H$_2$O requires C, 65.4; H, 4.7; N, 11.3%.

The p-[N-(3,4-dihydro-2-methyl-4-oxoquinazolin-6-ylmethyl)-N-(prop-2-ynyl)amino]benzoyl azide, used as a starting material, was obtained as follows:

Diphenylphosphoryl azide (2.80 ml) and triethylamine (3.59 ml) were added successively to a mixture of p-[N-(3,4-dihydro-2-methyl-4-oxoquinazolin-6-methyl)-N-(prop-2-ynyl)amino]benzoic acid (as its trifluoroacetic acid salt; 3.0 g; UK Patent Specification No. 2188319A) and dimethylformamide (35 ml) which had been cooled to approximately 5° C. by immersion in an ice bath. The mixture was stirred at 5° C. for 3 hours and allowed to stand at 5° C. overnight. The precipitated solid was filtered off, washed in turn with dimethylformamide and diethyl ether and dried. There was thus obtained p-[N-(3,4-dihydro-2-methyl-4-oxoquinazolin-6-ylmethyl)-N-(prop-2-ynyl)amino]benzoyl azide (2.10 g).

NMR Spectrum: (CD$_3$SOCD$_3$) 2.33 (s, 3H, CH$_3$), 3.24 (t, 1H, J=1 Hz, C≡CH), 4.40 (broad s, 2H, CH$_2$), 4.85 (s, 2H, CH$_2$), 6.89 (d, 2H, J=8 Hz, aromatic), 7.54 (d, 1H, J=6 Hz, aromatic), 7.67 (d of d's, 1H, J=6 and 2 Hz, aromatic), 7.78 (d, 2H, J=8 Hz, aromatic), 7.95 (d, 1H, J=2 Hz, aromatic), 12.2 (broad s, 1H, NH);

Mass Spectrum: m/e (P) 372.

EXAMPLE 6

The process described in Example 5 was repeated using p-[N-(3,4-dihydro-2-methyl-4-oxoquinazolin-6-ylmethyl)-N-(prop-2-ynyl)amino]benzoyl azide and the appropriate amine in place of 3-nitrobenzyl alcohol. Any modifications to the general experimental procedure are disclosed in the appropriate footnote. There were thus obtained the compounds described in the following table, the structures of which were confirmed by proton magnetic resonance and mass spectroscopy and by elemental analysis.

TABLE IV

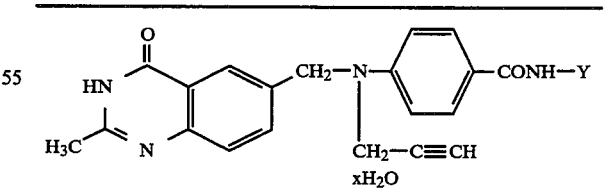

| Ex. 6 Compd. No. (Note) | Y | x | m.p. (°C.) |
|---|---|---|---|
| 1(1) | 2-thienylmethyl | 1.3 | 224–228 |
| 2 | 3-thienylmethyl | 0.8 | 238–245 |
| 3 | 2-furylmethyl | 1 | 196–210 |
| 4 | 3-furylmethyl | — | 226–227 |
| 5 | 2-thiazolylmethyl | 0.6 | 238–240 |
| 6 | 4-thiazolylmethyl | 0.6 | 206–208 |

TABLE IV-continued

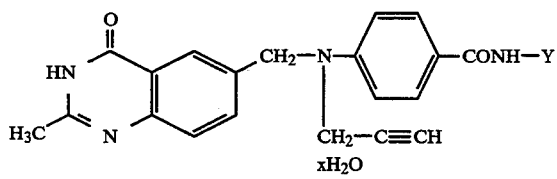

xH₂O

Ex. 6

| Compd. No. (Note) | Y | x | m.p. (°C.) |
|---|---|---|---|
| 7 | 5-thiazolylmethyl | 0.8 | 242–248 |
| 8 | (4-methylthiazol-2-yl)methyl | 0.8 | 246–252 |
| 9 | (3,5-dimethylisoxazol-4-yl)methyl | 0.3 | 281–282 |
| 10(2) | 1,2,4-triazol-3-ylmethyl | 1.5 | 116–120 |
| 11(2) | (5-methyl-1,2,4-triazol-3-yl)methyl | 1 | 204–207 |
| 12(3) | (5-pyrid-4-yl-1,2,4-triazol-3-yl)methyl | — | 210–214 |
| 13 | 3-quinolylmethyl | — | 250–270 (decomposes) |
| 14 | 4-quinolylmethyl | 0.3 | 190–192 |
| 15 | 8-quinolylmethyl | 0.3 | 144–146 |
| 16 | 2-[N-(5-nitropyrid-2-yl)amino]ethyl | 1.5 | 270–272 |
| 17(4) | 1-(tetrazol-5-yl)ethyl | 2.3 | — |
| 18 | 2-methyl-1-(tetrazol-5-yl)propyl | 1 | 197–200 |
| 19(5) | (4-hydroxy-6-methylpyrimidin-2-yl)methyl | — | 261–264 |
| 20(6) | (2,6-dioxopyrimidin-4-yl)methyl | — | 305 |

NOTES
(1) The concentrated reaction mixture was poured into water. The mixture was acidified to pH 6 by the addition of 1N aqueous hydrochloric acid solution. The resultant precipitate was dried and purified by column chromatography on silica gel using increasingly polar mixtures of methylene chloride and ethanol as eluent.
(2) The product also contains two equivalents of trifluoroacetic acid.
(3) The product contains 1.8 equivalents of chloroform.
(4) The product gave the following characteristic NMR signals (CD₃SOCD₃) 1.6(d, 3H), 2.31(s, 3H), 3.18(t, 1H), 4.34(d, 2H), 4.77(s, 2H), 5.43(m, 1H), 6.86(m, 2H), 7.5–8.0(m, 5H), 8.67(m, 1H).
(5) The product contained 0.25 equivalents of trifluoroacetic acid.
(6) Dimethylsulphoxide was used in place of dimethylformamide as the reaction solvent. The product was isolated as its trifluoroacetic acid salt.

Information concerning the amines required for the compounds described in Table IV is given below.

(i) 3-Aminomethylthiophene is described in *J. Med. Chem.*, 1977, 20, 1287.

(ii) The preparation of 3-aminomethylfuran is described below:

Diethyl azodicarboxylate (5.2 ml) was added dropwise to a stirred suspension of 3-hydroxymethylfuran (3.18 g), phthalimide (4.76 g) and triphenylphosphine (8.5 g) in tetrahydrofuran (25 ml) which was cooled in an ice-bath to keep the temperature of the reaction mixture below 30° C. The mixture was stirred at laboratory temperature for 2 hours. The mixture was evaporated and the residue was purified by column chromatography on silica gel using methylene chloride as eluent. There was thus obtained 3-phthalimidomethylfuran (4.48 g).

A mixture of a portion (2 g) of the product so formed, hydrazine hydrate (0.51 ml) and ethanol (30 ml) was heated to 75° C. for 1.5 hours. Concentrated hydrochloric acid (1.67 ml) was added and the mixture was heated to 60° C. for 1 hour. The mixture was cooled in an ice-bath and filtered. The filtrate was evaporated. The residue was triturated in diethyl ether and the precipitated solid was filtered off, washed with diethyl ether and dried. There was thus obtained 3-aminomethylfuran hydrochloride (1.15 g).

(iii) 2-Aminomethylthiazole is described in *J. Amer. Chem. Soc.*, 1950, 72, 4526.

(iv) 4-Aminomethylthiazole is described in *J. Amer. Chem. Soc.*, 1950, 72, 4526.

(v) The preparation of 5-aminomethylthiazole is described below:

Thionyl chloride (5 ml) was added dropwise to a solution of 5-hydroxymethylthiazole (2.9 g; U.S. Pat. No. 4,221,802) in chloroform (35 ml). The mixture was evaporated to leave, as a dark oil, 5-chloromethylthiazole hydrochloride (4.42 g).

A mixture of the product so obtained, potassium phthalimide (20.8 g) and dimethylacetamide (40 ml) was stirred at laboratory temperature for 16 hours. The mixture was filtered and the filtrate was evaporated. The residue was partitioned between ethyl acetate and water. The organic phase was dried (MgSO₄) and evaporated. The residue was purified by column chromatography on silica gel using increasingly polar mixtures of methylene chloride and ethyl acetate as eluent. There was thus obtained 5-phthalimidomethylthiazole (2.18 g).

Using the procedure described in Note (ii) above, the product so obtained was reacted with hydrazine hydrate. There was thus obtained 5-aminomethylthiazole hydrochloride (1.13 g).

NMR Spectrum: (CD₃SOCD₃) 4.35 (q, 2H), 8.03 (s, 1H), 9.12 (s, 1H).

(vi) 2-Aminomethyl-4-methylthiazole is described in *Bull. Chem. Soc. Jap.*, 1973, 46, 3600 [*Chem. Abs.*, 80, 71072n].

(vii) 4-Aminomethyl-3,5-dimethylisoxazole was prepared from 4-chloromethyl-3,5-dimethylisoxazole using the procedure described in the last two paragraphs of Note (v) above.

(viii) 3-Aminomethyl-1,2-4-triazole is described in *Chem. Ber.*, 1964, 97, 528.

(ix) 3-Aminomethyl-5-methyl-1,2,4-triazole is described in *Chem. Ber.*, 1964, 97, 528.

(x) Using an analogous procedure to that described in *Chem. Ber.*, 1964, 97, 528, except that N-formyl-N'-(4-pyridyl)hydrazine was used in place of N-formylhydrazine, there was thus obtained 3-aminomethyl-5-(4-pyridyl)-1,2,4-triazole which showed the following NMR signals (CDCl₃) 3.89 (s, 2H), 7.89 (m, 2H), 8.64 (m, 2H).

(xi) 3-Aminomethylquinoline is described in *Chem. Pharm. Bull.*, 1966, 14, 566.

(xii) 4-Aminomethylquinoline is described in *Chem. Abs.*, 95, 97545d.

(xiii) The preparation of 8-aminomethylquinoline is described below:

A mixture of 8-methylquinoline (0.95 ml), N-bromosuccinimide (1.86 g), benzoyl peroxide (0.1 g) and carbon tetrachloride (15 ml) was heated to reflux for 2.5 hours and irradiated with the light from a 250 watt lamp. The mixture was cooled, filtered and evaporated. There was thus obtained 8-bromomethylquinoline (2.18 g).

A mixture of a portion (1.4 g) of the product so obtained, sodium azide (2.43 g) and dimethylformamide (20 ml) was stirred at laboratory temperature for 2.5 hours. A second portion of sodium azide (1.62 g) was added and the mixture was heated to 100° C. for 2 hours. The mixture was evaporated and the residue was partitioned between methylene chloride and water. The organic phase was washed with water, dried (Na₂SO₄) and evaporated. The residue was purified by column chromatography on silica gel using a 1:1 v/v mixture of methylene chloride and hexane as eluent. There was thus obtained 8-azidomethylquinoline (1 g).

A mixture of the product so obtained, 10% palladium-on-charcoal catalyst (0.2 g), methanol (5 ml) and ethyl acetate (20 ml) was stirred under an atmosphere of hydrogen for 3 hours. The mixture was filtered and the filtrate was evaporated. There was thus obtained 8-aminomethylquinoline (0.73 g).

(xiv) 5-(1-Amino-2-methylpropyl)tetrazole is described in *Tetrahedron*, 1971, 27, 1783.

(xv) 2-Aminomethyl-4-hydroxy-6-methylpyrimidine was obtained as follows:

A mixture of 2-phthalimidoacetimidate hydrochloride (6 g, *Chem. Ber.*, 1964, 97, 528) and a saturated aqueous potassium carbonate solution (50 ml) was stirred at ambient temperature for 3 minutes and then extracted with chloroform. The organic phase was dried ($Na_2SO_4$) and evaporated. A mixture of the solid so obtained, ammonium chloride (1.4 g) and methanol (100 ml) was stirred at laboratory temperature for 18 hours. The mixture was evaporated to give 2-phthalimidoacetamidine hydrochloride, as a white solid (5.5 g).

A solution of ethyl acetoacetate (2.72 g) in methanol (50 ml) was added to sodium hydride (55% w/w dispersion in mineral oil, 0.73 g). A portion (2 g) of the acetamidine hydrochloride was added and the mixture was heated to reflux for 18 hours. The mixture was evaporated and the residue was partitioned between ethyl acetate and dilute aqueous acetic acid solution. The organic phase was dried ($Na_2SO_4$) and evaporated. The residue was purified by column chromatography on silica gel using a 49:1 v/v mixture of chloroform and methanol as eluent. There was thus obtained 4-hydroxy-6-methyl-2-phthalimidomethylpyrimidine (0.77 g), as a white solid. NMR Spectrum: ($CD_3SOCD_3$) 2.06 (s, 3H), 4.67 (s, 2H), 6.06 (s, 1H), 7.9 (m, 4H).

Hydrazine hydrate (0.09 ml) was added to a suspension of the product so obtained (0.48 g) in methanol (20 ml) and the mixture was heated to reflux for 3 hours. The mixture was filtered and the filtrate was evaporated. A mixture of the solid so obtained and 2N aqueous hydrochloric acid solution was heated to 40° C. for 20 minutes. The mixture was filtered and the filtrate was evaporated. There was thus obtained the required starting material, as an orange solid (0.32 g).

(xv) 4-Aminomethyl-2,6-dioxopyrimidine is described in *Acta Pol. Pharm.*, 1970, 27, 341.

EXAMPLE 7

Using the process described in Example 5, p-[N-(3,4-dihydro-2-methyl-4-oxoquinazolin-6-ylmethyl)-N-ethylamino]benzoyl azide was reacted with (1-benzylimidazol-2-yl)methylamine to give N-(1-benzylimidazol-2-yl)methyl-p-[N-(3,4-dihydro-2-methyl-4-oxoquinazolin-6-ylmethyl)-N-ethylamino]benzamide (containing 1.3 equivalents of water) in 21% yield, m.p. 217°–221° C.

EXAMPLE 8

The process described in Example 5 was repeated using the appropriate benzoyl azide and the appropriate alcohol in place of 3-nitrobenzyl alcohol. There were thus obtained the compounds described in the following table, the structures of which were confirmed by proton magnetic resonance and mass spectroscopy and by elemental analysis.

TABLE V

Structure: HN-C(=O)-[phenyl with $H_3C$-C=N-]-CH₂-N(R²)-[phenyl]-CO.O-Y · $xH_2O$

| Ex. 8 Cmpd. No. (Note) | R² | Y | x | m.p. (°C.) |
|---|---|---|---|---|
| 1 | prop-2-ynyl | (1-benzylimidazol-2-yl)methyl | 0.8 | 205–209 |
| 2(1) | Me | [1-(2-nitrobenzyl)-imidazol-2-yl]methyl | 2.5 | 113–115 |
| 3(1) | Me | [1-(4-nitrobenzyl)-imidazol-2-yl]methyl | — | gum |
| 4 | prop-2-ynyl | (1-benzyl-4-ethoxy-carbonylimidazol-2-yl)methyl | 1 | 215–217 |
| 5 | prop-2-ynyl | (1-benzyl-4-carbamoyl-imidazol-2-yl)methyl | — | 170–173 |
| 6(1) | Me | 1,2,4-triazol-1-ylmethyl | 0.5 | 286–290 |
| 7 | Et | 1,2,4-triazol-1-ylmethyl | 1 | 231–235 |
| 8 | prop-2-ynyl | 1,2,4-triazol-1-ylmethyl | 0.5 | 248–250 |
| 9(2) | prop-2-ynyl | (1-benzylimidazol-4-yl)methyl | 1 | salt |

NOTES (1)p-[N-(3,4-Dihdro-2-methyl-4-oxoquinazolin-6-ylmethyl)-N-methylamino]benzoic acid. used as the starting material for the appropriate benzoyl azide, was prepared as follows: A mixture of 6-bromomethyl-2-methylquinazolin-4-one (15 g, prepared as described in UK Patent Specification No. 2188319A), 4-methylaminobenzoic acid (18 g) and dimethylformamide (150 ml) was heated to 60° C. for 16 hours. mixture was cooled to laboratory temperature and the precipitate was filtered off, washed with dimethylformamide (100 ml) and dried. The solid was dissolved in trifluoroacetic acid (100 ml) and the solution was evaporated. The resultant salt was triturated under ethyl acetate, filtered off and dried. There was thus obtained the required benzoic acid (as its trifluoroacetic acid salt; 17 g).

(2)The product also contained two equivalents of trifluoroacetic acid and showed the following characteristic NMR signals ($CD_3SOCD_3$) 2.36(s, 3H), 3.21(t, 1H), 4.36(d, 2H), 4.81(s, 2H), 5.25(s, 3H), 5.39(s, 2H), 6.85(m, 2H), 7.35–7.96(m, 12H), 9.1(m, 1H).

Information concerning the preparation of the necessary amine starting materials is provided below:

(i) The procedure described in *J. Amer. Chem. Soc.*, 1949, 383 was repeated except that 2-nitrobenzyl bromide was used in place of benzyl bromide. There was thus obtained 2-hydroxymethyl-1-(2-nitrobenzyl)imidazole which showed the following NMR signals (CDCl₃) 4.65 (s, 2H), 5.69 (s, 2H), 6.71–7.62 (m, 5H), 8.19 (m, 1H).

(ii) The procedure described in *J. Amer. Chem. Soc.*, 1949, 383 was repeated except that 4-nitrobenzyl bromide was used in place of benzyl bromide. There was thus obtained 2-hydroxymethyl-1-(4-nitrobenzyl)imidazole which showed the following NMR signals (CDCl₃) 4.62 (s, 2H), 5.37 (s, 2H), 6.85 (d, 1H), 6.95 (d, 1H), 7.3 (d, 2H), 8.2 (d, 2H).

(iii) Using the procedure described in *J. Amer. Chem. Soc.*, 1949, 383, ethyl imidazole-4-carboxylate was converted into ethyl 1-benzyl-2-hydroxymethylimidazole-4-carboxylate which showed the following NMR signals (CDCl₃) 1.35 (t, 2H), 2.95 (s, 1H), 4.32 (q, 3H), 4.72 (s, 2H), 5.26 (s, 2H), 7.14–7.4 (m, 5H), 7.51 (s, 1H).

(iv) A mixture of ethyl 1-benzyl-2-hydroxymethylimidazole-4-carboxylate (described immediately above, 1 g), an aqueous ammonium hydroxide solution (specific gravity 0.88 g/ml, 60 ml) and ethanol (25 ml) was stirred at laboratory temperature for 48 hours and then heated to 50° C. for 4 hours. The mixture was evaporated to give 1-benzyl-2-hydroxymethylimidazole-4-carboxamide, m.p. 204°–207° C.

(v) 1-Hydroxymethyl-1,2,4-triazole is described in European Patent Specification No. 0060222.

(vi) 1-Benzyl-4-hydroxymethylimidazole was prepared as follows:

Ethyl imidazole-4-carboxylate (15 g) was added to a suspension of sodium hydride (55% w/w dispersion in mineral oil, 4.7 g) in dimethylformamide (50 ml) which had been cooled to 0° C. The mixture was stirred at 0° C. for 1 hour. A solution of benzyl bromide (15 ml) in dimethylformamide (75 ml) was added and the mixture was stirred at laboratory temperature for 60 minutes. The mixture was poured onto ice (800 ml) and extracted with chloroform. The organic phase was dried (MgSO$_4$) and evaporated. The residue was purified by column chromatography on silica gel using a 4:1 v/v mixture of chloroform and hexane as eluent. There was thus obtained ethyl 1-benzylimidazole-4-carboxylate (17 g).

Lithium aluminium hydride (1M solution in diethyl ether, 11 ml) was added to a solution of a portion (2.3 g) of the product so obtained in diethyl ether (50 ml) and the mixture was stirred at laboratory temperature for 18 hours. Water (10 ml), aqueous sodium hydroxide solution (10%, 20 ml) and water (10 ml) were added in turn and the mixture was stirred for 15 minutes. The mixture was filtered and the filtrate was extracted with ethyl acetate. The organic layer was dried (MgSO$_4$) and evaporated. The residue was purified by column chromatography on silica gel using a 97:3 v/v mixture of chloroform and methanol as eluent. There was thus obtained the required starting material (1.2 g)

NMR Spectrum: (CDCl$_3$) 4.15 (s, 1H), 4.55 (s, 2H), 5.04 (s, 2H), 6.82 (d, 1H), 7.1–7.46 (m, 6H).

EXAMPLE 9

The process described in Example 5 was repeated using the appropriate benzoyl azide, and the appropriate amine in place of 3-nitrobenzyl alcohol. There were thus obtained the compounds described in the following table, the structures of which were confirmed by proton magnetic resonance and mass spectroscopy and by elemental analysis.

TABLE VI

Ex. 9

| Compd. No. (Note) | R$^2$ | Y | x | m.p. (°C.) |
|---|---|---|---|---|
| 1* | prop-2-ynyl | 3-methylbenzyl | 0.7 | 196–198 |
| 2* | prop-2-ynyl | 3-methoxybenzyl | — | 214–216 |
| 3* | prop-2-ynyl | 3-trifluoromethylbenzyl | 0.5 | 237–238 |
| 4(1) | prop-2-ynyl | 3-cyanobenzyl | 0.8 | 245–246 |
| 5* | Me | 3-nitrobenzyl | — | 250–253 |

NOTES
*The product was purified by column chromatography on silica gel using increasingly polar mixtures of methylene chloride and ethanol as eluent.
(1)3-Cyanobenzylamine is described in J. Med. Chem., 27, 1111.

EXAMPLE 10

Oxalyl chloride (0.114 ml) was added dropwise to a stirred solution of p-[N-(3,4-dihydro-2-methyl-3-pivaloyloxymethyl-4-oxoquinazolin-6-ylmethyl)-N-(prop-2-ynyl)amino]benzoic acid (0.39 g) in a mixture of methylene chloride (15 ml) and one drop of dimethylformamide which had been cooled to approximately 0° C. After an initial vigorous reaction, the pale yellow suspension was stirred at 20° C. for 2 hours. The mixture was evaporated, the residue was resuspended in methylene chloride (15 ml) and the mixture was cooled to 5° C. A mixture of triethylamine (0.36 ml) and 4-fluorobenzylamine (0.11 g) in methylene chloride (2 ml) was added and the clear solution was stirred at 20° C. for 18 hours. The solution was washed with water (2×15 ml), dried (MgSO$_4$) and evaportaed. The residue was purified by column chromatography on silica gel using increasingly polar mixtures of ethyl acetate and petrol (b.p. 60°–80° C.) as eluent. There was thus obtained p-[N-(3,4-dihydro-2-methyl-3-pivaloyloxymethyl-4-oxoquinazolin-6-ylmethyl)-N-(prop-2-ynyl)amino]-N-(4-fluorobenzyl)benzamide, as a pale yellow oil (242 mg).

The product so obtained was dissolved in ethanol (5 ml) and aqueous 2N sodium hydroxide solution was added. The solution was stirred at laboratory temperature for 2 hours. The mixture was evaporated and the residue was taken up in distilled water (10 ml). The mixture was acidified to pH3 by the addition of 1N aqueous hydrochloric acid solution. The precipitate was filtered off, washed with water (3×5 ml), and dried in vacuo at 70° C. for 4 hours. There were thus obtained p-[N-(3,4-dihydro-2-methyl-4-oxoquinazolin-6-ylmethyl)-N-(prop)-2-ynyl)amino]-N-(4-fluorobenzyl)benzamide (containing 0.75 equivalents of water, 0.13 g), m.p. 208°–210° C. NMR Spectrum: (CD$_3$SOCD$_3$) 2.35 (s, 3H, CH$_3$), 3.18 (t, 1H, J=1.5 Hz, C≡CH), 4.32 (broad s, 2H, CH$_2$), 4.41 (d, 2H, J=6 Hz, NHCH$_2$), 4.77 (s, 2H, CH$_2$), 6.84 (d, 2H, J=8 Hz, aromatic), 7.05–7.17 (m, 2H, aromatic), 7.25–7.38 (m, 2H, aromatic), 7.54 (d, 1H, J=6 Hz, aromatic), 7.68 (d of d's, 1H, J=6 and 2 Hz, aromatic), 7.75 (d, 1H, J=8 Hz, aromatic), 7.98 (d, 1H, J=2 Hz, aromatic), 8.68 (t, 1H, J=6 Hz, CONHCH$_2$);

Mass Spectrum: (positive ion FAB) m/e (P+1) 455;

Elemental Analysis: Found C, 68.5; H, 5.4; N, 12.3; C$_{26}$H$_{23}$N$_4$O$_2$F. 0.75 H$_2$O requires C, 68.6; H, 5.0; N, 11.6%

The p-[N-(3,4-dihydro-2-methyl-3-pivaloyloxymethyl-4-oxoquinazolin-6-ylmethyl)-N-(prop-2-ynyl)amino]-benzoic acid, used as a starting material, was obtained as follows:

Sodium hydride (6.62 g of a 50% w/w dispersion in mineral oil) was added portionwise to a cold (0°–50° C.; ice-bath), stirred solution of 2,6-dimethylquinazolin-4-one (20.0 g) in dimethylformamide (125 ml). The mixture was stirred at 5° C. for 1 hour. Chloromethyl pivalate (19.8 ml) was added in one portion and the creamy mixture was allowed to warm to laboratory temperature and was stirred for a further 18 hours. The mixture was cooled to 10° C. and aqueous 1N hydrochloric acid solution was added (45 ml). Ethyl acetate (200 ml) was added and the organic layer was separated and combined with further ethyl acetate extracts (2×100 ml). The combined organic fractions were washed with water (3×200 ml), dried and evaporated. The residue was triturated with cold hexane and the white solid was filtered off, washed with hexane and dried. There was thus obtained 3-(pivaloyloxymethyl)-2,6-dimethylquinazolin-4-one (17.22 g), m.p. 95°–98° C.

NMR Spectrum: (CDCl$_3$) 1.24 (s, 9H, 3×CH$_3$), 2.48 (s, 3H, ArCH$_3$), 2.63 (s, 3H, ArCH$_3$), 6.13 (s, 2H, OCH$_2$N), 7.52 (d, 1H, J=8 Hz, aromatic), 7.57 (d of d's, 1H, J=8 and 1.5 Hz, aromatic), 8.05 (d, 1H, J=1.5 Hz, aromatic);

Mass Spectrum: m/e (P) 288.

The product so obtained (15.02 g) was dissolved in warm carbon tetrachloride (280 ml) and powdered N-bromosuccinimide (9.8 g) and benzoyl peroxide (0.2 g) were added successively. The mixture was stirred vigorously and heated to reflux for 3.5 hours. The hot solution was filtered and the filtrate was evaporated to leave a residue which was triturated with cold hexane. The white solid was filtered off and dried. There was thus obtained 6-bromomethyl-2-methyl-3-pivaloyloxymethylquinazolin-4-one (11.72 g), NMR Spectrum: (CDCl$_3$) 1.22 (s, 9H, 3×CH$_3$), 2.65 (s, 3H, ArCH$_3$), 4.58 (s, 2H, CH$_2$Br), 6.12 (s, 2H, OCH$_2$N), 7.53 (d, 1H, J=8.5 Hz, aromatic), 7.79 (d of d's, 1H, J=8.5 and 2 Hz, aromatic), 8.27 (d, 1H, J=2 Hz, aromatic);

Mass Spectrum: (positive ion FAB) m/e (P+1) 367.

After repetition of the above reaction steps, 2,6-lutidine (10 ml) was added to a mixture of the product so obtained (39.6 g), tert-butyl p-[N-(prop-2-ynyl)amino]-benzoate (20.0 g) and dimethylformamide (280 ml). The solution was heated to 70°–75° C. for 18 hours. The brown solution was cooled to laboratory temperature and poured onto a mixture of ice and water (1 L). The mixture was filtered and the residue was washed with cold water (2×100 ml) and dried. The solid was triturated in cold diethyl ether (300 ml). The white solid was filtered off, washed with ether (2×50 ml) and dried. There was thus obtained tert-butyl p-[N-(3,4-dihydro-2-methyl-3-pivaloyloxymethyl-4-oxoquinazolin-6-ylmethyl)-N-(prop-2-ynyl)-amino]benzoate (28.6 g).

NMR Spectrum: (CDCl$_3$) 1.23 (s, 9H, 3×CH$_3$), 1.55 (s, 9H, 3×CH$_3$), 2.27 (t, 1H, J=1.5 Hz, C≡CH), 2.63 (s, 3H, ArCH$_3$), 4.17 (broad s, 2H, CH$_2$), 4.73 (s, 2H, CH$_2$), 6.11 (s, 2H, OCH$_2$N), 6.81 (d, 2H, J=8 Hz, aromatic), 7.59 (d, 1H, J=8 Hz, aromatic), 7.67 (d of d's, 1H, J=8 and 1.5 Hz, aromatic), 7.87 (d, 2H, J=8 Hz, aromatic), 8.18 (d, 1H, J=1.5 Hz, aromatic);

Mass Spectrum: m/e (P) 517.

The product so obtained (28 g) was added in portions to stirred trifluoroacetic acid (100 ml) and the solution was stirred at laboratory temperature under an argon atmosphere for 3 hours. Evaporation left a residue which was triturated under diethyl ether (350 ml). The precipitate was filtered off, washed with cold ether (2×50 ml) and dried to give an off-white solid. There was thus obtained p-[N-(3,4-dihydro-2-methyl-3-pivaloyloxymethyl-4-oxoquinazolin-6-ylmethyl)-N-(prop-2-ynyl)amino]benzoic acid (containing 0.7 equivalents of trifluoroacetic acid, 21.0 g), m.p. 143° C.

NMR Spectrum: (CDCl$_3$) 1.23 (s, 9H, 3×CH$_3$), 2.32 (t, 1H, J=1 Hz, C≡CH), 2.65 (s, 3H, ArCH$_3$), 4.19 (broad s, 2H, CH$_2$), 4.79 (s, 2H, CH$_2$), 6.12 (s, 2H, OCH$_2$N), 6.85 (d, 2H, J=8 Hz, aromatic), 7.64 (d, 1H, J=8 Hz, aromatic), 7.69 (d of d's, 1H, J=8 and 1.5 Hz, aromatic), 7.98 (d, 2H, J=8 Hz, aromatic), 8.18 (d, 1H, J=1.5 Hz, aromatic);

Mass Spectrum: (positive ion FAB) m/e (P+1) 462;

Elemental Analysis: Found C, 65.0; H, 5.9; N, 8.6; C$_{26}$H$_{27}$N$_3$O$_5$. 0.7 CF$_3$COOH requires C, 65.0; H, 5.5; N, 8.3%.

EXAMPLE 11

The process described in Example 10 was repeated using the appropriate amine or sulphonamide in place of 4-fluorobenzylamine. There were thus obtained the compounds described in the following table, the structures of which were confirmed by proton magnetic resonance and mass spectrometry and by elemental analysis.

TABLE VII

Ex. 11, structure: HN-C(=O)- attached to quinazoline with H$_3$C-N, containing CH$_2$-N(CH$_2$-C≡CH)- linked to phenyl-CONH-A-Y$^1$, xH$_2$O

| Compd. No. (Note) | A—Y$^1$ | x | m.p. (°C.) |
|---|---|---|---|
| 1 | 2-fluorophenyl | 1.5 | 235–237 |
| 2 | 3-fluorophenyl | 0.5 | 269–271 |
| 3 | 4-fluorophenyl | 1.5 | 249–252 |
| 4 | 4-carboxymethylphenyl | 1.8 | 270–274 |
| 5 | 4-(1-carboxyethyl)phenyl | 1.5 | 185–187 |
| 6 | 4-(carboxypropyl)phenyl | 3 | 290–295 |
| 7* | 2,4-difluorobenzyl | 1.5 | 211–213 |
| 8* | 2,6-difluorobenzyl | 1.3 | 198–200 |
| 9* | 4-sulphamoylphenyl | — | 275–278 |
| 10 | 2-(4-nitrophenyl)ethyl | 3.8 | 255–256 |
| 11 | 3-isoxazolylmethyl | — | 255–256 |
| 12+ | 4-nitrophenylsulphonyl | 3 | 155–160 |
| 13+ | 4-methoxyphenylsulphonyl | 1 | 260 |
| 14+ | 4-fluorophenylsulphonyl | 1.8 | 272–277 |
| 15 | 3-nitrophenyl | 1.5 | 195–205 |
| 16 | (2-chloropyrid-4-yl)methyl | — | 245–246 |
| 17 | (6-hydroxypyrid-2-yl)methyl | — | 267–272 |
| 18(1) | (2-benzimidazolyl)methyl | 1 | salt |

NOTES
*Elemental analysis showed that the product also contained 1 equivalent of sodium hydroxide.
+In these cases the appropriate arylsulphonamide was used in place of an amine. The pivaloyloxymethyl protecting group was removed using the following procedure: The appropriate acylsulphonamide so obtained was dissolved in methanol (50 ml) which had been saturated with gaseous ammonia. The mixture was stirred at laboratory temperature for 18 hours. The mixture was evaporated and the residue was purified by column chromatography on a reversed-phase preparative h.p.l.c. column (Dynamax 60 A) using decreasingly polar mixtures of methanol and water as eluent.
(1)The product was obtained as the hydrochloride salt and showed the following characteristic NMR signals (CD$_3$SOCD$_3$) 2.36(s,3H), 3.2(t, 1H), 4.38(d, 2H), 4.82(s, 2H), 6.89(m, 2H), 7.36-8.0(m, 9H), 9.09(m, 1H).

Information concerning the preparation of the amine starting materials is provided below:

(i) The preparation of 3-aminomethylisoxazole is described below:

Di-isobutylaluminium hydride (1.5M in toluene, 29 ml) was added to a solution of ethyl isoxazole-3-carboxylate (6.1 g; Can. J. Chem., 1970, 48, 475) in toluene (20 ml) which was cooled in an ice-bath. The mixture was stirred at laboratory temperature for 16 hours. The analysis indicated that the reduction was incomplete. A second portion of di-isobutylaluminium hydride (28.8 ml) was added and the mixture was stirred for 16 hours. The bulk of the toluene was evaporated and the mixture was poured into a saturated aqueous ammonium chloride solution. The precipitate was filtered off and dried. There was thus obtained 3-hydroxymethylisoxazole (2.1 g).

Thionyl chloride (4.2 ml) was added dropwise to a solution of the product so obtained in chloroform (20 ml) and the mixture was stirred at laboratory temperature for 1 hour. The mixture was evaporated and the crude 3-chloromethylisoxazole so obtained was used without further purification. The crude product was dissolved in dimethylacetamide (10 ml). Sodium carbonate (approx. 3 g) was added portionwise until the acidity of the reaction mixture was neutralised. Sodium azide (1 equivalent) was added and the mixture was stirred at laboratory temperature for 1.8 hours. The mixture was partitioned between ethyl acetate and water. The organic phase was dried (Na$_2$SO$_4$) and evaporated. The residue was purified by column chromatography on silica gel using a 1:1 v/v mixture of methylene chloride and hexane as eluent. There was thus obtained 3-azidomethylisoxazole (1.15 g). NMR Spectrum: (CD$_3$SOCD$_3$) 4.6 (s, 2H), 6.65 (d, 1H), 8.95 (d, 1H).

A mixture of the product so obtained, 10% palladium-on-charcoal catalyst (0.22 g) and ethyl acetate (10 ml) was stirred under an atmosphere of hydrogen for 2.5 hours. The mixture was filtered and the filtrate was evaporated. There was thus obtained 3-aminomethylisoxazole (0.93 g).

(ii) The preparation of methyl 4-(4-aminophenyl)butyrate is described below:

Thionyl chloride (6.9 ml) was added to 4-(4-nitrophenyl)butyric acid (10.0 g) which was heated to reflux for 2 hours. The clear solution was cooled and the excess of thionyl chloride was evaporated. The residue was dissolved in methylene chloride (25 ml) and added dropwise to a stirred mixture of methanol (7.6 ml) and pyridine (4.59 ml) in methylene chloride (100 ml) which had been cooled to $-5°$ C. by immersion in an ice-bath. The mixture was stirred at 20° C. for 18 hours, washed with dilute aqueous sodium bicarbonate solution, and with water and dried. There was thus obtained methyl 4-(4-nitrophenyl)butyrate (9.68 g).

The material so obtained was dissolved in a mixture of methanol (200 ml) and water (100 ml) and heated to reflux on a steam bath. Ferrous sulphate heptahydrate (11.71 g) and iron powder (34.0 g) were added and the mixture was heated to reflux for 6 hours. The solution was filtered whilst hot. Methanol was evaporated from the filtrate and the residual aqueous layer was extracted with ethyl acetate. The combined organic extracts were dried and evaporated to give a residue which was purified by column chromatography on silica gel using methylene chloride as eluent. There was thus obtained methyl 4-(4-aminophenyl)butyrate (6.22 g).

(iii) Methyl 2-(4-aminophenyl)propanoate was obtained from 2-(4-nitrophenyl)propionic acid by a procedure analoguous to that described immediately above.

(iv) The preparation of 4-fluorobenzenesulphonamide is described below:

A solution of 4-fluorobenzenesulphonyl chloride (2.0 g) in dry tetrahydrofuran (5 ml) was added dropwise to a cold (ice-bath), stirred solution of aqueous ammonia (S.G. 0.88, 20 ml). After the addition, stirring was continued for 30 minutes and the precipitated solid was filtered off, washed with water and dried in air. There was thus obtained 4-fluorobenzenesulphonamide (0.70 g).

(v) p-Methoxybenzenesulphonamide was obtained from 4-methoxybenzenesulphonyl chloride using the procedure described immediately above.

(vi) The preparation of 4-aminomethyl-2-chloropyridine is described below:

A mixture of 2-chloro-4-cyanopyridine (1.9 g), platinum dioxide (0.3 g), acetic anhydride (50 ml) and acetic acid (50 ml) was stirred under an atmosphere of hydrogen for 2 hours. The mixture was filtered and the filtrate was evaporated. The residue was partitioned between chloroform and dilute aqueous sodium bicarbonate solution. The organic phase was dried (MgSO$_4$) and evaporated to give N-(2-chloropyrid-4-ylmethyl)acetamide (1.5 g), as an oil.

A mixture of the product so obtained and 6N aqueous hydrochloric acid (72 ml) was heated to reflux for 21 hours. The mixture was evaporated and the residue was triturated in a 2:1 v/v mixture of methylene chloride and methanol. There was thus obtained the required starting material (0.53 g), as its hydrochloride salt. NMR Spectrum (CD$_3$SOCD$_3$) 4.10 (s, 2H), 7.55 (d, 1H), 7.69 (s, 1H), 8.46 (d, 1H), 8.68 (broad s, 2H).

(vii) The 2-aminomethyl-6-hydroxypyridine, used as a starting material, is described in U.S. Pat. No. 4,496,734.

EXAMPLE 12

Water (0.5 ml) and triethylamine (0.34 ml) were added to a mixture of p-[N-(3,4-dihydro-2-methyl-4-oxoquinazolin-6-ylmethyl)-N-(prop-2-ynyl)amino]benzoyl azide (0.15 g) and 3-aminosuccinimide (*J. Amer. Chem. Soc.*, 1954 76, 2467; 0.14 g) in dimethylsulfoxide (5 ml). The mixture was stirred at laboratory temperature for 10 days and evaporated. The residue was triturated with water, dried, triturated with diethyl ether and dried again. There was thus obtained p-[N-(3.4-dihydro-2-methyl-4-oxoquinazolin-6-ylmethyl-N-(prop-2-ynyl)amino]-N-(2.5-dioxopyrrolidin-3-yl)benzamide (containing 1 equivalent of water, 0.13 g), m.p. 164°–185° C. (decomposes).

NMR Spectrum: (CD$_3$SOCD$_3$) 2.32 (s, 3H, CH$_3$), 2.5–2.7 (m, 1H), 2.8–3.0 (m, 1H), 3.17 (s, 1H, C≡CH), 4.32 (s, 2H, CH$_2$), 4.79 (s, 2H, CH$_2$), 6.85 (d, 2H, J=8 Hz, aromatic), 7.54 (d, 1H, J=6 Hz, aromatic), 7.62–7.74 (m, 3H, aromatic), 7.96 (broad s, 1H, aromatic), 8.73 (d, 1H, J=6 Hz, CONH), 11.18 (s, 1H, CONHCO);

Mass Spectrum: (positive ion FAB) m/e (P+1) 443;

Elemental analysis: Found C, 62.7; H, 4.5; N, 14.8; C$_{24}$H$_{21}$N$_5$O$_4$. H$_2$O requires C, 62.4; H, 5.0; N, 15.2%.

EXAMPLE 13

A mixture of 6-bromomethyl-2-methylquinazolin-4-one (0.45 g), 2,6-lutidine (0.30 ml), N$^2$-(3-fluorophenyl)-4-ethylaminobenzohydrazide (0.48 g) and dimethylacetamide (10 ml) was heated to 80° C. for 4 hours. The mixture was cooled to laboratory temperature, poured into water (50 ml) and extracted with ethyl acetate (3×25 ml). The combined extracts were washed with water (2×25 ml), dried and evaporated to leave a residue which was purified by column chromatography on silica gel using increasingly polar mixtures of ethyl acetate and petrol (b.p. 60°–80° C.) as eluent. There was thus obtained N$^2$-(3-fluorophenyl)-p-[N-(3,4-dihydro-2-methyl-4-oxoquinazolin-6-ylmethyl)-N-ethylamino]-benzohydrazide (containing 1.5 equivalents of water, 0.11 g).

NMR Spectrum (CD$_3$SOCD$_3$): 1.15 (t, 2H, J=7 Hz, CH$_2$CH$_3$), 2.34 (s, 3H, CH$_3$), 3.35–3.70 (m, 3H, C≡CH and CH$_2$CH$_3$), 4.75 (broad s, 2H, CH$_2$), 6.40–6.80 (m, 5H, aromatic and NH), 7.10–7.35 (m, 1H, aromatic), 7.55–8.0 (m, 7H, aromatic and HH);

Mass Spectrum (positive ion FAB): m/e (P+1) 474;

Elemental Analysis: Found, C, 63.4; H, 5.6; N, 14.0; C$_{25}$H$_{24}$N$_5$O$_2$F. 1.5 H$_2$O requires C, 63.6; H, 5.8; N, 14.8%.

The N$^2$-(3-fluorophenyl)-p-ethylaminobenzohydrazide, used as a starting material, was obtained as follows:

A solution of 4-nitrobenzoyl chloride (3.58 g) in methylene chloride (50 ml) was added dropwise to a stirred mixture of 3-fluorophenylhydrazine hydrochloride (3.14 g), pyridine (3.12 ml) and methylene chloride (50 ml) which had been cooled to 5° C. The mixture was stirred at 5° C. for 1 hour and at 20° C. for 2 hours. The yellow precipitate was filtered off, washed with methylene chloride and dried. There was thus obtained $N^2$-(3-fluorophenyl)-p-nitrobenzohydrazide (3.25 g).

A solution of the product so obtained in acetic acid (40 ml) was heated to 80° C. and iron powder (7.26 g) was added portionwise. The mixture was stirred at 80° C. for 2.5 hours, cooled to laboratory temperature and filtered. The filtrate was washed with water (3×50 ml), dried ($MgSO_4$) and evaporated. There was thus obtained $N^2$-(3-fluorophenyl)-p-aminobenzohydrazide (2.29 g).

Using the procedure described in UK Patent Specification No. 2188319A for the N-alkylation of diethyl N-(4-aminobenzoyl)-L-glutamate, the hydrazide so obtained was reacted with ethyl iodide. There was thus obtained the required starting material (1.5 g).

EXAMPLE 14

Diphenylphosphoryl azide (0.09 ml) and triethylamine (0.12 ml) were added in turn to a solution of N-(4-carboxybenzyl)-p-[N-(3,4-dihydro-2-methyl-4-oxoquinazolin-6-ylmethyl)-N-(prop-2-ynyl)amino]benzamide (prepared as described in Example 2, 0.13 g) in dimethylsulfoxide (10 ml). The mixture was stirred at laboratory temperature for 45 minutes. Aqueous methylamine (33% w/v; 0.05 ml) was added and the mixture was stirred at laboratory temperature for 18 hours. The solution was poured into water (50 ml) and stirred. The precipitate was isolated, washed with water and dried. There was thus obtained p-[N-(3,4-dihydro-2-methyl-4-oxoquinazolin-6-ylmethyl)-N-(prop-2-ynyl)amino]-N-[4-(N-methylcarbamoyl)benzyl]benzamide (containing 1.3 equivalents of water, 79 mg), m.p. 260°–263° C.

NMR Spectrum: ($CD_3SOCD_3$) 2.32 (s, 3H, $CH_3$), 2.77 (d, 3H, J=4 Hz, $NHCH_3$), 3.17 (t, 1H, J=1.5 Hz, C≡CH), 4.31 (broad s, 2H, $CH_2$), 4.48 (d, 2H, J=6 Hz, $NHCH_2$), 4.76 (s, 2H, $CH_2$), 6.85 (d, 2H, J=8 Hz, aromatic), 7.34 (d, 2H, J=7 Hz), 7.53 (d, 1H, J=7 Hz, aromatic), 7.65–7.80 (m, 5H, aromatic), 7.97 (d, 1H, J=2 Hz, aromatic) 8.32 (broad hump, 1H, NH), 8.72 (t, 1H, J=6 Hz, NH);

Mass Spectrum (positive ion FAB): m/e (P+1) 494;

Elemental analysis: Found C, 67.8; H, 5.6; N, 13.2; $C_{29}H_{27}N_5O_3$. 1.3 $H_2O$ requires C, 67.5; H, 5.7; N, 13.6%.

EXAMPLE 15

Diphenylphosphoryl azide (0.55 ml) and triethylamine (1.3 ml) were added in turn to a mixture of p-[N-(3,4-dihydro-2-methyl-4-oxoquinazolin-6-ylmethyl)-N-(prop-2-ynyl)amino]-o-nitrobenzoic acid (0.457 g), 3-nitrobenzylamine hydrochloride (0.66 g) and dimethylacetamide (4 ml) and the mixture was stirred at laboratory temperature for 16 hours. The mixture was evaporated and the residue was triturated in water to give crude product as a solid. The aqueous mother liquors were extracted with ethyl acetate. The organic extract was dried ($MgSO_4$) and evaporated to give a second portion of crude product. The portions of product were combined and purified by column chromatography on silica gel using increasingly polar mixtures of methylene chloride and ethanol as eluent. The product was further purified by column chromatography on a reversed-phase h.p.l.c. column (Dynamax) eluting with a 3:2 v/v mixture of trifluoroacetic acid and water. There was thus obtained p-[N-(3,4-dihydro-2-methyl-4-oxoquinazolin-6-ylmethyl)-N-(prop-2-ynyl)amino]-o-nitro-N-(3-nitrobenzyl)benzamide (containing 0.3 equivalents of trifluoroacetic acid, 0.165 g), m.p. 258°–262° C. (decomposes);

Elemental Analysis: Found C, 58.9; H, 4.0; N, 13.9; $C_{27}H_{22}N_6O_6$. 0.3 $CF_3CO_2H$ requires C, 58.9; H, 4.0; N, 14.9%.

The p-[N-(3,4-dihydro-2-methyl-4-oxoquinazolin-6-ylmethyl)-N-(prop-2-ynyl)amino]-o-nitrobenzoic acid, used as a starting material, was obtained as follows:

A mixture of methyl 4-amino-2-nitrobenzoate (10.6 g: Chem. Abs., 98, 143133e), 2.6-lutidine (8.14 ml), prop-2-ynyl bromide (80% w/w solution in toluene: 7.82 ml) and dimethylacetamide (50 ml) was heated to 80° C. for 4 hours. A second portion of prop-2-ynyl bromide solution (7.82 ml) was added and the mixture was heated to 80° C. for 5 hours. The mixture was cooled to laboratory temperature and partitioned between ethyl acetate and water. The organic phase was dried ($MgSO_4$) and evaporated. The residue was purified by column chromatography on silica gel using methylene chloride as eluent. There was thus obtained methyl 2-nitro-4-(prop-2-ynylamino)benzoate (6.58 g), m.p. 134°–135° C.

A mixture of a portion (2 g) of the ester so obtained, 6-bromomethyl-3,4-dihydro-2-methylquinazolin-4-one (2.6 g), 2,6-lutidine (2 ml) and dimethylacetamide (10 ml) was heated to 80° C. for 4 hours. The mixture was cooled to laboratory temperature and partitioned between ethyl acetate and water. The organic phase was washed with water, dried ($MgSO_4$) and evaporated. The residue was triturated in ethyl acetate to give methyl p-[N-(3,4-dihydro-2-methyl-4-oxoquinazolin-6-ylmethyl)-N-(prop-2-ynyl)amino]-o-nitrobenzoate (1.52 g).

A mixture of the product so obtained, 1N aqueous sodium hydroxide solution (18.5 ml) and ethanol (18.5 ml) was stirred at laboratory temperature for 2 hours. The mixture was concentrated by evaporation to a volume of approximately 10 ml and acidified to pH1 by the addition of 2N aqueous hydrochloric acid solution. The precipitate was filtered off, washed with water and dried. There was thus obtained the required starting material (1.24 g), m.p. 260°–262° C.

EXAMPLE 16

The process described in Example 1 was repeated except that 6-aminomethyl-3,4-dihydro-2-methyl-3-pivaloyloxymethylquinazolin-4-one was used in place of 3-aminomethylpyridine. There was thus obtained p-[N-(3,4-dihydro-2-methyl-4-oxoquinazolin-6-ylmethyl)-N-(prop-2-ynyl)amino]-N-(3,4-dihydro-2-methyl-4-oxo-3-pivaloyloxymethylquinazolin-6-ylmethyl)benzamide (containing 1 equivalent of water, 96%), m.p. 191°–193° C. (Example 16, Compound No. 1).

A mixture of a portion (0.253 g) of the product so obtained, 1N aqueous sodium hydroxide solution (4 ml) and ethanol (12 ml) was stirred at laboratory temperature for 2 hours. The mixture was neutralised by the addition of 1N aqueous hydrochloric acid solution and the precipitate so formed was isolated, washed with water and with acetone and dried. There was thus obtained p-[N-(3,4-dihydro-2-methyl-4-oxoquinazolin-6-ylmethyl)-N-(prop-2-ynyl)amino]-N-(3,4-dihydro-2-methyl-4-oxoquinazolin-6-ylmethyl)benzamide (containing 0.7 equivalents of acetone and 0.8 equivalents of sodium hydroxide, 0.169 g), m.p. 284°–294° C.

NMR Spectrum: (CD₃SOCD₃) 2.34 (s, 6H), 3.17 (s, 1H, C≡CH), 4.32 (s, 2H, CH₂C≡CH), 4.54 (d, 2H, NHCH₂), 4.77 (s, 2H), 6.86–7.97 (m, 10H, aromatic), 8.79 (t, 1H, CONH). (Example 16, Compound No. 2).

The 6-aminomethyl-3,4-dihydro-2-methyl-3-pivaloyloxymethylquinazolin-4-one, used as a starting material, was obtained as follows:

Using the procedures described in the second and third paragraphs of Note (v), in the portion of Example 6 which is concerned with the preparation of starting materials, 6-bromomethyl-3,4-dihydro-2-methyl-3-pivaloyloxymethylquinazolin-4-one was reacted with potassium phthalimide and the resultant phthalimide was treated with hydrazine hydrate. There was thus obtained the required starting material, as its hydrochloride salt, in 75% yield. The salt so formed (5.6 g) was dissolved in water (20 ml) and the solution was basified to pH8 by the addition of 2N aqueous sodium hydroxide solution. The mixture was extracted with ethyl acetate (3×30 ml). The combined extracts were dried (MgSO₄) and evaporated. There was thus obtained the required free base starting material (1.04 g).

EXAMPLE 17

The process described in Example 1 was repeated except that 6-aminomethyl-3,4-dihydro-3-pivaloyloxymethylquinazolin-4-one was used in place of 3-aminomethylpyridine. There was thus obtained p-[N-(3,4-dihydro-2-methyl-4-oxoquinazolin-6-ylmethyl)-N-(prop-2-ynyl)amino]-N-(3,4-dihydro-4-oxo-3-pivaloyloxymethylquinazolin-6-ylmethyl)benzamide (48%), m.p. 165°–168° C. (Example 17, Compound No. 1).

A mixture of the product so obtained (0.18 g), 1N aqueous sodium hydroxide solution (2.3 ml) and ethanol (8 ml) was stirred at laboratory temperature for 16 hours. The bulk of the ethanol was evaporated, water (15 ml) was added and the mixture was acidified to pH5 by the addition of 2N aqueous hydrochloric acid solution. The gelatinous precipitate so formed was isolated by centrifugation, washed with water and dried. The crude product (0.21 g) so obtained was purified by column chromatography on silica gel using increasingly polar mixtures of methylene chloride and ethanol as eluent. There was thus obtained p-[N-(3,4-dihydro-2-methyl-4-oxoquinazolin-6-ylmethyl)-N-(prop-2-ynyl)amino]-N-(3,4-dihydro-4-oxoquinazolin-6-ylmethyl)benzamide (containing 0.25 equivalents of water and 1.5 equivalents of sodium hydroxide, 0.066 g), m.p. 192°–200° C.

NMR Spectrum (CD₃SOCD₃) 2.37 (s, 3H), 3.18 (s, 1H, C≡CH), 4.32 (s, 2H, CH₂C≡C), 4.57 (d, 2H, NHCH₂), 4.80 (s, 2H, ArCH₂), 6.87 (d, 2H, aromatic), 7.56–8.06 (m, 9H, aromatic), 8.83 (hump, 1H). (Example 17, Compound No. 2).

The 6-aminomethyl-3,4-dihydro-3-pivaloyloxymethylquinazolin-4-one, used as a starting material, was obtained from 6-bromomethyl-3,4-dihydro-3-pivaloyloxymethylquinazolin-4-one (*J. Med. Chem.*, 1989, 32, 847) using the procedure described in Note (x) below Table IV in Example 6 i.e. reaction with sodium azide and reduction of the azide so formed by hydrogenation. The reaction of the 6-bromomethyl derivative was carried out at laboratory temperature for 2.5 hours. The required starting material was obtained in 88% yield, as a white foam.

EXAMPLE 18

The process described in Example 10 was repeated except that 6-aminomethyl-3,4-dihydro-2,3-dimethylquinazolin-4-one was used in place of 4-fluorobenzylamine. There was thus obtained p-[N-(3,4-dihydro-2-methyl-4-oxoquinazolin-6-ylmethyl)-N-(prop-2-ynyl)amino]-N-(3,4-dihydro-2,3-dimethyl-4-oxoquinazolin-6-ylmethyl)benzamide (containing 2 equivalents of water, 24%), m.p. 210°–211° C.

The 6-aminomethyl-3,4-dihydro-2,3-dimethylquinazolin-4-one, used as a starting material, was obtained from 3,4-dihydro-2,3,6-trimethylquinazolin-4-one, as an oily solid in 25% overall yield, using the procedure described in Note (xiii) below Table IV in Example 6.

EXAMPLE 19

6-Bromomethyl-3,4-dihydro-2-methylquinazolin-4-one (0.56 g) and 2,6-lutidine (0.35 ml) were added in turn to a solution of N-(3-nitrobenzyl)-5-methylaminothiophene-2-carboxamide (0.43 g) in N-methylpyrrolidin-2-one (5 ml) and the mixture was heated to 90° C. for 4 hours. The mixture was poured into water (50 ml) and the resultant mixture was extracted with ethyl acetate. The organic phase was washed with water, dried (Na₂SO₄) and evaporated. The residue was purified by column chromatography on silica gel using ethyl acetate and then a 19:1 v/v mixture of ethyl acetate and methanol as eluent. There was thus obtained 5-[N-(3,4-dihydro-2-methyl-4-oxoquinazolin-6-ylmethyl)-N-methylamino]-N-(3-nitrobenzyl)thiophene-2-carboxamide (0.055 g), m.p. 155°–158° C.

The N-(3-nitrobenzyl)-5-methylaminothiophene-2-carboxamide, used as a starting material, was obtained as follows:

Triethylamine (2 ml), diphenylphosphoryl azide (2.5 ml) and 3-nitrobenzylamine (1.2 g) were each added in turn to a solution of 5-(N-tert-butoxycarbonyl-N-methylamino)thiophene-2-carboxylic acid (1.25 g) in dimethylformamide (30 ml) and the mixture was stirred at laboratory temperature for 18 hours. The mixture was poured into water (200 ml) and extracted with ethyl acetate (4×100 ml). The combined extracts were dried (Na₂SO₄) and evaporated. The residue was purified by column chromatography using a 4:1 v/v mixture of hexane and ethyl acetate as eluent. There was thus obtained 5-(N-tert-butoxycarbonyl-N-methylamino)-N-(3-nitrobenzyl)thiophene-2-carboxamide (1.95 g), as a yellow solid.

A portion (1 g) of the product so obtained was dissolved in trifluoroacetic acid (20 ml) and the solution was stirred at laboratory temperature for 2 hours. The solution was evaporated and the residue was partitioned between ethyl acetate and a saturated aqueous sodium bicarbonate solution. The organic phase was dried (Na₂SO₄) and evaporated. The residue was purified by column chromatography using a 4:1 v/v mixture of hexane and ethyl acetate as eluent. There was thus obtained the required starting material (0.43 g), as an oil.

EXAMPLE 20

The process described in Example 10 was repeated except that 2-[N-(4-hydroxypyrimidin-2-ylamino)ethyl]amine was used in place of 4-fluorobenzylamine. There was thus obtained p-[N-(3,4-dihydro-2-methyl-4-oxoquinazolin-6-ylmethyl)-N-(prop-2-ynyl)amino]-N-

[2-(4-hydroxypyrimidin-2-ylamino)ethyl]benzamide in 80% yield, m.p. >300° C. (decomposes).

NMR Spectrum: (CD$_3$SOCD$_3$) 2.33 (s, 3H), 3.18 (s, 1H), 3.40 (s, 4H), 4.32 (s, 2H), 4.78 (s, 2H), 5.53 (m, 1H), 6.8–8.2 (m, 9H).

The 2-[N-(4-hydroxypyrimidin-2-ylamino)ethyl]amine, used as a starting material, was obtained as follows:

A mixture of 4-hydroxy-2-methylthiopyrimidine (18.5 g) and 2-(benzyloxycarbonylamino)ethylamine (27.2 g) was heated to 140° C. for 2 hours. Ethyl acetate (200 ml) was added and the precipitate was filtered off. There was thus obtained 2-[2-(benzyloxycarbonylamino)ethylamino]-4-hydroxypyrimidine (22.7 g), m.p. 145°–146° C. (recrystallised from isopropanol).

A mixture of a portion (9.8 g) of the product so obtained, ammonium formate (4.3 g), 10% palladium-on-charcoal catalyst (1 g) and methanol (130 ml) was stirred at laboratory temperature for 18 hours. The mixture was filtered and the filtrate was evaporated to give the required starting material.

EXAMPLE 21

The process described in Example 12 was repeated except that 3-aminoglutarimide (*J. Amer. Chem. Soc.*, 1957, 79, 3767) was used in place of 3-aminosuccinimide. The crude reaction product was purified by column chromatography on reversed-phase silica gel (Dynamax) using a 40:60:0.2 v/v mixture of methanol: water: trifluoroacetic acid as eluent. There was thus obtained p-[N-(3,4-dihydro-2-methyl-4-oxoquinazolin-6-ylmethyl)-N-(prop-2-ynyl)amino]-N-(2,6-dioxopiperidin-3-yl)benzamide (containing 1.3 equivalents of trifluoroacetic acid, 32%), m.p. 161°–168° C.

NMR Spectrum: (CD$_3$SOCD$_3$) 2.02 (m, 2H), 2.40 (s, 3H), 2.52 (m, 1H), 2.77 (m, 1H), 3.18 (t, 1H), 4.33 (t, 2H), 4.72 (m, 1H), 4.83 (s, 2H), 6.86 (d, 2H), 7.56 (d, 1H), 7.71 (d, 2H), 7.72 (q, 1H), 8.01 (d, 1H), 8.39 (d, 1H), 10.77 (s, 1H);

Mass Spectrum: (positive ion FAB) m/e (P+1) 458;

Elemental Analysis: Found C, 54.8; H, 4.2; N, 11.4; C$_{25}$H$_{23}$N$_5$O$_4$.1.3CF$_3$CO$_2$H requires C, 54.7; H, 4.0; N, 11.6%.

EXAMPLE 22

Using the procedure described in Example 10, p-[N-(3,4-dihydro-3-pivaloyloxymethyl-4-oxoquinazolin-6-ylmethyl)-N-(prop-2-ynyl)amino]benzoic acid was reacted with 3-nitrobenzylamine to give p-[N-(3,4-dihydro-4-oxoquinazolin-6-ylmethyl)-N-(prop-2-ynyl)amino]-N-(3-nitrobenzyl)benzamide (containing 1 equivalent of water, 56%), m.p. 197°–199° C.

The p-[N-(3,4-dihydro-3-pivaloyloxymethyl-4-oxoquinazolin-6-ylmethyl)-N-(prop-2-ynyl)amino]benzoic acid, used as a starting material, was obtained by reacting 6-bromomethyl-3,4-dihydro-3-pivaloyloxymethylquinazolin-4-one [UK Patent Specification No. 2175903B] with tert-butyl p-(prop-2-ynylamino)benzoate and by treating the resultant product with trifluoroacetic acid. There was thus obtained the required starting material in 53% yield, m.p. 93°–96° C.

EXAMPLE 23

Using the procedure described in Example 10, p-[N-(3,4-dihydro-3-pivaloyloxymethyl-4-oxoquinazolin-6-ylmethyl)-N-(prop-2-ynyl)amino]benzoic acid was reacted with 3-aminomethylpyridine to give p-[N-(3,4-dihydro-4-oxoquinazolin-6-ylmethyl)-N-(prop-2-ynyl)amino]-N-(3-pyridylmethyl)benzamide (containing 4.5 equivalents of water, 61%), m.p. 137°–139° C.

EXAMPLE 24

The process described in Example 5 was repeated except that N-(cyanomethyl)-N-methylamine was used in place of 3-nitrobenzyl alcohol. The reaction mixture was stirred at laboratory temperature for 16 hours. The mixture was evaporated and the residue was purified by column chromatography on silica gel using increasingly polar mixtures of methylene chloride and ethanol as eluent. There was thus obtained p-[N-(3,4-dihydro-2-methyl-4-oxoquinazolin-6-ylmethyl)-N-(prop-2-ynyl)amino]-N-(cyanomethyl)-N-methylbenzamide (68%), m.p. 214°–215° C., and p-[N-(3,4-dihydro-2-methyl-4-oxoquinazolin-6-ylmethyl)-N-(prop-2-ynyl)amino]-N-[3-(hexahydro-2-oxoazepin-1-yl)propyl]benzamide (containing 0.5 equivalents of water; 23%), m.p. 208°–210° C., (this product arising from reaction of the benzoyl azide with 1,8-diazabicyclo[5.4.0]undec-7-ene).

EXAMPLE 25

Using the procedure described in Example 5, p-[N-(3,4-dihydro-2-methyl-4-oxoquinazolin-6-ylmethyl)-N-methylamino]benzoyl azide was treated with L-histidine. The mixture was stirred at laboratory temperature for 16 hours. The mixture was evaporated, the residue was dissolved in water and the solution was acidified to pH4 by the addition of 2N aqueous hydrochloric acid. The precipitate so formed was isolated by centrifugation and purified by column chromatography on silica gel using a 9:1 v/v mixture of chloroform and methanol as eluent. There were thus obtained p-[N-(3,4-dihydro-2-methyl-4-oxoquinazolin-6-ylmethyl)-N-methylamino]-N-[3-(hexahydro-2-oxoazepin-1-yl)propyl]benzamide (containing 1.8 equivalents of water; 15%), m.p. 155°–157° C., (the product arising from reaction of the benzoyl azide with 1,8-diazabicyclo[5.4.0]undec-7-ene).

EXAMPLE 26

Using the procedure described in Example 10, p-[N-(3,4-dihydro-7-fluoro-2-methyl-3-pivaloyloxymethyl-4-oxoquinazolin-6-ylmethyl)-N-(prop-2-ynyl)amino]benzoic acid was reacted with 3-nitrobenzylamine. There was thus obtained p-[N-(3,4-dihydro-7-fluoro-2-methyl-4-oxoquinazolin-6-ylmethyl)-N-(prop-2-ynyl)amino]-N-(3-nitrobenzyl)benzamide (containing 1.5 equivalents of water, 76%, m.p. 235°–237° C.

The p-[N-(3,4-dihydro-7-fluoro-2-methyl-3-pivaloyloxymethyl-4-oxoquinazolin-6-ylmethyl)-N-(prop-2-ynyl)amino]benzoic acid, used as a starting material, was obtained as follows:

3,4-Dihydro-7-fluoro-2,6-dimethylquinazolin-4-one was prepared from 3-fluoro-4-methylacetanilide using the procedure described in UK Patent Specification No. 2202847A for the preparation of 3,4-dihydro-2,6,7-trimethylquinazolin-4-one from 3,4-dimethylacetanilide.

Using the procedure described in the four paragraphs of the portion of Example 10 which is concerned with the preparation of starting materials, the product so obtained was converted in 15% yield to p-[N-(3,4-dihydro-7-fluoro-2-methyl-3-pivaloyloxymethyl-4-oxoquinazolin-6-ylmethyl)-N-(prop-2-ynyl)amino]benzoic acid, m.p. 173°–174° C.

EXAMPLE 27

The procedure described in Example 26 was repeated except that 3-aminomethylpyridine was used in place of 3-nitrobenzylamine. There was thus obtained p-[N-(3,4-dihydro-7-fluoro-2-methyl-4-oxoquinazolin-6-ylmethyl)-N-(prop-2-ynyl)amino]-N-(3-pyridylmethyl)benzamide (containing one equivalent of water), m.p. 251°–253° C.

The procedure described immediately above was repeated except that 3-cyanobenzylamine was used in place of 3-aminomethylpyridine. There was thus obtained N-(3-cyanobenzyl)-p-[N-(3,4-dihydro-7-fluoro-2-methyl-4-oxoquinazolin-6-ylmethyl)-N-(prop-2-ynyl)amino]benzamide (containing 0.75 equivalents of water), m.p. 232° C.

EXAMPLE 28

Using the procedure described in Example 10, p-[N-(3,4-dihydro-2-methyl-4-oxo-3-pivaloyloxymethyl-quinazolin-6-ylmethyl)-N-(2-acetoxyethyl)amino]benzoic acid was reacted with 3-nitrobenzylamine to give p-[N-(3,4-dihydro-2-methyl-4-oxoquinazolin-6-ylmethyl)-N-(2-hydroxyethyl)amino-N-(3-nitrobenzyl)benzamide (containing 1 equivalent of water) in 46% yield, m.p. 230°–232° C.

The p-[N-(3,4-dihydro-2-methyl-4-oxo-3-pivaloyloxymethylquinazolin-6-ylmethyl-N-(2-acetoxyethyl)amino]benzoic acid, used as a starting material, was obtained by reacting 6-bromomethyl-3,4-dihydro-3-pivaloyloxymethylquinazolin-4-one [UK Patent Specification No. 2175903B] with tert-butyl p-(2-acetoxyethylamino)benzoate [prepared by the reaction of tert-butyl p-aminobenzoate with 2-acetoxyethyl bromide and by treating the resultant product with trifluoroacetic acid]. There was thus obtained the required starting material as a foam.

EXAMPLE 29

Using the procedure described in Example 10, p-[N-(3,4-dihydro-2-methyl-4-oxo-3-pivaloyloxymethyl-quinazolin-6-ylmethyl)-N-2-acetoxyethyl)amino]benzoic acid was reacted with 3-cyanobenzylamine to give N-(3-cyanobenzyl)-p-[N-(3,4-dihydro-2-methyl-4-oxoquinazolin-6-ylmethyl)-N-(2-hydroxyethyl)amino]-benzamide, m.p. 110°–112° C., as a foam.

EXAMPLE 30

The procedure described in Example 10 was repeated except that 2-aminomethylquinoxaline was used in place of 4-fluorobenzylamine. There was thus obtained p-[N-(3,4-dihydro-2-methyl-3-pivaloyloxymethyl-4-oxoquinazolin-6-ylmethyl)-N-(prop-2-ynyl)amino]-N-(quinoxalin-2-ylmethyl)benzamide in 23% yield, m.p. 126° C.

The 2-aminomethylquinoxaline, used as a starting material, was obtained from 2-bromomethylquinoxaline using the procedure described in Note (2) below Table I in Example 1.

EXAMPLE 31

Using the procedure described in Example 1, o-amino-p-[N-(3,4-dihydro-2-methyl-4-oxoquinazolin-6-ylmethyl)-N-(prop-2-ynyl)amino]benzoic acid was reacted with 3-nitrobenzylamine to give o-amino-p-[N-(3,4-dihydro-2-methyl-4-oxoquinazolin-6-ylmethyl)-N-(prop-2-ynyl)amino]-N-(3-nitrobenzyl)benzamide in 64% yield, m.p. 86°–92° C.

The o-amino-p-[N-(3,4-dihydro-2-methyl-4-oxoquinazolin-6-ylmethyl)-N-(prop-2-ynyl)amino]benzoic acid, used as a starting material, was obtained as follows:

A mixture of methyl p-[N-(3,4-dihydro-2-methyl-4-oxoquinazolin-6-ylmethyl)-N-(prop-2-ynyl)amino]-o-nitrobenzoate (0.3 g), activated iron powder [1.24 g: activated by stirring a mixture of iron powder and 2N aqueous hydrochloric acid solution for 5 minutes filtering the mixture and washing the iron with methanol], methanol (10 ml) and concentrated hydrochloric acid (20 drops) was heated to reflux for 80 minutes. The mixture was cooled to laboratory temperature and partitioned between ethyl acetate and a saturated aqueous sodium bicarbonate solution. The organic phase was washed with water, dried and evaporated. The residue was purified by column chromatography on silica gel using increasingly polar mixtures of methylene chloride and methanol as eluent. There was thus obtained methyl o-amino-p-[N-(3,4-dihydro-2-methyl-4-oxoquinazolin-6-ylmethyl)-N-(prop-2-ynyl)amino]benzoate (0.1 g, 36%).

A mixture of the product so obtained, 1N aqueous sodium hydroxide solution (0.72 ml) and propanol (2 ml) was heated to 80° C. for 30 minutes. The mixture was evaporated, water (2 ml) was added and the mixture was acidified to pH 3.5 by the addition of 2N aqueous hydrochloric acid solution. The precipitate was isolated by centrifugation and dried. There was thus obtained the required starting material (0.9 g, 94%).

EXAMPLE 32

The procedure described in Example 5 was repeated except that 3-aminomethylpyridine-N-oxide (J. Med. Chem., 1987, 30, 2222) was used in place of 3-nitrobenzyl alcohol. The reaction mixture was evaporated, the residue was dissolved in water and the solution was acidified to pH5 by the addition of 2N aqueous hydrochloric acid solution. The precipitate was filtered off, dried and purified by column chromatography using increasingly polar mixtures of methylene chloride and ethanol as eluent. There was thus obtained p-[N-(3,4-dihydro-2-methyl-4-oxoquinazolin-6-ylmethyl)-N-(prop-2-ynyl)amino]-N-(N-oxidopyrid-3-ylmethyl)benzamide (0.60 g, 66%), m.p. 170°–171° C.

EXAMPLE 33

A mixture of pentafluorophenyl p-[N-(3,4-dihydro-2-methyl-4-oxo-3-pivaloyloxymethylquinazolin-6-ylmethyl)-N-(prop-2-ynyl)amino]benzoate (0.2 g), 4-aminomethyl-2-hydroxypyridine (0.081 g), triethylamine (0.19 ml), N-hydroxybenzotriazole (1 drop) and dimethylformamide (40 ml) was stirred at laboratory temperature for 16 hours. The mixture was evaporated and the residue was triturated in diethyl ether. There was thus obtained p-[N-(3,4-dihydro-2-methyl-4-oxo-3-pivaloyloxymethylquinazolin-6-ylmethyl)-N-(prop-2-ynyl)amino]-N-(2-hydroxypyrid-4-ylmethyl)benzamide in quantitative yield, m.p. 145° C.

A mixture of the product so obtained, a saturated aqueous ammonium hydroxide solution (7.4 ml) and methanol (15 ml) was stirred at laboratory temperature for 16 hours. The mixture was concentrated by evaporation of the methanol. The precipitate was filtered off and dried. There was thus obtained p-[N-(3,4-dihydro-2-methyl-4-oxoquinazolin-6-ylmethyl)-N-(prop-2-ynyl)amino]-N-(2-hydroxypyrid-4-ylmethyl)benzamide (0.14 g), as a white solid.

NMR Spectrum (CD₃SOCD₃) 2.33 (s, 3H), 3.18 (s, 1H), 4.23 (d, 2H), 4.32 (broad s, 2H), 4.78 (s, 2H), 6.09 (d, 1H), 6.13 (s, 1H), 6.87 (d, 2H), 7.27 (d, 1H), 7.53 (d, 1H), 7.5 (d of d's, 1H), 7.76 (d, 2H), 7.97 (s, 1H), 8.63 (broad s, 1H), 11.32 (broad s, 1H), 12.13 (broad s, 1H).

The pentafluorophenyl p-[N-(3,4-dihydro-2-methyl-4-oxo-3-pivaloyloxymethylquinazolin-6-ylmethyl)-N-(prop-2-ynyl)amino]benzoate, used as a starting material, was obtained as follows:

Dicyclohexylcarbodiimide (6.18 g), was added to a suspension of p-[N-(3,4-dihydro-2-methyl-4-oxo-3-pivaloyloxymethylquinazolin-6-ylmethyl)-N-(prop-2-ynyl)amino]benzoic acid (13.83 g) pentafluorophenol (5.52 g) in ethyl acetate (450 ml) and the mixture was stirred at laboratory temperature for 18 hours. The mixture was filtered and the filtrate was evaporated. The residue was purified by column chromatography on silica gel using a 1:1 v/v mixture of hexane and ethyl acetate as eluent. There was thus obtained the required starting material (13.9 g), m.p. 143°–144° C.

The 4-aminomethyl-2-hydroxypyridine, used as a starting material, was obtained as follows:

A mixture of 2-chloro-4-cyanopyridine (7.7 g), platinum dioxide (1.1 g), acetic anhydride (77 ml) and acetic acid (77 ml) was stirred at laboratory temperature under an atmosphere of hydrogen for five hours. The mixture was filtered and the filtrate was evaporated. The residue was purified by column chromatography using increasingly polar mixtures of hexane and ethyl acetate as eluent. There was thus obtained 4-acetamidomethyl-2-chloropyridine (2.4 g), m.p. 83° C.

A mixture of a portion (1.6 g) of the product so obtained and concentrated hydrochloric acid (20 ml) was heated to reflux for four days. The mixture was evaporated to give the required starting material (1.1 g, recrystallised from ethanol).

NMR Spectrum (CD₃SOCD₃) 3.89 (q, 2H), 6.42 (d, 1H), 6.52 (s, 1H), 7.49 (d, 1H), 8.68 (broad s, 3H).

EXAMPLE 34

The procedure described in Example 33 was repeated except that 3-aminomethyl-6-hydroxypyridine was used in place of 4-aminomethyl-2-hydroxypyridine. There was thus obtained p-[N-(3,4-dihydro-2-methyl-4-oxoquinazolin-6-ylmethyl)-N-(prop-2-ynyl)amino]-N-(6-hydroxypyrid-3-ylmethyl)benzamide in 64% yield, m.p. 258° C.

The 3-aminomethyl-6-hydroxypyridine, used as a starting material, was obtained from 3-cyano-6-methoxypyridine using the procedure described in the portion of Example 33 which is concerned with the preparation of 4-aminomethyl-2-hydroxypyridine except that, in the second step described therein, 48% aqueous hydrobromic acid was used in place of concentrated hydrochloric acid. There was thus obtained the required starting material, as the hydrobromide salt, m.p. 239° C.

EXAMPLE 35

The procedure described in Example 5 was repeated except that 4-aminomethylpiperidine was used in place of 3-nitrobenzyl alcohol to give p-[N-(3,4-dihydro-2-methyl-4-oxoquinazolin-6-ylmethy)-N-(prop-2-ynyl-)amino]-N-(piperidin-4-ylmethyl)benzamide (containing 3.5 equivalents of water), m.p. 130°–133° C. (decomposes).

EXAMPLE 36

The procedure described in Example 5 was repeated except that 2-aminomethyl-N-ethylpyrrolidine was used in place of 3-nitrobenzyl alcohol. There was thus obtained p-[N-(3,4-dihydro-2-methyl-4-oxoquinazolin-6-ylmethyl)-N-(prop-2-ynyl)amino]-N-(N-ethylpyrrolidin-2-ylmethyl)benzamide (containing 1.3 equivalents of water), m.p. 139°–143° C. (decomposes).

EXAMPLE 37

The following illustrate representative pharmaceutical dosage forms containing the compound of formula I, or a pharmaceutically-acceptable salt salt therof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 mg |
| Lactose Ph.Eur | 488.5 |
| Magnesium stearate | 1.5 |

| (e) Injection I | (50 mg/ml) |
|---|---|
| Compound X | 5.0% w/v |
| 1M Sodium hydroxide solution | 15.0% w/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

The above formulations may be obtained by conventional procedures well known in the pharmaceutical art. The tablets (a) to (c) may be enteric coated by conventional means, for example to provide a coating of cellulose acetate phthalate.

CHEMICAL FORMULAE

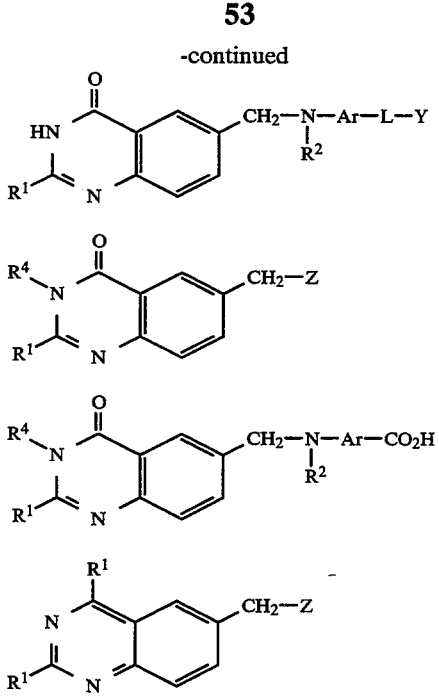

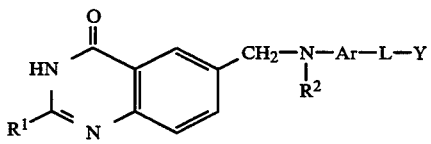

What we claim is:

1. A quinazoline of the formula I

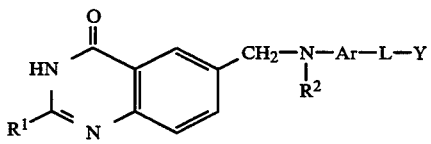

wherein

R¹ is hydrogen or amino, or alkyl or alkoxy each of up to 6 carbon atoms;

or R¹ is alkyl of up to 3 carbon atoms which bears a hydroxy substituent, or which bears one, two or three fluoro substituents;

or R¹ is hydroxyalkoxy of up to 3 carbon atoms or alkoxyalkoxy of up to 6 carbon atoms;

wherein the quinazoline ring may bear no further substituents or may bear one further substituent selected from halogeno and from alkyl and alkoxy each of up to 3 carbon atoms;

wherein R² is hydrogen, alkyl, alkenyl, alkynyl, hydroxyalkyl, halogenoalkyl or cyanoalkyl each of up to 6 carbon atoms;

wherein Ar is phenylene, thienylene or pyridylene which may be unsubstituted or may bear one or two substituents selected from halogeno, hydroxy, amino and nitro, and from alkyl, alkoxy and halogenoalkyl each of up to 3 carbon atoms;

wherein L is a group of the formula —CO.NH—, —CO.NR³— or —CO.O—, wherein R³ is alkyl of up to 6 carbon atoms; and wherein Y is heteroaryl or a hydrogenated derivative thereof; or Y is a group of the formula —A—Y¹ in which A is alkylene of up to 6 carbon atoms, and Y¹ is heteroaryl or a hydrogenated derivative thereof;

wherein one constituent methylene group in A may be replaced by an oxy, thio, sulphinyl, sulphonyl or imino group or an alkylimino group of up to 6 carbon atoms; and wherein each of said heteroaryl groups, or hydrogenated derivatives thereof, may be unsubstituted or may bear up to three substituents selected i) from hydroxy, oxo, amino, nitro, cyano, carbamoyl, sulphamoyl, carboxy and halogeno, ii) from alkyl, alkylamino, dialkylamino, N-alkylcarbamoyl, N,N-dialkylcarbamoyl, alkoxycarbonyl, alkanoyloxyalkyl, alkylthio, alkylsulphinyl, alkysulphonyl, alkoxy, halogenoalkyl, hydroxyalkyl, aminoalkyl, alkylaminoalkyl, dialkylaminoalkyl, carboxyalkyl, alkoxycarbonylalkyl, carbamoylalkyl, N-alkylcarbamoylalkyl and N,N-dialkylcarbamoylalkyl each of up to 6 carbon atoms, and iii) from phenyl, pyridyl and phenylalkyl of up to 10 carbon atoms, and wherein each of said phenyl or phenylalkyl groups may bear a substituent selected from halogeno and nitro, and from alkyl and alkoxy each of up to 3 carbon atoms;

or a pharmaceutically-acceptable salt thereof;

provided that when R¹ is hydrogen or amino, or alkyl of up to 6 carbon atoms, and L is a group of the formula —CONH—, then Y is not tetrazolyl.

2. A quinazoline of the formula I as claimed in claim 1 wherein R¹ is hydrogen or amino, or methyl, ethyl, methoxy or fluoromethyl;

wherein the quinazoline ring may bear no further substituents or may bear one further substituent selected from fluoro, chloro, methyl and methoxy;

wherein R² is methyl, ethyl, propyl, prop-2-enyl, prop-2-ynyl, 2-hydroxyethyl, 3-hydroxypropyl, 2-fluoroethyl, 2-bromoethyl or cyanomethyl;

wherein Ar is 1,4-phenylene, thienylene or pyridylene, which is unsubstituted or which bears a substituent selected from fluoro, chloro, bromo, hydroxy, amino, nitro, methyl, methoxy and trifluoromethyl;

wherein L is a group of the formula —CO.NH—, —CO.NR³— or —CO.O—, wherein R³ is methyl or ethyl; and Y is 2,5-dioxopyrrolidinyl or 2,6-dioxopiperidinyl, or Y is a group of the formula —A—Y¹ in which A is methylene, ethylene, ethylidine, trimethylene, propylidene, propylene, butylidene, isobutylidene or tetramethylene and Y¹ is furyl, thienyl, pyridyl, quinolyl, isoquinolyl, pyrazinyl, pyrimidinyl, quinazolinyl, pyridazinyl, indolyl, imidazolyl, benzimidazolyl, pyrazolyl, indazolyl, oxazolyl, isoxazolyl, thiazolyl, 1,2,3-triazolyl, 1,2,4-triazolyl, tetrazolyl or hexahydro-2-oxoazepin-1-yl; wherein one constituent methylene group in A may be replaced by a thio, sulphinyl, sulphonyl or imino group; and wherein each of said or heteroaryl groups, or hydrogenated derivatives thereof, may be unsubstituted or may bear up to three substituents selected from hydroxy, oxo, amino, nitro, cyano, carbamoyl, sulphamoyl, carboxy, fluoro, chloro, bromo, methyl, ethyl, methylamino, ethylamino, dimethylamino, diethylamino, N-methylcarbamoyl, N-ethylcarbamoyl, N,N-dimethylcarbamoyl, N,N-diethylcarbamoyl, methoxycarbonyl, ethoxycarbonyl, tert-butoxycarbonyl, isobutyryloxymethyl, pivaloyloxymethyl, methylthio, ethylthio, methylsulphinyl, ethysulphinyl, methylsulphonyl, ethylsulphonyl, methoxy, ethoxy, trifluoromethyl, carboxymethyl, 1-carboxyethyl, 2-carboxyethyl, 3- carboxypropyl, carbamoylmethyl, N-methylcarbamoylmethyl, N,N-dimethylcarbamoylmethyl, phenyl, pyridyl, benzyl, phenethyl or phenylpropyl, and wherein any phenyl group within said substituents may bear a substituent selected from fluoro, chloro, bromo, nitro, methyl, ethyl, methoxy and ethoxy;

or a pharmaceutically-acceptable salt thereof.

3. A quinazoline of the formula I as claimed in claim 1 wherein $R^1$ is amino, methyl, methoxy or fluoromethyl;

wherein the quinazoline ring may bear no further substituents or may bear one further substituent selected from fluoro, chloro, methyl and methoxy;

wherein $R^2$ is methyl, ethyl, prop-2-enyl or prop-2-ynyl;

wherein Ar is 1,4-phenylene or thienylene, pyridylene which is unsubstituted or which bears a fluoro or nitro substituent;

wherein L is a group of the formula —CO.NH— or —CO.O—; and

Y is a group of the formula —A—$Y^1$ in which A is methylene, ethylene, ethylidene, trimethylene, propylidene, propylene or isobutylidene and $Y^1$ is 2-thienyl, 2-pyridyl, 3-pyridyl, 4-pyridyl, 3-quinolyl, 4-quinolyl, 8-quinolyl, 2-pyrimidinyl, 4-pyrimidinyl, 6-quinazolinyl, 3-indolyl, 1-imidazolyl, 2-imidazolyl, 4-imidazolyl, 2-benzimidazolyl, 2-thiazolyl, 5-thiazolyl, 1,2,4-triazol-1-yl, 1,2,4-triazol-3-yl or tetrazol-5-yl and wherein each of said heteroaryl groups may be unsubstituted or may bear up to three substituents selected from hydroxy, oxo, amino, nitro, cyano, carbamoyl, carboxy, fluoro, chloro, methyl, ethyl, N-methylcarbamoyl, N,N-dimethylcarbamoyl, methoxycarbonyl, ethoxycarbonyl, pivaloyloxymethyl, methoxy, trifluoromethyl, carboxymethyl, 1-carboxyethyl, 2-carboxyethyl, 3-carboxypropyl, 4-pyridyl and benzyl;

or a pharmaceutically-acceptable salt thereof.

4. A quinazoline of the formula I as claimed in claim 1 wherein $R^1$ is amino, methyl or methoxy;

wherein the quinazoline ring may bear a methyl substituent in the 7-position;

wherein $R^2$ is methyl, ethyl or prop-2-ynyl;

wherein Ar is 1,4-phenylene or thien-2,5-diyl, or is pyrid-2,5-diyl with the group —L—Y in the 2-position, or is 2-fluoro-1,4-phenylene with the group —L—Y in the 1-position;

wherein L is a group of the formula —CONH—;

and wherein Y is thiazol-5-ylmethyl or 1,2,3,6-tetrahydro-2,6-dioxopyrimidin-4-ylmethyl, or Y is 2,3-dihydro-4-oxoquinazolin-6-ylmethyl which may bear one or two methyl substituents;

or a pharmaceutically-acceptable salt thereof.

5. A quinazoline of the formula I as claimed in claim 1 wherein $R^1$ is methyl; wherein the quinazoline ring may bear a methyl substituent in the 7-position;

wherein $R^2$ is methyl or prop-2-ynyl;

wherein Ar is 1,4-phenylene, or 2-fluoro-1,4-phenylene with the group —L—Y in the 1-position;

wherein L is a group of the formula —CO.NH—; and Y is a group of the formula —A—$Y^1$ in which A is methylene and 3-trifluoromethylphenyl, or $Y^1$ is 5-thiazolyl, 2,3-dihydro-4-oxoquinazolin-6-yl, 2,3-dihydro-2-methyl-4-oxoquinazolin-6-yl or 2,3-dihydro-2,3-dimethyl-4-oxoquinazolin-6-yl;

or a pharmaceutically-acceptable salt thereof.

6. The quinazoline p-[N-(3,4-dihydro-2-methyl-4-oxoquinazolin-6-ylmethyl)-N-(prop-2-ynyl)amino]-N-(3,4-dihydro-2-methyl-4-oxoquinazolin-6-ylmethyl)benzamide; or a pharmaceutically-acceptable salt thereof.

7. A quinazoline of the formula I as claimed in claim 1 wherein $R^1$ is alkyl or alkoxy each of up to 6 carbon atoms; or $R^1$ is alkyl of up to 3 carbon atoms which bears a hydroxy substituent, or which bears one, two or three fluoro substituents; or $R^1$ is hydroxyalkoxy of up to 3 carbon atoms or alkoxyalkoxy of up to 6 carbon atoms;

wherein the quinazoline ring may bear no further substituents or may bear one further substituent selected from halogeno and from alkyl and alkoxy each of up to 3 carbon atoms;

wherein $R^2$ is hydrogen, alkyl, alkenyl, alkynyl, hydroxyalkyl, halogenalkyl or cyanoalkyl each of up to 6 carbon atoms;

wherein Ar is phenylene, thienylene or pyridylene which may be unsubstituted or may bear one or two substituents selected from halogeno, hydroxy and amino, and from alkyl, alkoxy and halogenoalkyl each of up to 3 carbon atoms;

wherein L is a group of the formula —CO.NH—, —CO.$NR^3$— or —CO.O—, wherein $R^3$ is alkyl of up to 6 carbon atoms; and wherein Y is heteroaryl or a hydrogenated derivative thereof; or Y is a group of the formula —A—$Y^1$ in which A is alkylene of up to 6 carbon atoms, and $Y^1$ is heteroaryl or a hydrogenated derivative thereof;

wherein one constituent methylene group in A may be replaced by an oxy, thio, sulphinyl, sulphonyl or imino group or an alkylimino group of up to 6 carbon atoms; and wherein each of said heteroaryl groups, or hydrogenated derivatives thereof, may be unsubstituted or may bear one or two substituents selected i) from hydroxy, amino, nitro, cyano, carbamoyl, carboxy and halogeno, ii) from alkyl, alkylamino, dialkylamino, N-alkylcarbamoyl, N,N-dialkylcarbamoyl, alkoxycarbonyl, alkylthio, alkylsulphinyl, alkylsulphonyl, alkoxy, halogenoalkyl, hydroxyalkyl, aminoalkyl, alkylaminoalkyl, dialkylaminoalkyl, carboxyalkyl, alkoxycarbonylalkyl, carbamoylalkyl, N-alkylcarbamoylalkyl and N,N-dialkylcarbamoylalkyl each of up to 6 carbon atoms, and iii) from phenyl and phenylalkyl of up to 10 carbon atoms, and wherein each of said phenyl groups may bear a substituent selected from halogeno and from alkyl and alkoxy each of up to 3 carbon atoms;

or a pharmaceutically-acceptable salt thereof;

provided that when $R^1$ is alkyl of up to 6 carbon atoms, the quinazoline ring bears no further substituents or bears one further substituent selected from halogeno and alkyl of up to 3 carbon atoms, $R^2$ is alkyl, alkenyl or alkynyl each of up to 6 carbon atoms, Ar is phenylene which is unsubstituted or bears one or two substituents selected from halogeno, hydroxy and amino, and L is a group of the formula —CONH—, then Y is not tetrazolyl-5-yl.

8. A quinazoline of the formula I as claimed in claim 1, wherein $R^1$ is methyl, ethyl, methoxy or fluoromethyl;

wherein the quinazoline ring may bear no further substituents or may bear one further substituent selected from fluoro, chloro, methyl and methoxy;

wherein $R^2$ is hydrogen, methyl, ethyl, propyl, prop-2-enyl, prop-2-ynyl, 2-hydroxyethyl, 3-hydroxypropyl, 2-fluoroethyl, 2-bromoethyl or cyanomethyl;

wherein Ar is 1,4-phenylene, thienylene or pyridylene, which is unsubstituted or which bears one or two substituents selected from fluoro, chloro, bromo, hydroxy, amino, methyl, methoxy and trifluoromethyl;

wherein L is a group of the formula —CO.NH—, —CO.NR$^3$—, or —CO.O—, wherein $R^3$ is methyl or ethyl; and Y is pyridyl, quinolyl, isoquinolyl, pyrimidinyl, indolyl, imidazolyl, benzimidazolyl, pyrazolyl, indazolyl, oxazolyl, thiazolyl, 1,2,3-triazolyl, 1,2,4-triazolyl, thiadiazolyl or tetrazolyl; or Y is a group of the formula —A—Y$^1$ in which A is methylene, ethylene, ethylidene, trimethylene, propylidene, propylene, 1-isopropylethylene or tetramethylene and Y$^1$ is pyridiyl, quinolyl, isoquinolyl, pyrazinyl, pyrimidinyl, pyridazinyl, indolyl, imidazolyl, benzimidazolyl, pyrazolyl, indazolyl, oxazolyl, thiazolyl, 1,2,3-triazolyl, 1,2,4-triazolyl, thiadiazolyl or tetrazolyl;

wherein one constituent methylene group in A may be replaced by an oxy, thio, sulphinyl or sulphonyl group; and wherein each of said heteroaryl groups, or hydrogenated derivatives thereof, may be unsubstituted or may bear one or two substituents selected from hydroxy, amino, nitro, cyano, carbamoyl, carboxy, fluoro, chloro, bromo, methyl, ethyl, methylamino, ethylamino, dimethylamino, diethylamino, N-methylcarbamoyl, N-ethylcarbamoyl, N,N-dimethylcarbamoy, N,N-diethylcarbamoyl, methoxycarbonyl, ethoxycarbonyl, tert-butoxycarbonyl, methylthio, ethylthio, methylsulphinyl, ethylsulphinyl, isopropylsulphinyl, methylsulphonyl, ethylsulphonyl, isopropylsulphonyl, methoxy, ethoxy, trifluoromethyl, carboxymethyl, 2-carboxyethyl, carbamoylmethyl, N-methylcarbamoylmethyl, N,N-dimethylcarbamoylmethyl, phenyl, benzyl, phenethyl or phenylpropyl, and wherein each of said phenyl groups may bear a substituent selected from fluoro, chloro, bromo, methyl, ethyl, methoxy and ethoxy;

or a pharmaceutically acceptable salt thereof;

provided that when $R^1$ is methyl or ethyl, the qunazoline ring bears no further substituents or bears one further substituent selected from fluoro, chloro and methyl, $R^2$ is methyl, ethyl, propyl, prop-2-enyl or prop-2-ynyl, Ar is 1,4-phenylene which is unsubstituted or bears one or two substituents selected from fluoro, chloro, bromo, hydroxy and amino, and L is a group of the formula —CONH—, then Y is not tetrazol-5-yl.

9. A quinazoline of the formula I as claimed in claim 1 wherein $R^1$ is methyl, ethyl, methoxy or fluoromethyl;

wherein the quinazoline ring may bear no further substituents or may bear one further substituent selected from fluoro, chloro, methyl and methoxy;

wherein $R^2$ is hydrogen, methyl, ethyl, propyl, prop-2-enyl, prop-2-ynyl, 2-hydroxyethyl, 3-hydroxypropyl, 2-fluoroethyl, 2-bromoethyl or cyanomethyl;

wherein Ar is 1,4-phenylene, thien-2,5-diyl or pyrid-2,5-diyl which is unsubstituted or which bears one or two substituents selected from fluoro, chloro, hydroxy, amino and methyl;

wherein L is a group of the formula —CO.NH—, —CO.NR$^3$— or —CO.O—, wherein $R^3$ is methyl or ethyl; and Y is pyridyl, pyrimidinyl, imidazolyl, thiazolyl or 1,2,3-triazolyl; or Y is a group of the formula —A—Y$^1$ in which A is methylene, ethylene, ethylidene or trimethylene and Y$^1$ is pyridyl, quinolyl, isoquinolyl, pyrimidinyl, indolyl, imidazolyl, benzimidazolyl, pyrazolyl, indazolyl, thiazolyl, 1,2,3-triazolyl, 1,2,4-triazolyl, thiadiazolyl or tetrazolyl; and wherein each of said heteroaryl groups may be unsubstituted or may bear one or two substituents selected from amino, nitro, fluoro, methyl, carbamoyl, N-methylcarbamoyl, N,N-dimethylcarbamoyl, methoxycarbonyl, ethoxycarbonyl, methylsulphinyl, methylsulphonyl, methoxy, trifluoromethyl or benzyl;

or a pharmaceutically-acceptable salt thereof.

10. A quinazoline of the formula I as claimed in claim 1 wherein $R^1$ is methyl; wherein $R^2$ is hydrogen, methyl, ethyl, prop-2-ynyl or 2-fluoroethyl;

wherein Ar is 1,4-phenylene or thien-2,5-diyl, is pyrid-2,5-diyl or with the group —L—Y in the 2-position, or is 2-fluoro-1,4-phenylene with the group —L—Y in the 1-position;

wherein L is a group of the formula —CO.NH—, —CO.NR$^3$— or —CO.O—, wherein $R^3$ is methyl or ethyl; and wherein Y is a group of the formula —A—Y$^1$ in which A is methylene, ethylene, ethylidene or trimethylene and Y$^1$ is 2-pyridyl, 3-pyridyl, 4-pyridyl, 1-isoquinolyl, 3-isoquinolyl, 4-isoquinolyl, 2-pyrimidinyl, 4-pyrimidinyl, 5-pyrimidinyl, 2-indolyl, 3-indolyl, 1-imidazolyl, 2-imidazolyl, 2-benzimidazolyl, 1-pyrazolyl, 3-pyrazolyl, 4-pyrazolyl, 3-indazolyl, 2-thiazolyl, 4-thiazolyl, 5-thiazolyl, 1,2,3-triazol-4-yl, 1,2,4-triazol-3-yl, 1,2,4-triazol-4-yl, 1,2,4-triazol-1-yl, 2-thiadiazolyl or 5-tetrazolyl; and wherein each of said heteroaryl groups may be unsubstituted or may bear one or two substituents selected from amino, nitro, carbamoyl, fluoro, methyl, ethoxycarbonyl, methylsulphinyl, methylsulphonyl, methoxy, trifluoromethyl or benzyl;

or a pharmaceutically-acceptable salt thereof.

11. A quinazoline of the formula I as claimed in claim 1 wherein $R^1$ is methyl;

wherein $R^2$ is methyl, ethyl or prop-2-ynyl;

wherein Ar is 1,4-phenylene or thien-2,5-diyl, or is pyrid-2,5-diyl with the group —L—Y in the 2-position, or is 2-fluoro-1,4-phenylene with the group —L—Y in the 1-position; wherein L is a group of the formula —CO.NH— and Y is a group of the formula —A—Y¹ in which A is methylene or ethylene and Y¹ is 2-pyridyl, 3-pyridyl, 4-pyridyl, 3-indolyl or 1,2,4-triazol-1-yl, or a pharmaceutically-acceptable salt thereof.

12. A quinazoline selected from the group of compounds:

p-[N-(3,4-dihydro-2-methyl-4-oxoquinazolin-6-ylmethyl)-N-(prop-2-ynyl)amino]-N-(3-pyridylmethyl)-benzamide and N-benzylimidazol-2-ylmethyl p-[N-(3,4-dihydro-2-methyl-4-oxoquinazolin-6-ylmethyl)-N-ethylamino]-benzoate.

13. A pharmaceutical composition which comprises a quinazoline as claimed in claim 1, or a pharmaceutically-acceptable salt thereof, in association with a pharmaceutically-acceptable diluent or carrier.

* * * * *